(12) United States Patent
Leuthardt et al.

(10) Patent No.: US 11,667,975 B2
(45) Date of Patent: Jun. 6, 2023

(54) METHODS AND SYSTEMS FOR NONINVASIVE AND LOCALIZED BRAIN LIQUID BIOPSY USING FOCUSED ULTRASOUND

(71) Applicant: Washington University, St. Louis, MO (US)

(72) Inventors: Eric Leuthardt, St. Louis, MO (US); Gavin Dunn, St. Louis, MO (US); Hong Chen, St. Louis, MO (US); Allegra Petti, St. Louis, MO (US)

(73) Assignee: Washington University, St. Louis, MO (US)

( * ) Notice: Subject to any disclaimer, the term of this patent is extended or adjusted under 35 U.S.C. 154(b) by 1078 days.

(21) Appl. No.: 16/393,322

(22) Filed: Apr. 24, 2019

(65) Prior Publication Data
US 2019/0323086 A1    Oct. 24, 2019

Related U.S. Application Data

(60) Provisional application No. 62/662,013, filed on Apr. 24, 2018.

(51) Int. Cl.
| | | |
|---|---|---|
| *A61B 5/05* | (2021.01) | |
| *C12Q 1/6886* | (2018.01) | |
| *A61B 10/00* | (2006.01) | |
| *A61N 7/00* | (2006.01) | |
| *A61B 5/055* | (2006.01) | |
| *A61B 5/00* | (2006.01) | |
| *C12Q 1/6851* | (2018.01) | |
| *A61B 90/11* | (2016.01) | |

(52) U.S. Cl.
CPC ......... *C12Q 1/6886* (2013.01); *A61B 5/0042* (2013.01); *A61B 5/055* (2013.01); *A61B 5/6803* (2013.01); *A61B 10/0045* (2013.01); *A61B 90/11* (2016.02); *A61N 7/00* (2013.01); *C12Q 1/6851* (2013.01); *A61B 2010/008* (2013.01); *A61B 2010/0077* (2013.01); *A61N 2007/006* (2013.01); *A61N 2007/0039* (2013.01); *A61N 2007/0078* (2013.01); *C12Q 2600/156* (2013.01)

(58) Field of Classification Search
CPC combination set(s) only.
See application file for complete search history.

(56) References Cited

U.S. PATENT DOCUMENTS

| | | |
|---|---|---|
| 5,752,515 A | 5/1998 | Jolesz et al. |
| 9,457,202 B2 | 10/2016 | Sangvhi et al. |

(Continued)

OTHER PUBLICATIONS

Aldiabat, H. et al. (Apr. 17, 2018), Wideband transskull refocusing of ultrasound beams using dual-mode ultrasound arrays: Ex vivo results, J. Acoust. Soc. Am., vol. 143, pp. 1731.

(Continued)

*Primary Examiner* — Joel F Brutus
(74) *Attorney, Agent, or Firm* — Polsinelli, PC

(57) ABSTRACT

Among the various aspects of the present disclosure is the provision of a noninvasive and localized brain liquid biopsy using focused ultrasound. Briefly, therefore, the present disclosure is directed to methods and systems to identify brain lesion or tumor characteristics without the need for a solid brain biopsy.

46 Claims, 19 Drawing Sheets
Specification includes a Sequence Listing.

(56) References Cited

U.S. PATENT DOCUMENTS

| | | | | |
|---|---|---|---|---|
| 2012/0289869 | A1* | 11/2012 | Tyler | A61B 5/369 |
| | | | | 601/2 |
| 2013/0196873 | A1* | 8/2013 | Wurdinger | A61P 35/02 |
| | | | | 435/6.12 |
| 2014/0193834 | A1* | 7/2014 | Bhatt | G01N 33/6857 |
| | | | | 435/7.1 |
| 2015/0265353 | A1 | 9/2015 | Andrews et al. | |
| 2015/0360020 | A1* | 12/2015 | Wu | A61N 7/00 |
| | | | | 600/411 |
| 2016/0129131 | A1* | 5/2016 | Vitari | A61K 47/6921 |
| | | | | 424/9.4 |
| 2017/0000376 | A1 | 1/2017 | Partanen et al. | |
| 2017/0043149 | A1* | 2/2017 | Liu | A61M 37/0092 |

OTHER PUBLICATIONS

Arvanitis, C. D. et al. (2016), Passive acoustic mapping with the angular spectrum method, IEEE Trans. Med. Imaging, vol. 36, No. 4, pp. 983-993.

Aryal, M. et al. (2014), Ultrasound-mediated blood-brain barrier disruption for targeted drug delivery in the central nervous system, Adv. Drug Deliv. Rev., vol. 72, pp. 94-109.

Aum, D. J. et al. (2014), Molecular and cellular heterogeneity: the hallmark of glioblastoma, Neurosurg., vol. 37, No. 6, pp. 1-11.

Bardelli, A. et al. (2017), Liquid biopsies, what we do not know (yet), Cancer Cell, vol. 31, pp. 172-179.

Baseri, B. et al. (2010), Multi-modality safety assessment of blood-brain barrier opening using focused ultrasound and definity microbubbles: a short-term study, Ultrasound Med. Biol., vol. 36, No. 9, pp. 1445-1459.

Beach, T.G. (2017), A review of biomarkers for neurodegenerative disease: will they swing us across the valley?, Neurol. Ther., vol. 6, Supp 1, pp. S5-S13.

Bettegowda C., et al. (2014), Detection of circulating tumor DNA in early- and late-stage human malignancies, Sci Transl Med, vol. 6, No. 224, pp. 224ra24.

Blomley, M.J.K et al. (2001), "Science, medicine, and the future:Microbubble contrast agents: A new era in ultrasound", BMJ, vol. 322, No. 7296, pp. 1222-1225.

Boisselier, B. et al. (2012), Detection of IDH1 mutation in the plasma of patients with glioma, Neurology, vol. 79, No. 16, pp. 1693-1698.

Burgess, A. et al. (2013), Noninvasive and targeted drug delivery to the brain using focused ultrasound, ACS Chem. Neurosci., vol. 4, No. 4, pp. 519-526.

Burgess, A. et al. (2015), Focused ultrasound-mediated drug delivery through the blood-brain barrier, Expert Rev. Neurother., vol. 15, No. 5, pp. 477-491.

Capper, D. et al. (2012), 2-Hydroxyglutarate concentration in serum from patients with gliomas does not correlate with 1DH1/2 mutation status or tumor size, Int. J. Cancer, vol. 131, pp. 766-768.

Chen, H. et al. (2014), The size of blood-brain barrier opening induced by focused ultrasound is dictated by the acoustic pressure, J. Cereb. Blood Flow Metab., vol. 34, pp. 1197-1204.

Chen, H. et al. (2014), A new brain drug delivery strategy: focused ultrasound-enhanced intranasal drug delivery, PLoS One, vol. 9, No. 10, pp. e108880.

Chevillet, J. R. et al. (2016), Release of cell-free microRNA tumor biomarkers into the blood circulation with pulsed focused ultrasound: A noninvasive, anatomically localized, molecular liquid biopsy, Radiology, vol. 283, No. 1, pp. 158-167.

Choi, J. J. et al. (2010), Microbubble-size dependence of focused ultrasound-induced blood-brain barrier opening in mice in vivo, IEEE Trans. Biomed. Eng., vol. 57, No. 1, pp. 145-154.

Choi, J. J. et al. (2011), Noninvasive and localized neuronal delivery using short ultrasonic pulses and microbubbles, Proc. Natl. Acad. Sci. U. S. A, vol. 108, No. 40, pp. 16539-16544.

Cohen, J. D. et al. (Feb. 2018), Detection and localization of surgically resectable cancers with a multi-analyte blood test, Science, vol. 359, No. 6378, pp. 926-930.

Cyll, K. et al. (2017), Tumour heterogeneity poses a significant challenge to cancer biomarker research, BJC, vol. 117, pp. 367-375.

Downs, M. E. et al. (2015), Long-term safety of repeated blood-brain barrier opening via focused ultrasound with microbubbles in non-human primates performing a cognitive task, PLoS One, vol. 10, No. 5, pp. e0125911.

D'Souza, A. L. et al. (2009), A strategy for blood biomarker amplification and localization using ultrasound, Proc. Natl. Acad. Sci. U. S. A., vol. 106, No. 40, pp. 17152-17157.

D'Souza, A. L. et al. (Mar. 2018), Tumor characterization by ultrasound-release of multiple protein and microRNA biomarkers, preclinical and clinical evidence, PLoS One, vol. 13, No. 3, pp. e0194268.

El Kaffas, A. et al. (2015), Biomechanical effects of microbubbles: from radiosensitization to cell death, Future Oncol., vol. 11, No. 7, pp. 1093-1108.

Ellens, N. et al. (2016), Pre-clinical MRI-guided focused ultrasound: A review of systems and current practices, IEEE Trans. Ultrason. Ferroelectr. Freq. Control, vol. 64, No. 1, pp. 291-305.

Figueroa, J. M. et al. (2017), Detection of wild-Type EGFR amplification and EGFRvIII mutation in CSF-derived extracellular vesicles of glioblastoma patients, Neuro. Oncol., vol. 19, No. 1, pp. 1494-1502.

Fisher, J. L. et al. (2007), Epidemiology of brain tumors, Neurol. Neurol Clin, vol. 25, pp. 867-890.

Forbrich, A. et al. (2013), Microbubble-enhanced ultrasound liberation of mRNA biomarkers in vitro, Ultrasound Med. Biol., vol. 39, No. 6, pp. 1087-1093.

Jadhav, V. et al. (2007), Neuroprotection against Surgically-Induced Brain Injury, Surg Neurol., vol. 67, pp. 15-20.

Jain K.K (2015), Biomarkers in Neurology, Neurology Medlink, retrieved from https://www.medlink.com/index.php/article/biomarkers_in_neurology#S1 on Sep. 17, 2019, pp. 1-3.

Jeromin A. et al. (2017), Biomarkers in Neurodegenerative Diseases, Neurodegenerative Diseases: Pathology, Mechanisms, and Potential Therapeutic Targets, Adv. Neurobiol. vol. 15, pp. 491-528, Springer International Publishing.

Jones, R. M. et al. (Apr. 16, 2018), Three-dimensional transcranial microbubble imaging for guiding volumetric ultrasound-mediated blood-brain barrier opening, Theranostics vol. 8, No. 11, pp. 2909-2926.

Kinoshita, M. et al. (2006), Noninvasive localized delivery of Herceptin to the mouse brain by MRI-guided focused ultrasound-induced blood-brain barrier disruption, Proc Natl Acad Sci, vol. 103, No. 31, pp. 11719-11723.

Kothapalli, S. V. V. N. et al. (2017), Acoustic field characterization of a clinical magnetic resonance-guided high-intensity focused ultrasound system inside the magnet bore, Med. Phys., vol. 44, No. 9, pp. 4890-4899.

Kothapalli, S. V. V. N. et al. (Jul. 2018), A convenient, reliable, and fast acoustic pressure field measurement method for magnetic resonance-guided high-intensity focused ultrasound systems with phased array transducers, J. Ther. Ultrasound, vol. 6, No. 5, pp. 1-8.

Lun, M. et al. (2011), The natural history of extracranial metastasis from glioblastoma multiforme, J. Neurooncol., vol. 105, No. 2, pp. 261-273.

Malone, H. et al. (2015), Complications following stereotactic needle biopsy of intracranial tumors, World Neurosurg., vol. 84, No. 4, pp. 1084-1089.

Martin, E. et al. (2009), High-intensity focused ultrasound for noninvasive functional neurosurgery, Ann. Neurol., vol. 66, No. 6, pp. 858-861.

Mcdannold, N. et al. (2012), Temporary disruption of the blood-brain barrier by use of ultrasound and microbubbles: safety and efficacy evaluation in rhesus macaques, Cancer Res., vol. 72, No. 14, pp. 3652-3663.

Merker, J. D. et al. (Oct. 2018), Circulating tumor DNA analysis in patients with cancer: American society of clinical oncology and college of American pathologists joint review, Arch. Pathol. Lab. Med., vol. 142, No. 10, pp. 1242-1253.

(56) References Cited

OTHER PUBLICATIONS

Miller, A. M. et al. (Jan. 2019), Tracking tumour evolution in glioma through liquid biopsies of cerebrospinal fluid, Nature, vol. 565, No. 7741, pp. 654-658.
Morel, D. R. et al. (2000), Human pharmacokinetics and safety evaluation of SonoVueTM, a new contrast agent for ultrasound imaging, Invest. Radiol., vol. 35, No. 1, pp. 80-85.
Mornstein, V. (1997), Cavitation-induced risks associated with contrast agents used in ultrasonography, European Journal of Ultrasound, vol. 5, pp. 101-111.
Olumolade, O. O. et al. (2016), Longitudinal motor and behavioral assessment of blood-brain barrier opening with transcranial focused ultrasound, Ultrasound Med. Biol., vol. 42, No. 9, pp. 2270-2282.
Omuro, A. M. P. et al. (2006), Pitfalls in the diagnosis of brain tumours, vol. 5, pp. 937-948.
Omuro, A. et al. (2013), Glioblastoma and other malignant gliomas: a clinical review, Jama, vol. 310, No. 17, pp. 1842-1850.
O'Reilly, M. A. et al. (2012), Feedback-controlled focused ultrasound disruption by using an acoustic emissions-based controller, Radiology, vol. 263, No. 1, pp. 96-106.
Paproski, R. J. et al. (2016), Enhanced detection of cancer biomarkers in blood-borne extracellular vesicles using nanodroplets and focused ultrasounc, Cancer Res., vol. 77, No. 1, pp. 3-13.
Peng, D. et al. (2014), A study of ovarian cancer biomarker amplification using ultrasound for early stage detection, Ultrasonics, vol. 54, pp. 451-454.
Radovini, N. N. (2015), World first: blood-brain barrier opened non-invasively to deliver chemotherapy, Sunnybrook Health Sciences Centre, Retrieved from https://sunnybrook.ca/media/item.asp?i=1351 on Sep. 22, 2019, pp. 1-2.
Radovini, N. N. (2017), First Alzheimer's patient treated with focused ultrasound to open the blood-brain barrier, Sunnybrook Health Sciences Centre, Retrieved from https://sunnybrook.ca/media/item.asp?i=1562 on Sep. 22, 2019, pp. 1-3.
Ragel, B. T. et al. (2015), The role of biopsy in the management of patients with presumed diffuse low grade glioma: A systematic review and evidence-based clinical practice guideline, J. Neurooncol., vol. 125, No. 3, pp. 481-501.
Schmittgen, T. D., et al. (2008), Analyzing real-time PCR data by the comparative CT method, Nat. Protoc., vol. 3, No. 6, pp. 1101-1108.
Sirsi, S. et al. (2009), Microbubble compositions, properties, and biomedical applications, Bubble Sci Eng Technol, vol. 1, No. 1-2, pp. 3-17.
Smith, C. (2017), Biomarkers on the brain: Putting biomarkers together for a better understanding of the nervous system, Science, Special Technology Feature, pp. 1341-1343.
Staedtke V. et al. (2016), "Actionable Molecular Biomarker: Tumors", Trends in Cancer, vol. 2, No. 7, pp. 338-349.
Stride, E. (2009), Physical principles of microbubbles for ultrasound imaging and therapy, Cerebrovasc. Dis., vol. 27, Supp. 2, pp. 1-13.
Sun, T. et al. (2017), Closed-loop control of targeted ultrasound drug delivery across the blood-brain/tumor barriers in a rat glioma model, Proc. Natl. Acad. Sci., vol. 114, pp. E10281-E10290.
Taylor, S. C. et al. (2017), Droplet Digital PCR versus qPCR for gene expression analysis with low abundant targets: from variable nonsense to publication quality data, Sci. Rep., vol. 7, No. 2409, pp. 1-8.
Touat, M et al. (2015), Emerging circulating biomarkers in glioblastoma: promises and challenges, Expert Rev. Mol. Diagn., vol. 15, No. 10, pp. 1311-1323.
Van Tellingen, O. et al. (2015), Overcoming the blood-brain tumor barrier for effective glioblastoma treatment, Drug Resist. Updat., vol. 19, pp. 1-12.
Vogel, C. et al. (2012), Insights into the regulation of protein abundance from proteomic and transcriptomic analyses, Nat. Rev. Genet., vol. 13, No. 4, pp. 227-232.
Warton, K. et al. (2016), Methylated circulating tumor DNA in blood: Power in cancer prognosis and response, Endocrine-Related Cancer, vol. 23, No. 3, pp. R157-R171.
Westphal, M. et al. (2015), Circulating biomarkers for gliomas, Nat. Publ. Gr., No. 10, pp. 556-566.
Wood, A. K. W. et al. (2015), A review of low-intensity ultrasound for cancer therapy, Ultrasound Med. Biol., vol. 41, No. 4, pp. 905-928.
Wu, S.-Y. et al. (2016), Characterizing focused-ultrasound mediated drug delivery to the heterogeneous primate brain in vivo with acoustic monitoring, Sci. Rep., vol. 6, No. 37094, pp. 1-13.
Wu, S.-Y. et al. (May 2018), Efficient blood-brain barrier opening in primates with neuronavigation-guided ultrasound and real-time acoustic mapping, Sci. Rep., vol. 8, No. 7978, pp. 1-11.
Yong, E. (2014), Cancer biomarkers: Written in blood, Nature, vol. 511, No. 7511, pp. 524-526.
Zachariah, M. A. et al. (May 2018), Blood-based biomarkers for the diagnosis and monitoring of gliomas, Neuro. Oncol., vol. 20, No. 9, pp. 1155-1161.
Zhu, L. et al. (Apr. 26, 2018), Focused ultrasound-enabled brain tumor liquid biopsy, Sci. Rep., vol. 8, No. 6553., pp. 1-9.

* cited by examiner

FIG. 1B-FIG. 1F
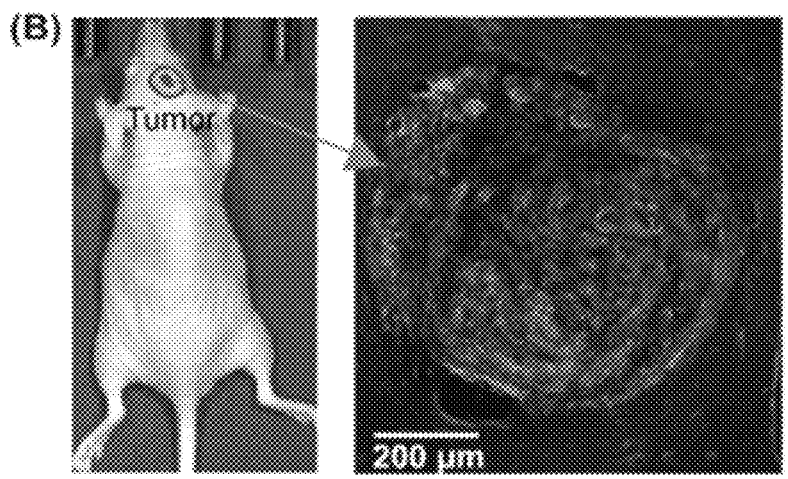
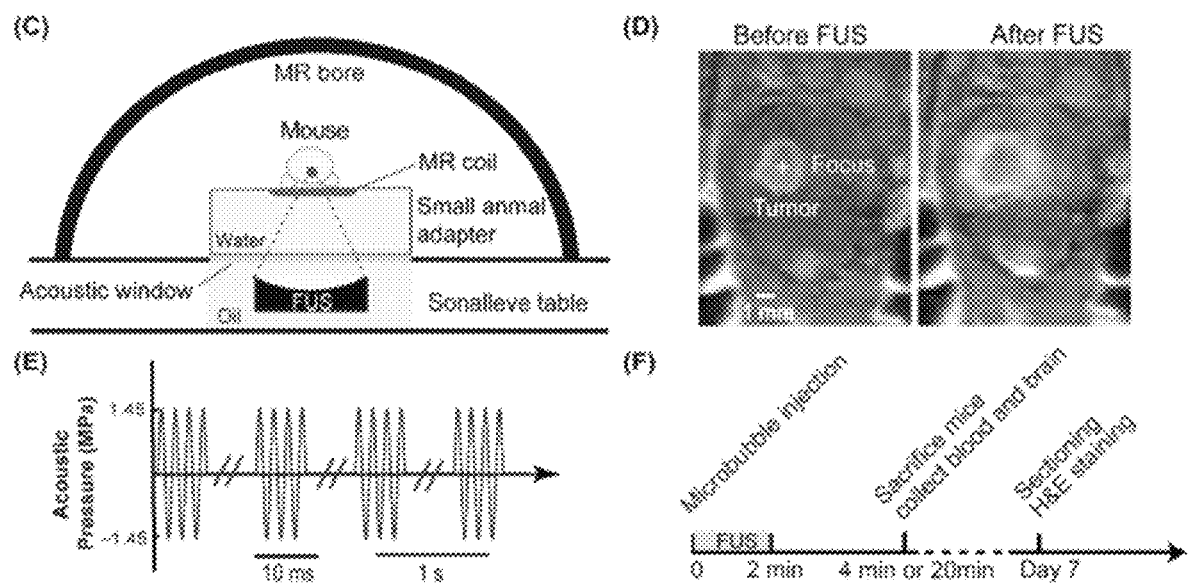

METHODS AND SYSTEMS FOR NONINVASIVE AND LOCALIZED BRAIN LIQUID BIOPSY USING FOCUSED ULTRASOUND

CROSS-REFERENCE TO RELATED APPLICATIONS

This application claims priority from U.S. Provisional Application Ser. No. 62/662,013 filed on 24 Apr. 2018, which is incorporated herein by reference in its entirety.

STATEMENT REGARDING FEDERALLY SPONSORED RESEARCH OR DEVELOPMENT

Not applicable.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present disclosure generally relates to methods and systems for non-invasive brain biopsies.

SUMMARY OF THE INVENTION

Among the various aspects of the present disclosure is the provision of a non-invasive and localized brain liquid biopsy using a focused ultrasound system. Briefly, therefore, the present disclosure is directed to improved methods to identify brain tumor or lesion characteristics without the need for a solid brain biopsy.

One aspect of the present disclosure provides for methods for non-invasively obtaining a biopsy of a brain tumor or lesion using high-resolution MRI guided focused ultrasound and blood based genetic testing or biomarker detection.

Another aspect of the present disclosure provides for methods for biopsying or diagnosing a brain tumor or lesion, non-invasively, using MRI guided ultrasound and genetic testing or biomarker detection.

Another aspect of the present disclosure provides for methods for disrupting brain tumor cells to identify genetic information or using sequencing to identify or diagnose a tumor or lesion.

Another aspect of the present disclosure provides for methods for using focused ultrasound to release genetic information across the blood brain barrier (BBB) and analyzing the genetic information.

Another aspect of the present disclosure provides for a method of non-invasively releasing biomarkers from a brain or a brain region across a blood brain barrier (BBB) of a subject.

In some embodiments, the method comprises applying a focused ultrasound (FUS) to the brain or the brain region, wherein the FUS is applied for a period of time and at an acoustic pressure sufficient to disrupt the BBB and release a detectable quantity of a biomarker across the BBB; obtaining a biological sample from the subject after applying the FUS to a subject brain or a subject brain region; or detecting a biomarker in the biological sample.

In some embodiments, the biological sample is a biological fluid selected from the group consisting of: blood, cerebral spinal fluid (CSF), interstitial fluid (ISF), serum, and plasma.

In some embodiments, the period of time sufficient to disrupt the blood brain barrier (BBB) and release a detectable quantity of a biomarker across the BBB is between about 1 minute and about 4 minutes.

In some embodiments, the acoustic pressure sufficient to disrupt the blood brain barrier (BBB) and release a detectable quantity of a biomarker across the BBB is between about 0.1 MPa and about 10 MPa.

In some embodiments, the biomarker comprises genetic material.

In some embodiments, the genetic material is selected from cell-free RNA, cell-free DNA, mRNA, circulating tumor DNA (ctDNA), or plasma DNA concentration.

In some embodiments, the biomarker is selected from D-2-hydroxyglutarate (D2HG) or IDH1(R132H) mutation.

In some embodiments, the method comprises: scanning a subject head using a magnetic resonance imaging (MRI) scanner and stereotactically coregistering the subject head and identifying a region to be targeted with the FUS.

In some embodiments, the method comprises assessing the effectiveness of the BBB disruption or release of biomarkers comprising measuring MRI contrast before and after FUS, wherein an increase in MRI contrast after FUS compared to the MRI contrast before FUS indicates successful release of biomarker from the brain or brain region.

In some embodiments, detecting the biomarker in a biological sample comprises genetic testing or sequencing.

In some embodiments, the method comprises extracting cell-free or exosomic DNA or RNA from the biological sample.

In some embodiments, the method comprises detecting somatic mutations in the DNA or RNA using a targeted ultra-deep sequencing technology selected from the group consisting of: ddPCR, AmpliSeq, and HaloPlex sequencing.

In some embodiments, the method comprises comparing a level of a biomarker in the biological sample after administering the FUS to a biological sample obtained from the subject before FUS or of a matched control sample or standard sample.

In some embodiments, the brain or brain region comprises a tumor, lesion, or suspected tumor.

In some embodiments, the subject has or is suspected of having a central nervous system cancer or tumor; a brain tumor, a brain lesion, a neurological disease, disorder, or condition, or a neurodegenerative disease disorder, or condition.

In some embodiments, the FUS is applied for a period of time and at a pressure sufficient to rupture cells at the region to release biomarkers.

In some embodiments, the method comprises administering microbubbles to a subject in an amount sufficient to disrupt the BBB upon application of FUS. In some embodiments, the method comprises providing an acoustic sensor; or detecting an acoustic signal, wherein the sensor is capable of measuring or monitoring cavitational acoustic emissions.

Another aspect of the present disclosure provides for a system suitable for use in delivering focused ultrasound (FUS) to a brain or a region of a brain of a subject. In some embodiments, the system comprises a device comprising a plurality of modular pieces configured to deliver ultrasound to the brain or a brain region. In some embodiments, the system comprises an ultrasound transducer configured to emit a FUS beam. In some embodiments, the system comprises an acoustic lens configured to control the FUS beam direction.

In some embodiments, the system is configured for incorporation into a magnetic resonance imaging (MRI) scanner, wherein the MRI scanner is configured to provide an MRI image for guiding or monitoring of the FUS.

In some embodiments, the system comprises a helmet configured to fit over a head of a subject.

In some embodiments, the helmet is demountably coupled to the ultrasound transducer; the ultrasound transducer is demountably coupled to the acoustic lens; the ultrasound transducer is a flat ultrasound transducer; the acoustic lens is a 3D printed acoustic lens; or the acoustic lens is a convex lens.

In some embodiments, the system is suitable for use in parallel with a plurality of the systems.

In some embodiments, the system comprises a sensor capable of measuring or monitoring cavitational acoustic emissions.

In some embodiments, the ultrasound transducer is configured to emit a low acoustic pressure of less than about 10 MPa.

In some embodiments, the system comprises one to eight transducers.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 1A-FIG. 1F. Experimental method. (A) Schematic illustration of the focused ultrasound (FUS) experiment setup for the treatment of U87 tumor-bearing mice. (B) Bioluminescence image of the orthotopic mouse model with the green fluorescence image of the mouse brain shown on the right. (C) Schematic illustration of the MR-guided focused ultrasound (MRgFUS) system for the treatment of GL261 tumor-bearing mice. (D) Representative contrast-enhanced MR images acquired before and after FUS treatment. The enhanced accumulation of the MR contrast agents in the tumor region verified accurate tumor targeting by the FUS. (E) Diagram of FUS pulses. (F) Illustration of the experimental timeline.

DETAILED DESCRIPTION OF THE INVENTION

Figure 1A:
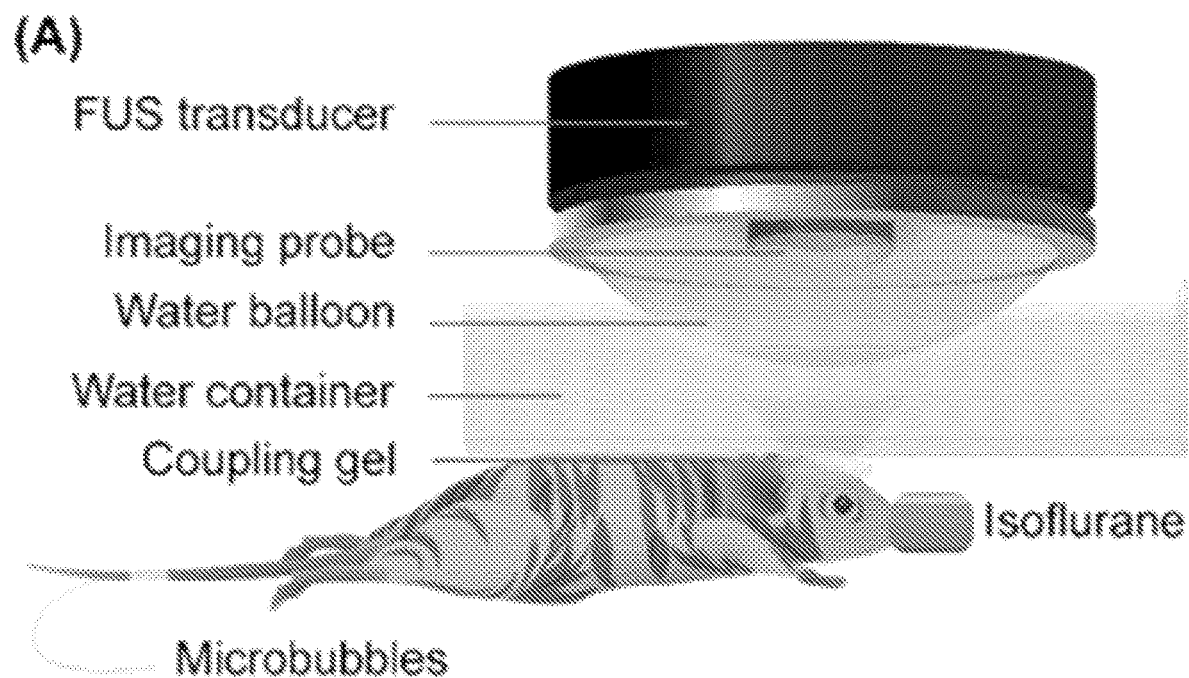

The present disclosure is based, at least in part, on the discovery that a "liquid brain biopsy" can provide similar levels of information as a standard brain biopsy. As described herein, it was demonstrated that the combination of FUS and microbubbles allows for the detection of tumor-specific mRNA in the bloodstream that is otherwise undetectable. These presently disclosed findings established that FUS-mediated BBB disruption could enhance brain-to-blood trafficking. FUS may offer an enabling technique for a noninvasive and regionally-specific brain tumor liquid biopsy that can be utilized in personalized brain cancer patient care.

In typical scenarios when a brain lesion is identified, or when a patient has a known brain tumor that has been previously treated, there is a clinical indication to perform a surgical stereotactic biopsy. This entails making a hole in the skin and skull and placing a needle probe into the lesion and aspirating a piece of tissue for histological and genetic testing to achieve a diagnosis. Also of note, there are a number of other lesions in the brain that can potentially require biopsy—lesions of unknown etiology, radiation necrosis, or known tumors, which require further clarification if genetic profile has changed, etc. This procedure can carry the surgical risks of bleeding, infection, non-diagnosis, or the requirements of general anesthesia.

This invention provides similar levels of information without the requirement for surgery. The general concept involves the following process. A lesion in the brain is identified that requires pathologic diagnosis. The lesion is imaged with MRI using high-resolution anatomic imaging (i.e., T1 and T2 sequences). The imaging is stereotactically coregistered to the patient's head using standard frameless navigation systems. Targets for biopsy are then identified with the navigation system. Once done, a focused ultrasound source is then used to target the region. The patient is concurrently given ultrasound fluoridated microbubbles (microbubbles can be optional). The focused ultrasound or combination of the ultrasound and microbubbles can induce a disruption of the blood brain barrier in the prospectively chosen target site. An alternative to the fluoridated microbubbles would be to simply have higher power focused ultrasound that creates a local tissue injury and disruption of the blood brain barrier. This US perturbation can also lead to the rupture of the cells and the release of genetic material into the blood stream. Biological samples (e.g., blood) and, optionally, matched normal samples can then be taken from the patient and genetically analyzed in order to identify biomarkers, such as circulating somatic variants. These somatic variants can then be evaluated to determine the nature of the lesion in the brain.

The technology/process can involve the novel combination of focused ultrasound and advanced genetic screening. Specifically, the ultrasound technique can be a simple, compact, and relatively inexpensive focused ultrasound system that is comprised of a single-element FUS transducer. The transducer can be coupled to a high-precision, fast-speed positioning system to steer transducer focus mechanically. It is also an option to use a focused ultrasound system comprising a phased array transducer with multiple elements for steering the transducer focal point electronically.

These techniques can be used in conjunction with either stereotactic navigation in which the patient's brain imaging and lesion localization is rigorously coregistered in physical geometric space. This can allow for precise perturbation of the intended target. Once performed, blood can be withdrawn from the patient and cell-free or exosomic DNA and/or RNA can be extracted. The DNA and/or RNA can be evaluated for the presence of somatic mutations using a targeted ultra-deep sequencing technology, examples of which include, but are not limited to, PCR, qPCR, ddPCR, AmpliSeq, or HaloPlex sequencing. The set of variants to be queried can contain patient-specific variants (identified using whole-genome or whole-exome sequencing of a surgically-resected tumor and matched normal tissue from the same patient), a panel of variants that are commonly present in brain tumors or a combination of panel variants and patient-specific variants. Optionally, genomic DNA from matched normal samples from the same patient can be sequenced and used to distinguish somatic variants from germline variants.

It is also important to note that while blood is the easiest and most accessible source of fluid to perform further genetic analysis, one could also perform this same analysis on cerebrospinal fluid (CSF) or other biological samples (e.g., blood, plasma, serum, interstitial fluid (ISF)).

Blood Brain Barrier (BBB) Opening with Focused Ultrasound (FUS)

The blood-brain barrier (BBB) blocks large molecules (>400 Da) from entering the central nervous system (CNS). Focused Ultrasound (FUS) is the only available technique to non-invasively, locally, and transiently open the BBB. Previous preclinical research using small animal models has demonstrated this technique as a promising way to treat various brain disorders. FUS in combination with microbubbles can also be used. This technique has also been tested on non-human primates with success. Clinical Studies with FUS are actively investigated for treatment of brain tumor and Alzheimer's disease. Besides its clinical translation potential, this technique has a broad application in preclinical research. This technique can be used to deliver various agents to the brain, such as chemo drugs, proteins, peptides, nanoparticles, gene vectors, and stem cells. However, currently there is a lack of devices that are affordable, high throughput, and dedicated for small animal research. Here is disclosed a FUS-induced BBB opening device that meets these needs.

The BBB, as described herein, can also comprise a blood-tumor barrier. The blood-tumor barrier is less leaky than vessels outside the central nervous system, but is leakier than a healthy BBB.

As described herein, the BBB can be opened for minutes, hours, or days, depending on the US energy administered to the subject. This can allow for serial testing of biomarkers. It is preferred to have as short of an open window as possible (e.g., on the order of minutes) because of the possibility of infection or because the detectable biomarkers can have a short half-life, are unstable, or are quickly cleared from the bloodstream. Because the half-life for many biomarkers is known, the time point for collection is known as well (e.g., the time at which a sample is taken form a subject can correlate to a time where the biomarker has not yet been cleared from the subject's system).

Focused Ultrasound (FUS) System

Disclosed herein is a focused ultrasound (FUS) system for use in disruption of a blood brain barrier (BBB), releasing biomarkers from a brain lesion or tumor. After the subject is administered the ultrasound, the biomarkers can be detected in a biological sample of a subject. Conventional FUS systems being used to open up the BBB are being used with therapeutically-relevant acoustic pressures (e.g., higher peak negative acoustic pressure (PNP) levels than used in typical diagnostic or imaging levels). For example, clinical FUS systems use relatively high acoustic pressure. The FUS systems and methods as described herein can use diagnostically-relevant acoustic pressures to open the blood brain barrier and release biomarkers from a brain lesion or suspected brain lesion.

As an example, the acoustic pressure for mice in the presently disclosed system can be about 0.6 MPa. As another example, the acoustic pressure for a human in the presently disclosed system can be about 1.5 MPa.

Furthermore, conventional clinical systems use high energy and require high precision for use in delivering treatment to a specific area, such as a tumor or lesion. The FUS system described herein does not require high energy or precision to disrupt the BBB and release biomarkers from the brain or a brain lesion. For example, a clinical FUS system can comprise over 1,000 elements (a transducer array) that are individually steered. The system described herein only requires a single element (but up to about 8 can be useful) at diagnostically-relevant energy requirements. This design decreases the cost, simplifies the design, can be adapted for human or animal use, and is designed to be incorporated into any MRI scanner.

Described herein in also a method of monitoring cavitation (e.g., microbubble behavior) (see e.g., Example 3). The FUS system can comprise a sensor that measures acoustic signal. This monitoring can inform if the acoustic pressure should be increased or decreased by measuring the acoustic signal.

As described herein, the focused ultrasound-enabled brain tumor liquid biopsy (FUS-LBx) offers a technique that can provide noninvasive, spatially resolved, and temporally controlled brain liquid biopsies. FUS has emerged as a technology with the potential to noninvasively exert mechanical and thermal effects on the brain tissue. When coupled with intravenously injected microbubbles, low-intensity pulsed FUS-induced mechanical effects can transiently and noninvasively open the BBB without causing any or substantial vascular or tissue damage. It was demonstrated (see e.g., Example 1) that FUS in combination with microbubbles could also be exploited to release biomarkers from brain tumors in murine glioblastoma models. The approach described here, is different from previously reported FUS-facilitated liquid biopsy techniques developed for in vivo biomarker release from cancers outside the brain. In one of those reports, pulsed high-intensity focused ultrasound (HIFU) with high acoustic pressures (ultrasound frequency=1.5 MHz, peak compressional focal pressure=90 MPa, and peak rarefactional focal pressure=17 MPa) was used to induce histotripsy (i.e., a technique for mechanical tissue fractionation) in a rat model of prostate cancer, and this enhanced the release of cell-free tumor microRNA into the blood circulation. In another study, a chicken embryo tumor model was used to show the feasibility of amplifying the release of extracellular vesicles using HIFU (ultrasound frequency=1.15 MHz and peak to peak pressure was within the range of 10-30 MPa) in combination with phase-change nanodroplets which changed to microbubbles upon HIFU sonication. In a recent study, two protein biomarkers were found to be significantly increased in the plasma of patients undergoing HIFU thermal ablation (ultrasound frequency=1.1 MHz and power of 100-200 W) of uterine fibroids. All these previous studies used HIFU to induce permanent mechanical or thermal disruption of the tumor to enhance the release of tumor biomarkers. The tissue damaging effect limits the application of these techniques as diagnostic tools in a sensitive organ such as the brain. In contrast, the FUS-LBx technique disclosed herein uses low-intensity pulsed FUS, which has the potential advantage of enabling the biomarker release without causing tissue damage. As shown in Example 1, the acoustic pressures used were intentionally selected to be relatively high (1.52-3.53 MPa in mouse model) to increase the chance of success in releasing biomarkers. As expected, hemorrhage was found in the relatively higher intensity FUS-targeted brain area.

Low-intensity focused ultrasound can be used with low acoustic pressures (e.g., less than about 10 MPa), ultrasound frequency less than about 1.5 MHz, peak compressional focal pressure less than about 90 MPa, or peak rarefactional focal pressure less than about 17 MPa. Low-intensity focused ultrasound can be used with a peak to peak pressure less than about 10 to 30 MPa; an ultrasound frequency less than 1.1 MHz; a power of less than about 100 to 200 W; or peak negative acoustic pressure (PNP) levels of less than about 3.53 MPa.

Example 2 describes the effects of FUS acoustic pressure on the level of tumor biomarker release and the extent of associated hemorrhage in order to optimize the FUS-LBx technique. Example 2 determined the optimal ultrasonic pressure for FUS-LBx that can sufficiently increase plasma levels of the tumor biomarkers while at the same time minimize the risk of hemorrhage in the brain. It was further explored whether post-sonication changes in tumor MR contrast enhancement can predict successful biomarker release for the future development of image-guided FUS-LBx technique.

Disclosed herein are systems comprising a FUS-induced BBB opening device that are affordable, high throughput, and can be easily translated for clinical use or dedicated for animal (e.g., pig) or small animal (e.g., mouse) research. The transducer, as described herein can be an inexpensive flat ultrasound transducer coupled to a 3D printed acoustic lens (or acoustic window). The cost of the transducer, as described in the Examples, was about $80, while the FUS transducer commonly used in preclinical research can cost over $2,000. Multiple transducers can be used simultaneously to achieve high throughput treatment of multiple animals at the same time.

A wearable helmet can be used for non-invasive, targeted FUS sonication of the human or animal brain while animals are awake. The helmet can have a modular design, featuring easy removal and installation of the unit for targeting different brain regions.

The performance of the helmet in inducing BBB opening can be assessed by co-injecting Evan's blue with microbubbles to evaluate BBB permeability using fluorescence imaging of ex vivo brain slices in animals.

The helmet and ultrasound transducer and wirings are lightweight at about 6.6 g. The constraint design of the helmet can minimize the effect of mouse movement on targeting. The helmet system achieved localized BBB opening at the targeted brain location. The fluorescence intensity of the Evan's blue in the brains of awake mice was higher than that in anesthetized mice, suggesting that FUS-induced BBB opening was affected by anesthesia.

The helmet design of the FUS device provides an innovative tool to study FUS-induced BBB opening in subjects such as an awake mouse.

As described herein, the FUS system can use acoustic pressures between about 0.1 MPa and about 10 MPa. For example, the acoustic pressure can be about 0.1 MPa; about 0.2 MPa; about 0.3 MPa; about 0.4 MPa; about 0.5 MPa; about 0.6 MPa; about 0.7 MPa; about 0.8 MPa; about 0.9 MPa; about 1 MPa; about 1.1 MPa; about 1.2 MPa; about 1.3

MPa; about 1.4 MPa; about 1.5 MPa; about 1.6 MPa; about 1.7 MPa; about 1.8 MPa; about 1.9 MPa; about 2 MPa; about 2.1 MPa; about 2.2 MPa; about 2.3 MPa; about 2.4 MPa; about 2.5 MPa; about 2.6 MPa; about 2.7 MPa; about 2.8 MPa; about 2.9 MPa; about 3 MPa; about 3.1 MPa; about 3.2 MPa; about 3.3 MPa; about 3.4 MPa; about 3.5 MPa; about 3.6 MPa; about 3.7 MPa; about 3.8 MPa; about 3.9 MPa; about 4 MPa; about 4.1 MPa; about 4.2 MPa; about 4.3 MPa; about 4.4 MPa; about 4.5 MPa; about 4.6 MPa; about 4.7 MPa; about 4.8 MPa; about 4.9 MPa; about 5 MPa; about 5.1 MPa; about 5.2 MPa; about 5.3 MPa; about 5.4 MPa; about 5.5 MPa; about 5.6 MPa; about 5.7 MPa; about 5.8 MPa; about 5.9 MPa; about 6 MPa; about 6.1 MPa; about 6.2 MPa; about 6.3 MPa; about 6.4 MPa; about 6.5 MPa; about 6.6 MPa; about 6.7 MPa; about 6.8 MPa; about 6.9 MPa; about 7 MPa; about 7.1 MPa; about 7.2 MPa; about 7.3 MPa; about 7.4 MPa; about 7.5 MPa; about 7.6 MPa; about 7.7 MPa; about 7.8 MPa; about 7.9 MPa; about 8 MPa; about 8.1 MPa; about 8.2 MPa; about 8.3 MPa; about 8.4 MPa; about 8.5 MPa; about 8.6 MPa; about 8.7 MPa; about 8.8 MPa; about 8.9 MPa; about 9 MPa; about 9.1 MPa; about 9.2 MPa; about 9.3 MPa; about 9.4 MPa; about 9.5 MPa; about 9.6 MPa; about 9.7 MPa; about 9.8 MPa; about 9.9 MPa; or about 10 MPa. Recitation of each of these discrete values is understood to include ranges between each value. Recitation of each range is understood to include discrete values within the range.

As described herein, the FUS system can use a duty cycle between about 0.1% and about 10%. For example, the duty cycle can be about 0.1%; about 0.2%; about 0.3%; about 0.4%; about 0.5%; about 0.6%; about 0.7%; about 0.8%; about 0.9%; about 1%; about 1.1%; about 1.2%; about 1.3%; about 1.4%; about 1.5%; about 1.6%; about 1.7%; about 1.8%; about 1.9%; about 2%; about 2.1%; about 2.2%; about 2.3%; about 2.4%; about 2.5%; about 2.6%; about 2.7%; about 2.8%; about 2.9%; about 3%; about 3.1%; about 3.2%; about 3.3%; about 3.4%; about 3.5%; about 3.6%; about 3.7%; about 3.8%; about 3.9%; about 4%; about 4.1%; about 4.2%; about 4.3%; about 4.4%; about 4.5%; about 4.6%; about 4.7%; about 4.8%; about 4.9%; about 5%; about 5.1%; about 5.2%; about 5.3%; about 5.4%; about 5.5%; about 5.6%; about 5.7%; about 5.8%; about 5.9%; about 6%; about 6.1%; about 6.2%; about 6.3%; about 6.4%; about 6.5%; about 6.6%; about 6.7%; about 6.8%; about 6.9%; about 7%; about 7.1%; about 7.2%; about 7.3%; about 7.4%; about 7.5%; about 7.6%; about 7.7%; about 7.8%; about 7.9%; about 8%; about 8.1%; about 8.2%; about 8.3%; about 8.4%; about 8.5%; about 8.6%; about 8.7%; about 8.8%; about 8.9%; about 9%; about 9.1%; about 9.2%; about 9.3%; about 9.4%; about 9.5%; about 9.6%; about 9.7%; about 9.8%; about 9.9%; or about 10%. Recitation of each of these discrete values is understood to include ranges between each value. Recitation of each range is understood to include discrete values within the range.

As described herein, the FUS system can use a pulse repetition frequency between about 0.1 Hz and about 10 Hz. For example, the pulse repetition frequency can be about 0.1 Hz; about 0.2 Hz; about 0.3 Hz; about 0.4 Hz; about 0.5 Hz; about 0.6 Hz; about 0.7 Hz; about 0.8 Hz; about 0.9 Hz; about 1 Hz; about 1.1 Hz; about 1.2 Hz; about 1.3 Hz; about 1.4 Hz; about 1.5 Hz; about 1.6 Hz; about 1.7 Hz; about 1.8 Hz; about 1.9 Hz; about 2 Hz; about 2.1 Hz; about 2.2 Hz; about 2.3 Hz; about 2.4 Hz; about 2.5 Hz; about 2.6 Hz; about 2.7 Hz; about 2.8 Hz; about 2.9 Hz; about 3 Hz; about 3.1 Hz; about 3.2 Hz; about 3.3 Hz; about 3.4 Hz; about 3.5 Hz; about 3.6 Hz; about 3.7 Hz; about 3.8 Hz; about 3.9 Hz; about 4 Hz; about 4.1 Hz; about 4.2 Hz; about 4.3 Hz; about 4.4 Hz; about 4.5 Hz; about 4.6 Hz; about 4.7 Hz; about 4.8 Hz; about 4.9 Hz; about 5 Hz; about 5.1 Hz; about 5.2 Hz; about 5.3 Hz; about 5.4 Hz; about 5.5 Hz; about 5.6 Hz; about 5.7 Hz; about 5.8 Hz; about 5.9 Hz; about 6 Hz; about 6.1 Hz; about 6.2 Hz; about 6.3 Hz; about 6.4 Hz; about 6.5 Hz; about 6.6 Hz; about 6.7 Hz; about 6.8 Hz; about 6.9 Hz; about 7 Hz; about 7.1 Hz; about 7.2 Hz; about 7.3 Hz; about 7.4 Hz; about 7.5 Hz; about 7.6 Hz; about 7.7 Hz; about 7.8 Hz; about 7.9 Hz; about 8 Hz; about 8.1 Hz; about 8.2 Hz; about 8.3 Hz; about 8.4 Hz; about 8.5 Hz; about 8.6 Hz; about 8.7 Hz; about 8.8 Hz; about 8.9 Hz; about 9 Hz; about 9.1 Hz; about 9.2 Hz; about 9.3 Hz; about 9.4 Hz; about 9.5 Hz; about 9.6 Hz; about 9.7 Hz; about 9.8 Hz; about 9.9 Hz; or about 10 Hz. Recitation of each of these discrete values is understood to include ranges between each value. Recitation of each range is understood to include discrete values within the range.

As described herein, the FUS system can use an exposure duration between about 1 second and about 20 minutes. For example, the exposure duration can be about 30 s; about 1 min; about 2 min; about 3 min; about 4 min; about 5 min; about 6 min; about 7 min; about 8 min; about 9 min; about 10 min; about 11 min; about 12 min; about 13 min; about 14 min; about 15 min; about 16 min; about 17 min; about 18 min; about 19 min; or about 20 min. Recitation of each of these discrete values is understood to include ranges between each value. Recitation of each range is understood to include discrete values within the range.

As described herein, a biological sample can be collected at any time prior to or after FUS. For example, the sample collection can correspond with a time less than the half-life of the biomarker to be tested. As another example, biological samples can be serially collected at various time points before or after FUS. As another example, the biological sample can be collected within 10 minutes to about 2 days after FUS exposure or administration. For example, the biological sample can be collected post-FUS at about 1 min, about 2 min; about 3 min; about 4 min; about 5 min; about 6 min; about 7 min; about 8 min; about 9 min; about 10 min; about 11 min; about 12 min; about 13 min; about 14 min; about 15 min; about 16 min; about 17 min; about 18 min; about 19 min; or about 20 min. Recitation of each of these discrete values is understood to include ranges between each value. Recitation of each range is understood to include discrete values within the range.

As described herein, the system can be used for any subject with a central nervous system and a blood brain barrier. For example, the subject can be an animal subject, including a mammal, such as horses, cows, dogs, cats, sheep, pigs, mice, rats, monkeys, hamsters, guinea pigs, and chickens, and humans. As another example, the subject can be a human subject.

Biological Sample

The methods and systems designed herein can release biomarkers or genetic material from a brain into a biological sample, such as a biological fluid. The biological fluid or biological sample can be whole blood, blood, plasma, serum, cerebral spinal fluid (CSF), or interstitial fluid (ISF).

Microbubbles

The methods described herein can comprise the use of microbubbles. Microbubbles are widely used for the heart and liver. Microbubbles are commercially available (e.g., Definity®). Microbubbles can be used with FUS to provide lower levels of US intensity with similar results to high-intensity US with less potential side effects or damage. Use of microbubbles, generally, is well known; see e.g. Blomley et al. (2001) "Science, medicine, and the future:

Microbubble contrast agents: A new era in ultrasound" BMJ 322 (7296): 1222-5; Sirsi et al. 2009 Bubble Sci Eng Technol 1(1-2): 3-17. Except as otherwise noted herein, therefore, the process of the present disclosure can be carried out in accordance with such processes.

Microbubbles can be administered by methods currently known in the art. As described herein, the microbubbles are administered according to the clinical dose currently used in treatments (e.g., for Definity® microbubbles, 1.3 mL from a diluted vial is diluted with 8.7 mL saline).

Microbubbles are small, gas-filled bubbles, which can be between 0.5 µm and 10 µm in diameter. Microbubbles are widely used as contrast agents in medical imaging and as carriers for targeted drug delivery. The core of the microbubble is a gas, which is surrounded by a shell that can be composed of polymers, lipids, lipopolymers, proteins, surfactants, or a combination of these.

Microbubbles can be injected intravenously, a process that researchers have shown is safe compared to the use of conventional contrast agents in techniques such as magnetic resonance imaging and radiography.

Microbubbles resonate in an ultrasound beam, contracting and expanding as pressure changes occur in the ultrasound wave. Microbubbles resonate particularly vigorously at the high frequencies used in ultrasound scans (they reflect these strong waves significantly more effectively than body tissues do). Since they are approximately the same size as red blood cells, they exhibit similar rheology in blood vessels and are used to measure blood flow in organs and tumors.

Conventionally, microbubbles have been used for drug delivery in the treatment of cancer. More recently, microbubbles have been used for molecular imaging and targeted gene delivery. It is believed that this is the first reporting of microbubbles being used to facilitate the release of biomarkers or genetic material across the blood brain barrier (BBB).

Microbubbles can be any microbubbles known in the art. For example, the microbubbles can be commercially available microbubbles, such as Definity® microbubbles or phase-change nanodroplets. For example, GE Healthcare makes Optison, a Food and Drug Administration (FDA)-approved microbubble. Optison has an albumin shell and octafluoropropane gas core. Lantheus makes Definity®, which is a FDA-approved microbubble. In Definity®, perflutren lipid microspheres are composed of octafluoropropane encapsulated in an outer lipid shell. Bracco makes Lumason (SonoVue in other countries) which is also FDA-approved. Lumason is a sulfur hexafluoride containing lipid-encapsulated microbubble.

Microbubbles can be used as described herein, but the use of microbubbles is not required to achieve the opening of the BBB and release of biomarkers or genetic information from a brain lesion or tumor.

Biomarker Detection, Genetic Testing, and Genetic Sequencing

Described herein are systems and methods for releasing biomarkers or genetic material from a brain into a biological sample for detection. Detection of these biomarkers can be used to diagnose or treat a subject or to formulate a personalized treatment plan. The presence or absence of such biomarkers or genetic material has implications on clinical decision-making in standard clinical care.

Described herein is the use of qPCR to detect mRNA, but any method of detecting genetic material or biomarkers known in the art can be used. It was also shown that brain-specific biomarkers were released following FUS to the brain (see e.g., Example 3).

The disclosed systems and methods can be used to detect already known biomarkers for a disease or discover new biomarkers in subjects diagnosed with a disease.

Biomarkers, such as RNA or DNA, can have a short half-life. As such, the period of time for the biological sample collection can be from about 1 minute to about 5 minutes or more after FUS is applied to the brain or a portion of the brain. For example, a sample can be collected before FUS, during FUS, or after FUS. As another example, the time after FUS application to collect a biological sample can be about 1 min, about 2 min; about 3 min; about 4 min; about 5 min; about 6 min; about 7 min; about 8 min; about 9 min; about 10 min; about 11 min; about 12 min; about 13 min; about 14 min; about 15 min; about 16 min; about 17 min; about 18 min; about 19 min; or about 20 min. A biological sample can be collected any time before the BBB closes. Recitation of each of these discrete values is understood to include ranges between each value. Recitation of each range is understood to include discrete values within the range.

A biological sample can be collected before FUS and after FUS to measure the biomarkers. Biomarkers can be detected to monitor a course of treatment or to monitor disease progression.

Widely-validated biomarkers that can be detected in a biological sample after FUS treatment can include (i) MGMT promoter methylation as a prognostic and predictive marker in glioblastoma; (ii) co-deletion of 1p and 19q differentiating oligodendrogliomas from astrocytomas; (iii) IDH1/2 mutations; or (iv) select pathway-associated mutations.

Biomarkers detected (with corresponding diseases presently known to be relevant for these biomarkers) can be: co-deletion 1p/19q (Oligodendrogliomas); MGMT promoter methylation (Glioblastomas, anaplastic astrocytomas); IDH 1/2 mutation (Oligo- and astrocytomas WHO grade II and Ill, secondary GBM); EGFRvIII (Glioblastomas); TERT mutation (Gliomas); ATRX mutations (Gliomas); TP53 mutations (Astrocytomas); BRAF V600 mutation (PXA, pilocytic astrocytomas, gangliogliomas); BRAF/KIAA1549 fusion (Pilocytic astrocytomas); H3.3 histones (Pediatric HGG); SHH pathway mutations (such as MYCN amplification, GLI2 amplification, or TP53 mutations) (Medulloblastomas); WNT pathway mutations (Medulloblastomas); or MYC (Medulloblastomas).

Detecting biomarkers of brain tumors in biological samples is well known in the art (see e.g., Staedtke et al. (2016) "Actionable Molecular Biomarkers in Primary Brain Tumors" Trends in Cancer 2(7) 338-349). Except as otherwise noted herein, therefore, the process of detecting biomarkers of the present disclosure can be carried out in accordance with such processes.

Detecting biomarkers (e.g., DNA, RNA, cell-free RNA, cell-free DNA) of neurodegenerative disease in biological samples is well known in the art (see e.g., Jeromin et al. (2017) Adv Neurobiol 15 491-528; Beach 217 Neurol Ther. 6(Supp 1)5-13). Except as otherwise noted herein, therefore, the process of detecting biomarkers of the present disclosure can be carried out in accordance with such processes.

As an example, the presently disclosed systems and methods can be used for detecting or discovering biomarkers for Alzheimer's disease (AD) (e.g., AR, tau, phosphorylated tau, other neuronal proteins), Parkinson's disease (PD) (e.g., alpha-synuclein), or amyotrophic lateral sclerosis (ALS).

Detecting biomarkers of neurological or neurodegenerative diseases, disorders, or conditions in biological samples are well known in the art (see e.g., Smith 2017 Biomarkers on the brain: Putting biomarkers together for a better understanding of the nervous system, Science, special technology feature; Jain 2015 Biomarkers in Neurology, MedLink). Except as otherwise noted herein, therefore, the process of the present disclosure can be carried out in accordance with such processes.

Detection and discovery of brain biomarkers can track disease progression over time and correlate with known clinical measures; detect the effect or efficacy of a drug; or serve as a surrogate endpoint in clinical trial.

Liquid Brain Biopsy

Described herein are methods and systems for blood-based liquid biopsies of the brain. The liquid brain biopsy can be used to detect genetic material from the brain from various central nervous system (CNS cancers or tumors or neurological or neurodegenerative diseases, disorders, or conditions). The disclosed methods and systems can reach lesions previously unreachable by traditional biopsy techniques. Furthermore, the disclosed systems and methods can be performed repeatedly for use in monitoring the lesion, treatment response, or treatment efficacy. The disclosed systems and methods can also be useful for diagnosing lesions or detecting biomarkers in areas of the brain or CNS that are typically not available for biopsy or surgery, such as the brain stem.

Previous methods for FUS on the brain focused on drug-delivery ("one-way trafficking"). Here, it was discovered that FUS-mediated BBB disruption enhances "two-way trafficking" between brain and blood.

Central nervous system (CNS) tumors are significant causes of cancer morbidity and mortality, especially in children and young adults where they account for ~20-30% of cancer deaths. Noninvasive neuroimaging modalities (e.g., magnetic resonance imaging (MRI), and computerized tomography (CT)) are used to evaluate tumor lesions, but observed changes, especially after treatment, can be difficult to interpret. Surgical resection or stereotactic biopsy is typically performed for histologic confirmation and increasingly for genetic profiling. However, tissue biopsy requires brain surgery and can be associated with adverse effects such as hemorrhage and infection. Repeated tumor biopsies that may be needed for tracking tumor evolution, treatment response, and tumor recurrence are often not feasible. Furthermore, tissue biopsies may be challenging when tumors are located at difficult locations or patients are too ill to tolerate invasive procedures.

Noninvasive blood-based liquid biopsies are a rapidly emerging strategy to provide genetic tumor profiling that can be used for treatment selection, treatment monitoring, residual disease detection, and asymptomatic individual screening. Some success has been achieved in integrating blood-based liquid biopsy into the routine clinical diagnostics. However, limited progress has been made for brain tumors. Although several groups have reported biomarker detection in the cerebrospinal fluid (CSF) of patients with brain tumors, obtaining CSF via lumbar puncture remains an invasive procedure and can be unsafe in some settings. Blood-based liquid biopsies are noninvasive, but there remain multiple hurdles for their application in the brain. First, the blood-brain barrier (BBB) restricts the release of large molecules such as DNA and RNA from the tumor to the peripheral circulation. Even though partial BBB disruption is a core feature of glioblastoma (the most common type of high-grade glioma) at the late stage of the tumors, the BBB remains intact in the early stage and the low-grade diffuse gliomas. Second, brain tumors, especially glioblastomas, are heterogeneous with spatially distinct molecular profiling. Localization of tumor areas that harbor specific mutations is not possible using conventional methods of liquid biopsy, as these methods are inherently spatially agnostic. Third, many tumor markers, such as some cell-free RNAs and DNAs, have short half-lives in blood. Detection of these biomarkers can be enhanced by stimulating their release from the tumor to the circulation and precisely controlling the blood-collection time to be shorter than their lifetimes in the blood. Therefore, the disclosed noninvasive, spatially resolved, and temporally controlled liquid biopsy technique is in great need to improve the clinical care of patients with any neurological or neurodegenerative disease, disorder, or condition (e.g., CNS tumors).

Central Nervous System (CNS) Cancer/Tumors

The presently disclosed methods can be used to detect or discover biomarkers for central nervous system (CNS) cancers or tumors. CNS cancers can include a brain or spinal cord cancer or tumor.

The brain or spinal cord cancer or tumor detected can be acoustic neuroma; astrocytoma; atypical teratoid rhaboid tumor (ATRT); brain stem glioma; chordoma; chondrosarcoma; choroid plexus; CNS lymphoma; craniopharyngioma; cysts; ependymoma; ganglioglioma; germ cell tumor; glioblastoma (GBM); glioma; hemangioma; juvenile pilocytic astrocytoma (JPA); lipoma; lymphoma; medulloblastoma; meningioma; metastatic brain tumor; neurilemmomas; neurofibroma; neuronal & mixed neuronal-glial tumors; non-hodgkin lymphoma; oligoastrocytoma; oligodendroglioma; optic nerve glioma; pineal tumor; pituitary tumor; primitive neuroectodermal (PNET); rhabdoid tumor; or schwannoma.

The astrocytoma can be a grade I pilocytic astrocytoma, a grade II—low-grade astrocytoma, a grade III anaplastic astrocytoma, a grade IV glioblastoma (GBM), or a juvenile pilocytic astrocytoma.

The glioma can be a brain stem glioma, an ependymoma, a mixed glioma, an optic nerve glioma, or a subependymoma.

Depending on the marker, treatment of CNS cancers or tumors can comprise the administration of PCV, temozolomide, IDH1/2inhibitors, Immunotherapeutic approaches (e.g., vaccines, CAR T-cells), BRAF inhibitors, MEK inhibitors, Epigenetic inhibitors, JMJD3 inhibitor, SMO inhibitors, reduced dose of RT, chemotherapy or combination, Gemcitabine and pemetrexed, or BET bromodomain inhibitors (see e.g., Staedtke et al. (2016) "Actionable Molecular Biomarkers in Primary Brain Tumors" Trends in Cancer 2(7) 338-349).

Neurological or Neurodegenerative Diseases, Disorders, or Conditions

These disclosed methods and system can also be used to detect or discover biomarkers for other neurological disease states. For example, the methods and systems can be used in subjects having or suspected of having a neurological disease, disorder, or condition such as Abulia; Agraphia; Alcoholism; Alexia; Alien hand syndrome; Allan-Herndon-Dudley syndrome; Alternating hemiplegia of childhood; Alzheimer's disease; Amaurosis fugax; Amnesia; Amyotrophic lateral sclerosis (ALS); Aneurysm; Angelman syndrome; Anosognosia; Aphasia; Apraxia; Arachnoiditis; Arnold-Chiari malformation; Asomatognosia; Asperger syndrome; Ataxia; Attention deficit hyperactivity disorder; ATR-16 syndrome; Auditory processing disorder; Autism spectrum; Behcets disease; Bipolar disorder; Bell's palsy; Brachial plexus injury; Brain damage; Brain injury; Brain tumor; Brody myopathy; Canavan disease; Capgras delusion; Carpal tunnel syndrome; Causalgia; Central pain syndrome; Central pontine myelinolysis; Centronuclear myopathy; Cephalic disorder; Cerebral aneurysm; Cerebral arteriosclerosis; Cerebral atrophy; Cerebral autosomal dominant arteriopathy with subcortical infarcts and leukoencephalopathy (CADASIL); Cerebral dysgenesis-neuropathy-ichthyosis-keratoderma syndrome (CEDNIK syndrome); Cerebral gigantism; Cerebral palsy; Cerebral vasculitis; Cervical spinal stenosis; Charcot-Marie-Tooth disease; Chiari malformation; Chorea; Chronic fatigue syndrome; Chronic inflammatory demyelinating polyneuropathy (CIDP); Chronic pain; Cockayne syndrome; Coffin-Lowry syndrome; Coma; Complex regional pain syndrome; Compression neuropathy; Congenital facial diplegia; Corticobasal degeneration; Cranial arteritis; Craniosynostosis; Creutzfeldt-Jakob disease; Cumulative trauma disorders; Cushing's syndrome; Cyclothymic disorder; Cyclic Vomiting Syndrome (CVS); Cytomegalic inclusion body disease (CIBD); Cytomegalovirus Infection; Dandy-Walker syndrome; Dawson disease; De Morsier's syndrome; Dejerine-Klumpke palsy; Dejerine-Sottas disease; Delayed sleep phase syndrome; Dementia; Dermatomyositis; Developmental coordination disorder; Diabetic neuropathy; Diffuse sclerosis; Diplopia; Disorders of consciousness; Down syndrome; Dravet syndrome; Duchenne muscular dystrophy; Dysarthria; Dysautonomia; Dyscalculia; Dysgraphia; Dyskinesia; Dyslexia; Dystonia; Empty sella syndrome; Encephalitis; Encephalocele; Encephalotrigeminal angiomatosis; Encopresis; Enuresis; Epilepsy; Epilepsy-intellectual disability in females; Erb's palsy; Erythromelalgia; Essential tremor; Exploding head syndrome; Fabry's disease; Fahr's syndrome; Fainting; Familial spastic paralysis; Febrile seizures; Fisher syndrome; Friedreich's ataxia; Fibromyalgia; Foville's syndrome; Fetal alcohol syndrome; Fragile X syndrome; Fragile X-associated tremor/ataxia syndrome (FXTAS); Gaucher's disease; Generalized epilepsy with febrile seizures plus; Gerstmann's syndrome; Giant cell arteritis; Giant cell inclusion disease; Globoid Cell Leukodystrophy; Gray matter heterotopia; Guillain-Barré syndrome; Generalized anxiety disorder; HTLV-1 associated myelopathy; Hallervorden-Spatz syndrome; Head injury; Headache; Hemifacial Spasm; Hereditary Spastic Paraplegia; Heredopathia atactica polyneuritiformis; Herpes zoster oticus; Herpes zoster; Hirayama syndrome; Hirschsprung's disease; Holmes-Adie syndrome; Holoprosencephaly; Huntington's disease; Hydranencephaly; Hydrocephalus; Hypercortisolism; Hypoxia; Immune-Mediated encephalomyelitis; Inclusion body myositis; Incontinentia pigmenti; Infantile Refsum disease; Infantile spasms; Inflammatory myopathy; Intracranial cyst; Intracranial hypertension; Isodicentric 15; Joubert syndrome; Karak syndrome; Kearns-Sayre syndrome; Kinsbourne syndrome; Kleine-Levin syndrome; Klippel Feil syndrome; Krabbe disease; Kufor-Rakeb syndrome; Lafora disease; Lambert-Eaton myasthenic syndrome; Landau-Kleffner syndrome; Lateral medullary (Wallenberg) syndrome; Learning disabilities; Leigh's disease; Lennox-Gastaut syndrome; Lesch-Nyhan syndrome; Leukodystrophy; Leukoencephalopathy with vanishing white matter; Lewy body dementia; Lissencephaly; Locked-in syndrome; Lou Gehrig's disease (See amyotrophic lateral sclerosis); Lumbar disc disease; Lumbar spinal stenosis; Lyme disease—Neurological Sequelae; Machado-Joseph disease (Spinocerebellar ataxia type 3); Macrencephaly; Macropsia; Mal de debarquement; Megalencephalic leukoencephalopathy with subcortical cysts; Megalencephaly; Melkersson-Rosenthal syndrome; Menieres disease; Meningitis; Menkes disease; Metachromatic leukodystrophy; Microcephaly; Micropsia; Migraine; Miller Fisher syndrome; Mini-stroke (transient ischemic attack); Misophonia; Mitochondrial myopathy; Mobius syndrome; Monomelic amyotrophy; Morvan syndrome; Motor Neuron Disease—see amyotrophic lateral sclerosis; Motor skills disorder; Moyamoya disease; Mucopolysaccharidoses; Multi-infarct dementia; Multifocal motor neuropathy; Multiple sclerosis; Multiple system atrophy; Muscular dystrophy; Myalgic encephalomyelitis; Myasthenia gravis; Myelinoclastic diffuse sclerosis; Myoclonic Encephalopathy of infants; Myoclonus; Myopathy; Myotubular myopathy; Myotonia congenita; Narcolepsy; Neuro-Behget's disease; Neurofibromatosis; Neuroleptic malignant syndrome; Neurological manifestations of AIDS; Neurological sequelae of lupus; Neuromyotonia; Neuronal ceroid lipofuscinosis; Neuronal migration disorders; Neuropathy; Neurosis; Niemann-Pick disease; Non-24-hour sleep-wake disorder; Nonverbal learning disorder; O'Sullivan-McLeod syndrome; Occipital Neuralgia; Occult Spinal Dysraphism Sequence; Ohtahara syndrome; Olivopontocerebellar atrophy; Opsoclonus myoclonus syndrome; Optic neuritis; Orthostatic Hypotension; Otosclerosis; Overuse syndrome; Palinopsia; Paresthesia; Parkinson's disease; Paramyotonia congenita; Paraneoplastic diseases; Paroxysmal attacks; Parry-Romberg syndrome; PANDAS; Pelizaeus-Merzbacher disease; Periodic paralyses; Peripheral neuropathy; Pervasive developmental disorders; Phantom limb/Phantom pain; Photic sneeze reflex; Phytanic acid storage disease; Pick's disease; Pinched nerve; Pituitary tumors; PMG; Polyneuropathy; Polio; Polymicrogyria; Polymyositis; Porencephaly; Post-polio syndrome; Postherpetic neuralgia (PHN); Postural hypotension; Prader-Willi syndrome; Primary lateral sclerosis; Prion diseases; Progressive hemifacial atrophy; Progressive multifocal leukoencephalopathy; Progressive supranuclear palsy; Prosopagnosia; Pseudotumor cerebri; Quadrantanopia; Quadriplegia; Rabies; Radiculopathy; Ramsay Hunt syndrome type I; Ramsay Hunt syndrome type II; Ramsay Hunt syndrome type III—see Ramsay-Hunt syndrome; Rasmussen encephalitis; Reflex neurovascular dystrophy; Refsum disease; REM sleep behavior disorder; Repetitive stress injury; Restless legs syndrome; Retrovirus-associated myelopathy; Rett syndrome; Reye's syndrome; Rhythmic Movement Disorder; Romberg syndrome; Saint Vitus dance; Sandhoff disease; Schilder's disease (two distinct conditions); Schizencephaly; Sensory processing disorder; Septo-optic dysplasia; Shaken baby syndrome; Shingles; Shy-Drager syndrome; Sjögren's syndrome; Sleep apnea; Sleeping sickness; Snatiation; Sotos syndrome; Spasticity; Spina bifida; Spinal cord injury; Spinal cord tumors; Spinal muscular atrophy; Spinal and bulbar muscular atrophy; Spinocerebellar ataxia; Split-brain; Steele-Richardson-Olszewski syndrome; Stiff-person syndrome; Stroke; Sturge-Weber syndrome; Stuttering; Subacute sclerosing panencephalitis; Subcortical arteriosclerotic encephalopathy; Superficial siderosis; Sydenham's chorea; Syncope; Synesthesia; Syringomyelia; Tarsal tunnel syndrome; Tardive dyskinesia; Tardive dysphrenia; Tarlov cyst; Tay-Sachs disease; Temporal arteritis; Temporal lobe epilepsy; Tetanus; Tethered spinal cord syndrome; Thomsen disease; Thoracic outlet syndrome; Tic Douloureux; Todd's paralysis; Tourette syndrome; Toxic encephalopathy; Transient ischemic attack; Transmissible spongiform encephalopathies; Transverse myelitis; Traumatic brain injury; Tremor; Trichotillomania; Trigeminal neuralgia; Tropical spastic paraparesis; Trypanosomiasis; Tuberous sclerosis; 22q13 deletion syndrome; Unverricht-Lundborg disease; Vestibular schwannoma (Acoustic neuroma); Von Hippel-Lindau disease (VHL); Viliuisk Encephalomyelitis (VE); Wallenberg's syndrome; West syndrome; Whiplash; Williams syndrome; Wilson's disease; Y-Linked Hearing Impairment; or Zellweger syndrome.

For example, the methods and systems can be used in subjects having or suspected of having a neurological disease, disorder, or condition comprising a neurodegenerative disease, disorder, or condition. As an example, a neurodegenerative disease, disorder or condition can be Alzheimer's disease, amyotrophic lateral sclerosis (ALS), Alexander disease, Alpers' disease, Alpers-Huttenlocher syndrome, alpha-methylacyl-CoA racemase deficiency, Andermann syndrome, Arts syndrome, ataxia neuropathy spectrum, ataxia (E.g., with oculomotor apraxia, autosomal dominant cerebellar ataxia, deafness, and narcolepsy), autosomal recessive spastic ataxia of Charlevoix-Saguenay, Batten disease, beta-propeller protein-associated neurodegeneration, Cerebro-Oculo-Facio-Skeletal Syndrome (COFS), Corticobasal Degeneration, CLN1 disease, CLN10 disease, CLN2 disease, CLN3 disease, CLN4 disease, CLN6 disease, CLN7 disease, CLN8 disease, cognitive dysfunction, congenital insensitivity to pain with anhidrosis, dementia, familial encephalopathy with neuroserpin inclusion bodies, familial British dementia, familial Danish dementia, fatty acid hydroxylase-associated neurodegeneration, Gerstmann-Straussler-Scheinker Disease, GM2-gangliosidosis (e.g., AB variant), HMSN type 7 (e.g., with retinitis pigmentosa), Huntington's disease, infantile neuroaxonal dystrophy, infantile-onset ascending hereditary spastic paralysis, Huntington's disease (HD), infantile-onset spinocerebellar ataxia, juvenile primary lateral sclerosis, Kennedy's disease, Kuru, Leigh's Disease, Marinesco-Sjögren syndrome, Mild Cognitive Impairment (MCI), mitochondrial membrane protein-associated neurodegeneration, Motor neuron disease, Monomelic Amyotrophy, Motor neuron diseases (MND), Multiple System Atrophy, Multiple System Atrophy with Orthostatic Hypotension (Shy-Drager Syndrome), multiple sclerosis, multiple system atrophy, neurodegeneration in Down's syndrome (NDS), neurodegeneration of aging, Neurodegeneration with brain iron accumulation, neuromyelitis optica, pantothenate kinase-associated neurodegeneration, Opsoclonus Myoclonus, prion disease, Progressive Multifocal Leukoencephalopathy, Parkinson's disease (PD), PD-related disorders, polycystic lipomembranous osteodysplasia with sclerosing leukoencephalopathy, prion disease, progressive external ophthalmoplegia, riboflavin transporter deficiency neuronopathy, Sandhoff disease, Spinal muscular atrophy (SMA), Spinocerebellar ataxia (SCA), Striatonigral degeneration, Transmissible Spongiform Encephalopathies (Prion Diseases), or Wallerian-like degeneration.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Focused Ultrasound-Enabled Brain Tumor Liquid Biopsy

The following example describes the detection of a glioblastoma biomarker (mRNA) in an animal model.

Although blood-based liquid biopsies have emerged as a promising non-invasive method to detect biomarkers in various cancers, limited progress has been made for brain tumors. One major obstacle is the blood-brain barrier (BBB), which hinders efficient passage of tumor biomarkers into the peripheral circulation. The objective of this study was to determine whether FUS in combination with microbubbles can enhance the release of biomarkers from the brain tumor to the blood circulation. Two glioblastoma tumor models (U87 and GL261), developed by intracranial injection of respective enhanced green fluorescent protein (eGFP)-transduced glioblastoma cells, were treated by FUS in the presence of systemically injected microbubbles. Effect of FUS on plasma eGFP mRNA levels was determined using quantitative polymerase chain reaction. eGFP mRNA were only detectable in the FUS-treated U87 mice and undetectable in the untreated U87 mice (maximum cycle number set to 40). This finding was replicated in GL261 mice across three different acoustic pressures. The circulating levels of eGFP mRNA were 1,500-4,800 fold higher in the FUS-treated GL261 mice than that of the untreated mice for the three acoustic pressures. This study demonstrated the feasibility of FUS-enabled brain tumor liquid biopsies in two different murine glioma models across different acoustic pressures.

Introduction

Mutations in the DNA, changes in epigenomic makeup, and variations in gene expression associated with brain tumors can inform clinical practice by providing invaluable information for diagnosis, prognostication, disease monitoring, and development of personalized treatment strategies[1]. Such molecular biomarkers, which can be examined in surgical resection or biopsy specimens, are becoming an integral component of clinical practice[2]. However, direct surgical tissue biopsy to determine tumor molecular profiles is associated with potential complications such as hemorrhage and infection[3]. Furthermore, repeated tissue biopsies using surgical interventions to assess treatment response and recurrence may not be feasible given the increased risk for complications and morbidity, especially for brain tumors. Liquid biopsy offers a noninvasive approach for detecting circulating molecular biomarkers.

Although liquid biopsy has been established in clinical care of patients with various cancer types[4], limited progress has been made for brain tumors[2]. For brain tumor liquid biopsy, the major challenge is the hindrance of tumor biomarker release into the bloodstream by the blood-brain barrier (BBB)[5]. Even though the BBB is partially disrupted in the core part of glioblastoma (the most common type of high-grade glioma), it remains intact in large parts of glioblastoma and lower grade diffuse gliomas, which may prevent the efficient passage of biomarkers into the blood circulation. In line with this, circulating tumor DNA (ctDNA) was reported to be detectable in a small fraction of patients with advanced gliomas (<10%) as compared to patients with other solid tumors[6]. It has also been shown that patients with high-grade glioma have a significantly higher plasma DNA concentration than patients with low-grade gliomas. These suggest that the increased permeability of BBB associated with the progression of gliomas is correlated with the release of biomarkers from the tumor to the blood[7]. It was also found that although D-2-hydroxyglutarate (D2HG) levels have been used in the clinic for the diagnosis and monitoring of patients with IDH1/2-mutant malignancies, D2HG plasma levels in patients with IDH2/2-mutant gliomas are within the normal range, suggesting that the BBB prevents D2HG from entering the blood circulation[8]. Therefore, approaches that can non-invasively enhance the release of biomarkers from the brain tumors to the blood circulation would be of significant clinical relevance.

Focused ultrasound (FUS) offers noninvasive and spatially-localized biomarker release into the blood stream[3,9]. The initial concept for blood biomarker amplification and localization using ultrasound was proposed in a study published in 2009, which demonstrated the feasibility to enhance the release of protein biomarkers from a colon cancer cell line in both ex vivo cell cultures and an in vivo mouse tumor model[10]. Building on this initial work, in vitro cell culture studies showed the feasibility of enhancing mRNA biomarker release from a breast cancer cell line using microbubble-enhanced ultrasound[11], and the feasibility of releasing a combination of ovarian cancer biomarkers using ultrasound[12]. Two recent in vivo studies further demonstrated that ultrasound-mediated release of biomarkers into the bloodstream is a promising approach for detecting tumor biomarkers via blood sampling[10,13,14]. In one of the studies, a chicken embryo tumor model was used to show the feasibility of amplifying the release of extracellular vesicles using high-intensity focused ultrasound (HIFU) in combination with phase-change nanodroplets which changed to microbubbles upon HIFU sonication[14]. In the other study, pulsed HIFU with high acoustic pressures was used to induce histotripsy (i.e., a technique for mechanical tissue fractionation) in a rat model of prostate cancer, and this enhanced release of cell-free tumor microRNA into the blood circulation[13]. Although promising, these findings cannot be readily extended to applications in the brain, given challenges inherent to the brain: first, delivery of acoustic energy to the brain is impeded by attenuation and distortion of acoustic waves by the skull; second, biomarker release from the brain is inherently limited by the presence of the BBB.

FUS in combination with microbubbles has been studied extensively for inducing BBB opening for noninvasive and localized delivery of drugs in the blood circulation to the brain parenchyma[15-17]. Many studies have been performed to optimize the treatment parameters[18-20] and evaluate the short-term and long-term safety profiles[21-24]. Ongoing clinical trials are evaluating the feasibility and safety of FUS-induced BBB opening in patients with glioblastoma and Alzheimer's disease[25,26]. Although all previous studies focused on exploring the utility of FUS-induced BBB as a means of targeted delivery of circulating therapeutics, here, it was hypothesized that FUS-mediated BBB disruption could be viewed as a tool for enhancing "two-way trafficking" between brain and blood. While circulating molecules can be allowed to enter the brain using FUS-mediated BBB disruption, brain biomarkers (e.g., tumor markers) can also be released into the blood circulation for liquid biopsies. Here is disclosed the development of an FUS-enabled brain tumor liquid biopsy technique, which uses FUS in combination with microbubbles to enhance the release of biomarkers from brain tumors into the blood circulation for liquid biopsies.

The feasibility of using FUS in combination with microbubbles was demonstrated for the local release of mRNA from glioblastoma tumors in mice into the bloodstream for liquid biopsies. Glioblastoma was selected as the tumor model because it is the most frequent type of primary brain cancer in adults and associated with a dismal prognosis[27]. The biomarker used was enhanced green fluorescent protein (eGFP) mRNA, which was highly specific to the tumor models used in this study, as the tumor models were established by the direct injection of eGFP-luciferase-transduced glioblastoma cells into the mouse brain. Both human glioma U87 cells and murine glioma GL261 cells were used to develop two mouse models of glioblastoma.

Results

FUS-Enabled Liquid Biopsy in an Orthotopic Human Glioma Xenograft Model

An orthotopic mouse model developed by implantation of eGFP-luciferase-transduced human glioma cells (U87) into the brains of nude mice was treated by an ultrasound imaging-guided FUS system (see e.g., FIG. 1A). Local growth of the tumors within the brain was assessed by monitoring luciferase activity using bioluminescent imaging (BLI) and verified using fluorescence imaging of the ex vivo brain slices (see e.g., FIG. 1B). The focus of the FUS transducer (frequency=1.5 MHz) was targeted at the tumor based on the tumor location identified by the BLI. The acoustic pressure of the FUS pulses was 3.28 MPa and other parameters were similar to those used for the BBB disruption (duty cycle of 1%, pulse repetition frequency of 1 Hz, and exposure duration of 2 min) (see e.g., FIG. 1E)[20-24]. The experimental timeline is shown in FIG. 1F. For the U87 mice, terminal (non-survival) blood collection via cardiac puncture was performed immediately (~4 minutes) after FUS treatment. Such a short interval was selected in reference to a recent observation showing shorter collection time after FUS treatment was associated with higher RNA yield[13].

Figures 2A, 2B, 2C:
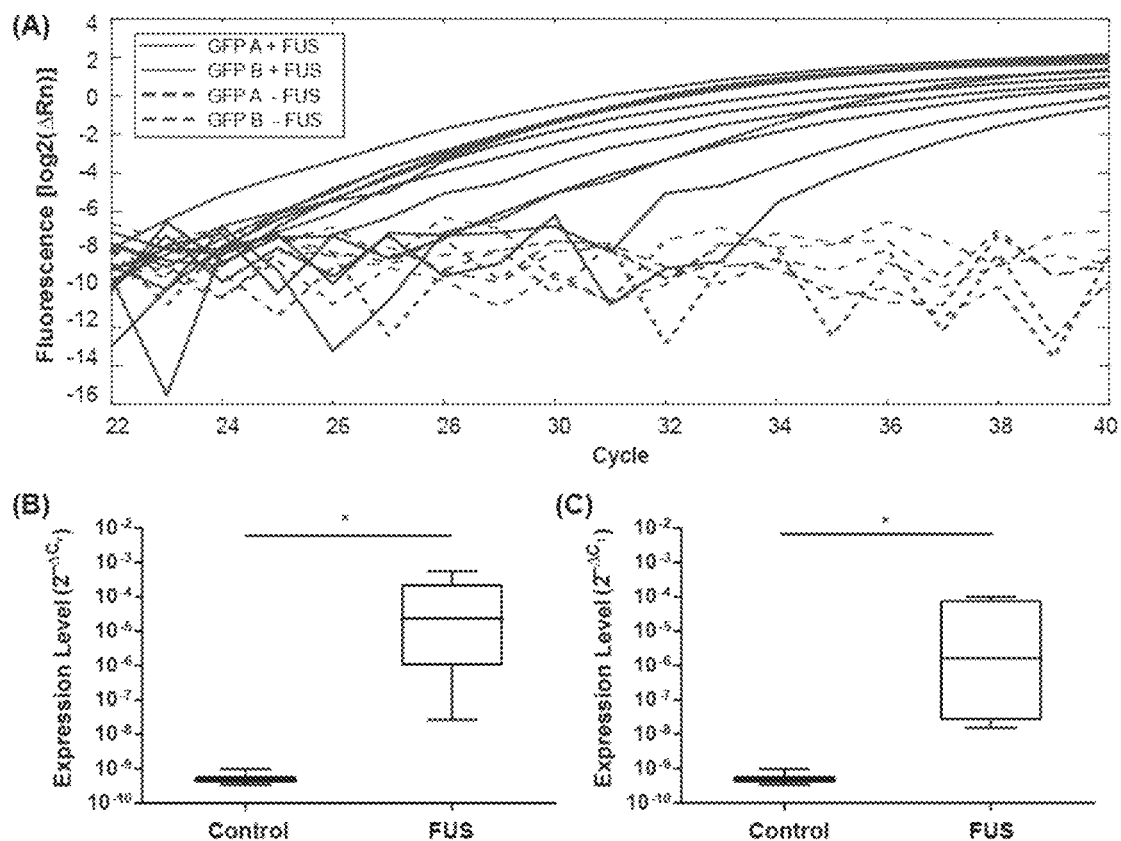
FIG. 2A-FIG. 2C. Comparison of the circulating eGFP mRNA expression in the control and treated U87 mice. (A) Amplification curves [$\log_2(\Delta Rn)$] of circulating eGFP mRNA in the control (n=3) and treated mice (n=6) for two primer pairs, eGFP A and eGFP B. $\Delta Rn$ is the fluorescence intensity of eGFP mRNA minus the baseline. Comparison of the relative expression levels ($2^{-\Delta C_T}$) of (B) eGFP A and (C) eGFP B in the control and treated mice. *: p<0.05

Quantitative polymerase chain reaction (qPCR) was performed to determine relative circulating levels of eGFP mRNA (target biomarker) normalized to 5.8S rRNA (internal control) in blood serum. Two pairs of PCR primers were used for the quantification of eGFP, namely eGFP A and eGFP B (TABLE 1). PCR products for the two eGFP primer pairs were undetectable in the control mice without FUS treatment with the qPCR maximum cycle number set to 40 (TABLE 2). Amplification curves of circulating eGFP mRNA in control and treated mice for the two primer pairs are shown in FIG. 2A. Quantification of the eGFP mRNA in blood collected from U87 mice found the average±standard deviation of $\Delta C_T$ for eGFP A and eGFP B were both 30.7±0.8 for the control group without FUS treatment. For the FUS-treated mice, the average±standard deviation of $\Delta C_T$ for eGFP A and eGFP B were 16.6±5.2 and 19.4±5.4, respectively (TABLE 2).

TABLE 1

Forward and reverse primers used in qPCR for eGFP mRNA and 5.8s rRNA.
Two primers were used for eGFP quantification, called eGFP A and eGFP B. 5.8s rRNA was used as an internal control.

| Primer | Forward | Reverse |
|---|---|---|
| eGFP A | AGAACGGCATCAAGGTGAAC (SEQ ID NO: 1) | TGCTCAGGTAGTGGTTGTCG (SEQ ID NO: 4) |
| eGFP B | TATATCATGGCCGACAAGCA (SEQ ID NO: 2) | ACTGGGTGCTCAGGTAGTGG (SEQ ID NO: 5) |
| 5.8s rRNA | GACTCTTAGCGGTGGATCACT (SEQ ID NO: 3) | CGTTCTTCATCGACGCACGA (SEQ ID NO: 6) |

TABLE 2

Summary of normalized cycle threshold, $\Delta C_T$, for eGFP A and eGFP B in the U87 control mice (C1-C3; n = 3) and treated mice (T1-T6; n = 6).

| Mice Identifier | eGFP A $\Delta C_T$ | eGFP B $\Delta C_T$ |
|---|---|---|
| Control Mice | | |
| C1 | 29.9 | 29.9 |
| C2 | 30.9 | 30.9 |
| C3 | 31.4 | 31.4 |
| Treated Mice | | |
| T1 | 14.8 | 25.9 |
| T2 | 19.6 | 19.3 |
| T3 | 25.1 | 25.1 |
| T4 | 12.8 | 13.6 |
| T5 | 16.4 | 19.1 |
| T6 | 10.8 | 13.3 |

$2^{-\Delta C_T}$ was calculated to compare the relative gene expression levels of the FUS-treated mice and the control mice (see e.g., FIG. 2B and FIG. 2C). For both eGFP primer pairs, circulating mRNA levels of eGFP were significantly higher in the FUS-treated group compared with the untreated control group (eGFP A: p=0.01; eGFP B: p=0.01; one-tailed non-parametric Mann Whitney U Test).

FUS-Enabled Liquid Biopsy in an Orthotopic Murine Xenograft Glioma Model

The second orthotopic glioma model was developed by direct implantation of murine glioma cells (GL261) into the Swiss mice. A magnetic resonance-guided FUS (MRgFUS) system was used for the FUS sonication to achieve accurate tumor targeting (see e.g., FIG. 1C). The MRgFUS system, which was operated at 1.44 MHz, was targeted at the center of the tumor. Three groups of GL261 mice were treated by FUS with acoustic pressures of 1.48 MPa, 2.10 MPa, and 3.34 MPa, respectively. All other parameters were kept the same as those used in the treatment of U87 mice. Contrast-enhanced MR images were acquired before FUS sonication to identify the location of the tumor for FUS targeting and after FUS sonication to verify accurate tumor targeting by the FUS (see e.g., FIG. 1D).

Quantification of the eGFP mRNA in the blood collected from GL261 mice found the average±standard deviation of $\Delta C_T$ for eGFP A and eGFP B were both 23.6±0.2 for the control group. The mean±standard deviation of $\Delta C_T$ for eGFP A was 11.6±0.1 for the 1.48 MPa group, 12.5±0.4 for the 2.01 MPa group, and 12.2±0.1 for the 3.34 MPa group (TABLE 3). The mean±standard deviation of $\Delta C_T$ for eGFP B were 12.2±0.3, 13.7±0.7, and 13.0±0.2 for the three groups, respectively (TABLE 3).

TABLE 3

Summary of normalized cycle threshold, $\Delta C_T$, for eGFP A and eGFP B in the GL261 control mice (C1-C3; n = 3) and treated mice with different acoustic pressures.

| Mice Identifier | eGFP A $\Delta C_T$ | eGFP B $\Delta C_T$ |
|---|---|---|
| Control Mice | | |
| C1 | 23.6 | 23.6 |
| C2 | 23.9 | 23.8 |
| C3 | 23.4 | 23.4 |
| Treated Mice | | |
| 1.48 MPa | 11.6 | 12.4 |
| 1.48 MPa | 11.5 | 11.8 |
| 1.48 MPa | 11.7 | 12.3 |
| 2.10 MPa | 12.5 | 13.9 |
| 2.10 MPa | 12.0 | 12.8 |
| 2.10 MPa | 12.9 | 14.5 |
| 3.34 MPa | 12.3 | 13.2 |
| 3.34 MPa | 12.2 | 13.1 |
| 3.34 MPa | 12.1 | 12.8 |

Figures 3A, 3B:
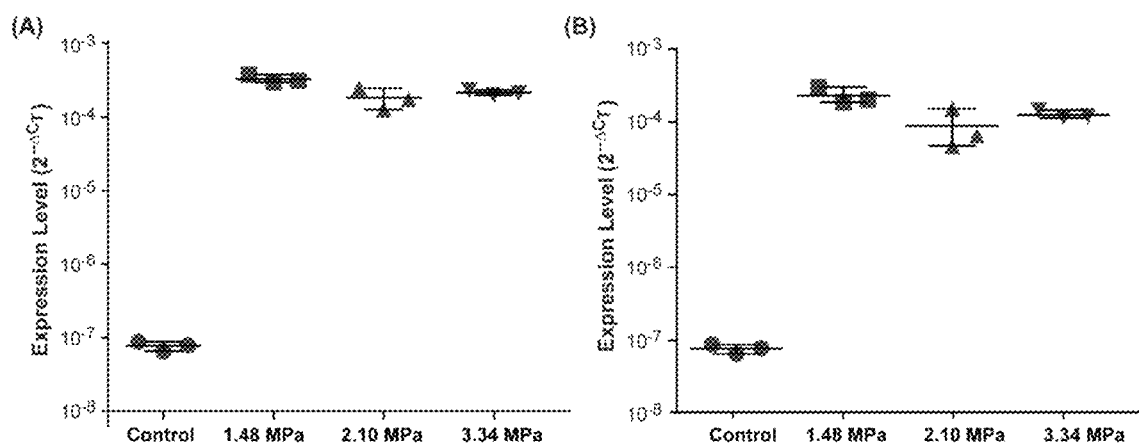
FIG. 3A-FIG. 3B. Comparison of the circulating eGFP mRNA expression in the control and treated GL261 mice. Comparison of the expression levels ($2^{-\Delta C_T}$) of (A) eGFP A and (B) eGFP B in the control group and three treatment groups with different acoustic pressures: 1.48 MPa, 2.10 MPa, and 3.34 MPa. All the measured data points as well as their mean and standard deviation are shown for each group. The circulating mRNA levels of eGFP A and eGFP B were significantly higher in the FUS-treated groups compared with the untreated control group (eGFP A: p=0.0045; eGFP B: p=0.0045). The expression levels of mice in the 1.48 MPa group was significantly higher than those of the other two groups for eGFP A and eGFP B (eGFP A: p=0.012; eGFP B: p=0.012).

Regardless of acoustic pressure, circulating eGFP levels were significantly higher (1,500-4,800 fold higher) in the FUS-treated groups (n=9 in total, eGFP A: p=0.0045; eGFP B: p=0.0045; one-tailed Mann Whitney U Test) relative to the control group (n=3, FIG. 3). The expression levels of mice treated at the lowest pressure (n=3; 1.48 MPa) were significantly higher than those of the other two groups for eGFP A and eGFP B (n=6; eGFP A: 1.7 fold increase in average, p=0.012; eGFP B: 2.2 fold increase in average; p=0.012; one-tailed Mann Whitney U Test). This finding suggests that the relatively lower pressure (1.48 MPa) was more efficient in releasing eGFP mRNA from the tumor than the relatively higher pressures (2.10 MPa and 3.34 MPa). Additionally, these MRI data found that the MR contrast enhancement ratios (calculated by the intensities of the MR images acquired after FUS treatment divided by the intensities of the images obtained before FUS treatment) were not significantly different among the three pressure groups.

Histological Examination

Figures 4A, 4B, 4C, 4D:
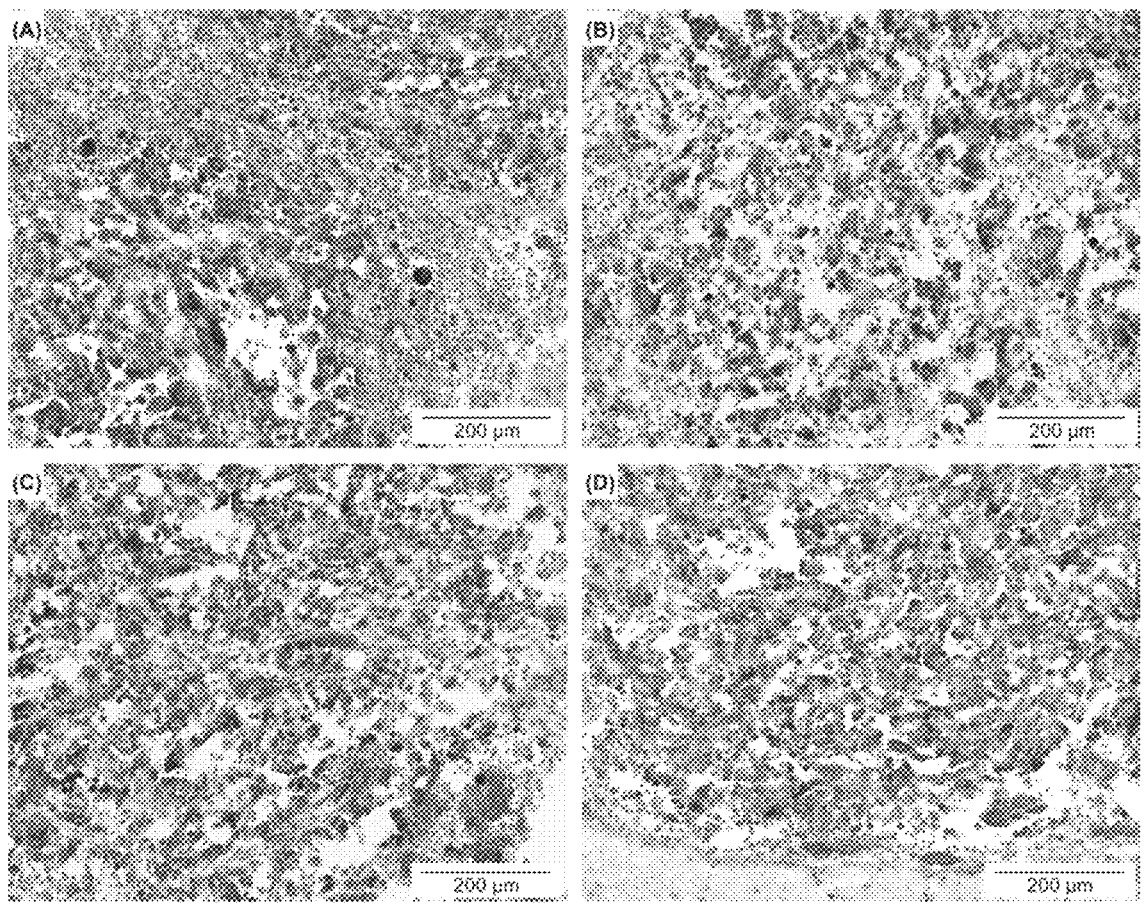
FIG. 4A-FIG. 4D. Histological assessment of brain tissue from the control and treated GL261 mice. H&E staining of the ex vivo tumor slices obtained from the control mice (A) and mice treated with FUS at (B) 1.48 MPa, (C) 2.10 MPa, and (D) 3.34 MPa, respectively. Hemorrhages were observed in all the FUS treated mice.

H&E staining of the GL261 mouse brains found red blood cell extravasation in all mice treated with FUS (see e.g., FIG. 4). More severe hemorrhage was observed in brain slices obtained from mice treated with the relatively higher pressures (2.10 MPa and 3.34 MPa) than mice treated with the relatively lower pressure (1.48 MPa). Vascular damage was expected as the acoustic pressures used in this study were higher than the pressures normally used for the BBB opening without causing vascular damage. Of note, hemorrhage was not observed in the U87 mice treated by FUS at 3.28 MPa. The short interval between FUS sonication and animal scarification in the U87 mice (about 4 minutes vs. 20 minutes in GL261 mice) may have precluded the appearance of red blood cells in the brain slices even in the presence of tissue damage.

Discussion

This study demonstrated the use of FUS-enabled brain liquid biopsy using two glioma mouse models. FUS in combination with microbubbles achieved noninvasive and spatially-localized biomarker release from the brain tumor into the bloodstream. The noninvasive nature of the disclosed FUS technique is especially advantageous over conventional neurosurgical tissue biopsies. Moreover, the technique presents a unique advantage in the assessment of spatially heterogeneous tumors. Tumor heterogeneity, which is a hallmark of glioblastoma[28], poses a significant challenge to cancer biomarker research[29]. FUS can precisely target different locations of the tumor, thereby causing biomarkers to be released in a spatially-localized manner. By targeting multiple tumor regions in a single FUS session, the technique can be used to capture and analyze spatially heterogeneous biomarkers in a single liquid biopsy sample. Another potential functionality would be to perform multiple FUS sessions, each followed by a liquid biopsy, in order to detect specific biomarkers for each spatial location of the tumor to better understand the spatial heterogeneity of the tumor.

Both ultrasound-imaging guided FUS and MRgFUS treatment yielded substantial increase in eGFP RNA levels. However, the standard deviations of the qPCR measurement results for FUS-treated GL261 mice were lower than those of the FUS-treated U87 mice (see e.g., FIG. 2, FIG. 3). This decrease in variations of the experimental results was associated with the use of the MRgFUS system, which improved the tumor targeting accuracy compared with the ultrasound imaging-guided FUS system.

Although damage was observed, the FUS-enabled brain liquid biopsy technique has clear safety benefits compared over craniotomy for surgical biopsy of brain tissue. Moreover, the finding that among the three acoustic pressures the lowest pressure (1.48 MPa) achieved the highest eGFP mRNA expression level is important. It suggests that vascular damage associated with FUS treatment at the relatively higher acoustic pressures (2.10 MPa and 3.34 MPa) may hinder the efficient passage of tumor biomarkers into the peripheral circulation. It also suggests that successful biomarker release may be achievable with acoustic pressures lower than 1.48 MPa, which can improve the safety of the FUS technique. Relatively higher acoustic pressures (1.45-3.34 MPa) were used in the current study than what is commonly used for the BBB disruption (e.g., 0.45 MPa), because in this study it was intended to enhance the interaction between microbubbles and the brain tissues. Optimization of the acoustic parameters (e.g., acoustic pressure, pulse repetition frequency, pulse length, and sonication duration) and microbubble parameters (e.g., size and dose) can be performed to explore the potential to achieve enhanced biomarker release with minimal or no tissue damage.

The disclosed technique can be optimized by assessing the efficiency of biomarker release under different FUS and microbubble parameters (see e.g., Example 2). Specifically, the release of biomarkers using FUS with lower pressures (e.g., 0.45 MPa) that are commonly used for BBB disruption without causing vascular damage can be evaluated. Second, the short-term and long-term safety of the FUS brain liquid biopsy technique can be assessed. Extracranial metastases of glioblastoma are rare[31], and risk for tumor spread after surgical brain biopsies is considered negligible. It is expected that the FUS liquid biopsies will not induce metastatic spread. Nevertheless, studies can be performed to determine the potential of metastasis associated with the FUS treatment. Third, the terminal cardiac puncture was used for blood collection as mice have a small total blood volume (~1.5 mL). Repeated blood sample collection was not feasible using the mouse model, but could be accomplished in humans and larger animals. Larger animal models (e.g., rats, pigs) can be used to collect blood samples at multiple time points after the FUS treatment. These blood samples can be used to assess the temporal dependency of the amount of biomarkers released by the FUS treatment and establish the optimal blood collection time. The larger animal models can be used to evaluate the repeatability of this technique by performing the FUS treatment on the same animal on multiple days. Fourth, the contrast-enhanced MR images acquired before and after the FUS treatment were quantified (see e.g., FIG. 1D). There was no significant difference in the MR contrast enhancement ratios among the three pressure groups (1.48 MPa, 2.10 MPa, and 3.34 MPa). This finding was not consistent with the quantification results of eGFR mRNA expression level shown in FIG. 3, which found the eGFR mRNA expression level in the 1.48 MPa group was significantly higher than that of the other two higher pressure groups. Future studies will determine when lower acoustic pressures are used whether contrast-enhanced MRI is a useful tool in predicting the amount of biomarkers released by FUS. Fifth, the molecular marker (eGFP) was used to demonstrate the feasibility of FUS in noninvasive and spatially-focused liquid biopsy. Studies can use the same methods to assess the other tumor markers (e.g., DNA-based markers). The exact mechanism by which FUS-enabled release of molecular biomarkers is unknown. It is presently believed that the mechanism may be that the FUS-induced BBB disruption opens a "two-way door," allowing "two-way trafficking" between the brain and blood. Future studies will explore the potential mechanisms of FUS-enabled biomarker release.

Conclusions

It was demonstrated that the combination of FUS and microbubbles allows detection of tumor-specific eGFP mRNA in the bloodstream that is otherwise undetectable. The presently disclosed findings established that FUS-mediated BBB disruption could enhance brain-to-blood trafficking. FUS may offer an enabling technique for noninvasive and regionally-specific brain tumor liquid biopsy that can be utilized in personalized brain cancer patient care.

Methods

Orthotopic Mouse Glioblastoma Models

All animal procedures were reviewed and approved by the Institutional Animal Care and Use Committee of Washington University in St. Louis in accordance with the National Institutes of Health Guidelines for animal research.

Two orthotopic mouse glioblastoma models were developed: (i) NCI athymic NCr-nu/nu mice (Strain 553, Charles River Laboratory, Wilmington, Mass., USA) injected with U87 human glioblastoma cells; and (ii) NIH Swiss mice (Strain 550, Charles River Laboratory, Wilmington, Mass., USA) implanted with GL261 murine glioblastoma cells. Mice were anesthetized and fixed into a stereotactic head frame. A paramedian incision was made on the scalp, and a 1-mm burr hole was drilled 2 mm posterior and 1.5 mm lateral to the bregma. eGFP-Luciferase-transduced glioblastoma cells (U87 or GL261) were mixed with Corning™ Matrigel (Catalog 356231, Corning Life Science, New York, USA) and injected through the burr hole using a syringe. The burr hole was sealed with bone wax, and the skin incision was glued together with tissue glue. The growth of the tumor was monitored using IVIS® Spectrum In Vivo Imaging System (Model 124262, PerkinElmer, Ohio, USA) once every week for four weeks. At around fifth week after tumor cell implantation, mice were recruited in the study described below.

Ultrasound Imaging-Guided FUS Treatment of U87 Mice

A total of nine mice with orthotopic U87 glioblastoma tumors were divided into two groups: treatment group (n=6) and control group (n=3). The treatment group was treated with FUS spatially targeted at the tumor site after intravenous injection of microbubbles. The control group received no FUS. For FUS treatment, mice were first anesthetized with 2% isoflurane and placed on a stereotactic frame. A FUS system (VIFU 2000; Alpinion US Inc., Bothell, Wash., USA) sonicated the tumor using the following parameters: frequency=1.5 MHz, peak negative pressure=3.28 MPa, pulse length=10 ms, pulse repetition frequency=1 HZ, duration=30 s at each location, and 4 separate locations were treated for each tumor (see e.g., FIG. 1A and FIG. 1E). The pressure amplitudes and beam dimensions of the FUS transducer were calibrated using a needle hydrophone (Onda, CA, USA) in a degassed water tank before the experiment. The pressures reported here were the peak negative pressures measured in water. The full width at half maximum (FWHM) of the axial beam and lateral beam were 6.04 mm and 0.62 mm, respectively. Before FUS sonication, microbubbles manufactured in house[32] were injected into the mouse tail vein at a concentration of $8 \times 10^8$ microbubbles per mL and a volume of 30 µL per mouse. The in-house manufactured microbubbles comprised of a 90 mol % 1,2-distearoyl-sn-glycero-3-phosphocholine (DSPC) and 10 mol % 1,2-distearoyl-sn-glycero-3-phosphoethanolamine-N-[methoxy(polyethylene gly-col)2000] (DSPE-PEG2000) (Avanti Polar Lipids, Alabaster, Ala., USA) lipid-shell and a perfluorobutane (FluoroMed, Round Rock, Tex., USA) gas-core. These microbubbles had a median diameter of 4-5 mm, which were isolated from a poly-dispersed microbubble distribution using a differential centrifugation method[33].

MRgFUS Treatment of GL261 Mice

A total of 12 mice with implantation of GL261 glioblastoma tumors in the brain were split into four groups: control group (n=3) and three treatment groups (n=3 for each group). The three treatment groups were treated using a clinical MRgFUS system (Sonalleve V2, Profound Medical Inc., Mississauga, Canada) equipped with a dedicated small animal adapter (FUS Instruments Inc., Toronto, Ontario, Canada) (see e.g., FIG. 1C)[34]. The Sonalleve MRgFUS system included a 256-element phased array transducer mounted to a five-axis robot positioner and located inside a modified MRI patient table. The acoustic fields generated by the phased array transducer were calibrated by a fiber optic hydrophone using the previously published method[35]. The FWHM of the axial beam and lateral beam were 12.10 mm and 1.37 mm, respectively. The MRgFUS system was integrated into a clinical MRI scanner (Ingenia 1.5T, Philips, Best, the Netherlands). The small animal adapter included a frame to hold an animal, a water reservoir, and a small animal MRI coil (imaging probe).

For the treatment of GL261 mice, mice were anesthetized with 1-2% isoflurane and placed on the small animal adapter. Optimark (gadoversetamide, a gadolinium-based contrast agent, 0.5 mmol/ml) was injected intravenously into the mice through the tail vein at a dose of 0.1 mmol/kg. Contrast-enhanced 3D, $T_1$-weighted MRI images of the mouse brain were acquired for treatment planning, and the FUS targeted location was selected to be the center of the tumor (see e.g., FIG. 1D). After intravenous injection of the same dose of microbubbles as that was used for U87 mice, the GL261 mice were treated by the MRgFUS system using the following parameters: frequency=1.44 MHz, pulse length=10 ms, pulse repetition frequency=1 Hz, and duration=2 min. The three treatment groups were treated at different peak negative pressures: 1.48 MPa, 2.10 MPa, and 3.34 MPa, respectively. After treatment, contrast-enhanced MRI images were acquired for confirming successful tumor targeting by the FUS (see e.g., FIG. 1D). Blood samples of 500-800 µL were collected from the heart about 20 min after the FUS treatment and prepared for qPCR analysis of eGFP mRNA.

Analysis of eGFP mRNA

Blood samples of 500-800 µL were collected from the heart about 4 min (U87) or 20 min (GL261) after the FUS treatment and prepared for qPCR analysis of eGFP mRNA. All the collected blood was centrifuged at 3,000 rpm for 10 minutes. The supernatant was collected. RNA samples were purified using the miRNeasy serum/plasma kit (Catalog no. 217184, Qiagen, USA). Agencourt RNAClean XP beads (Catalog no. A63987, Beckman Coulter Inc., USA) were used to further purify the RNA. The RNA was then reverse transcribed to cDNA using the Applied Biosystems™ high-capacity cDNA reverse transcription kit (Catalog no. 4368814, Thermo Fisher Scientific, USA). Two eGFP primer pairs (TABLE 1) were designed using OligoPerfect™ Designer (ThermoFisher Scientific, USA). 5.8s rRNA was used as an internal amplification control with its forward and reverse primer sequences also listed in TABLE 1. The quantitative real-time PCR was performed using SYBR™ Green PCR master mix (Applied Biosystems™). All of the PCRs were performed on a 7900HT Fast Real-Time PCR System (Catalog #4329001, Thermo Fisher Scientific, USA) using the following protocol: the reaction mixture was heated at 95° C. for 10 min, followed by 40 cycles of 95° C. for 5 s and 60° C. for 30 s. Amplification and dissociation curves generated by the SDS2.3 (Applied Biosystems) software were used for gene expression analysis.

Duplicate reactions were run for each sample and each primer set. 5.8S rRNA was used as the internal control to normalize the PCR data by calculating cycle threshold change ($\Delta C_T$) by subtracting $C_T$ of the eGFP ($C_{T,eGFP}$) by the $C_T$ of housekeeping gene, 5.8s rRNA ($C_{T,5.8S}$). The gene expression level was determined using the $2^{-\Delta C_T}$ method: $2^{-\Delta C_T} = 2^{-(C_{T,eGFP} - C_{T,5.8s})}$. Maximum cycle number was set to 40. In order to assess the reliability of 5.8S rRNA as the internal control, $2^{-C_T}$ was calculated and compared for the treated and control groups[36]. The $2^{-C_T}$ of the control mice ($1.8 \times 10^{-3} \pm 8.6 \times 10^{-4}$) was not significantly different from the $2^{-C_T}$ of the FUS-treated mice ($1.1 \times 10^{-3} \pm 1.8 \times 10^{-3}$; p=0.38; two-tailed Mann-Whitney U test).

Histological Analysis

After blood collection, all the mice were transcardially perfused with 0.01 M phosphate-buffered saline and then with 4% paraformaldehyde, and their brains were harvested and prepared for paraffin sectioning. The mouse brains were horizontally sectioned to 15 µm slices and used for H&E staining.

Statistical Analysis

GraphPad Prism (v6.04, La Jolla, Calif., USA) and R (v3.4.1, R Core Development Team, 2017) were used to perform statistical analyses. Given the non-normality of $2^{-\Delta CT}$ distribution (Shapiro-Wilk test <0.05), group comparison was made using a non-parametric Mann Whitney U Test. A p-value <0.05 was used to determine statistical significance.

References

1. Warton, K., Mahon, K. L. & Samimi, G. Methylated circulating tumor DNA in blood: Power in cancer prognosis and response. *Endocrine-Related Cancer* 23, R157-R171 (2016).
2. Westphal, M. & Lamszus, K. Circulating biomarkers for gliomas. *Nat. Publ. Gr.* 11, 556-566 (2015).
3. Malone, H. et al. Complications following stereotactic needle biopsy of intracranial tumors. *World Neurosurg.* 84, 1084-1089 (2015).
4. Cohen, J. D. et al. Detection and localization of surgically resectable cancers with a multi-analyte blood test. *Science* 1-9 (2018).
5. Touat, M. et al. Emerging circulating biomarkers in glioblastoma: promises and challenges. *Expert Rev. Mol. Diagn.* 15, 1311-23 (2015).
6. Bettegowda C, et al. Detection of circulating tumor DNA in early- and late-stage human malignancies. *Sci Transl Med* 6, 224ra24 (2014).
7. Boisselier, B. et al. Detection of IDH1 mutation in the plasma of patients with glioma. *Neurology* 79, 1693-1698 (2012).
8. Capper, D. et al. 2-Hydroxyglutarate concentration in serum from patients with gliomas does not correlate with IDH1/2 mutation status or tumor size. *Int. J. Cancer* 131, 766-768 (2012).
9. Martin, E., Jeanmonod, D., Morel, A., Zadicario, E. & Werner, B. High-intensity focused ultrasound for noninvasive functional neurosurgery. *Ann. Neurol.* 66, 858-861 (2009).
10. D'Souza, A. L. et al. A strategy for blood biomarker amplification and localization using ultrasound. *Proc. Natl. Acad. Sci. U.S.A* 106, 17152-17157 (2009).
11. Forbrich, A., Paproski, R., Hitt, M. & Zemp, R. Microbubble-enhanced ultrasound liberation of mRNA biomarkers in vitro. *Ultrasound Med. Biol.* 39, 1087-1093 (2013).
12. Peng, D., Xu, T., Mason, T. J. & Wu, W. A study of ovarian cancer biomarker amplification using ultrasound for early stage detection. *Ultrasonics* 54, 451-454 (2014).
13. Chevillet, J. R. et al. Release of cell-free microRNA tumor biomarkers into the blood circulation with pulsed focused ultrasound: A noninvasive, anatomically localized, molecular liquid biopsy. *Radiology* 283, 258-167 (2016).
14. Paproski, R. J., Jovel, J., Wong, G. K., Lewis, J. D. & Zemp, R. J. Enhanced detection of cancer biomarkers in blood-borne extracellular vesicles using nanodroplets and focused ultrasound. *Cancer Res.* 77, 3-13 (2016).
15. Burgess, A., Shah, K., Hough, O. & Hynynen, K. Focused ultrasound-mediated drug delivery through the blood-brain barrier. *Expert Rev. Neurother.* 15, 477-491 (2015).
16. Aryal, M., Arvanitis, C. D., Alexander, P. M. & McDannold, N. Ultrasound-mediated blood-brain barrier disruption for targeted drug delivery in the central nervous system. *Adv. Drug Deliv. Rev.* 72, 94-109 (2014).
17. Burgess, A. & Hynynen, K. Noninvasive and targeted drug delivery to the brain using focused ultrasound. *ACS Chem. Neurosci.* 8588, 1-7 (2013).
18. Choi, J. J., Selert, K., Vlachos, F., Wong, A. & Konofagou, E. E. Noninvasive and localized neuronal delivery using short ultrasonic pulses and microbubbles. *Proc. Natl. Acad. Sci. U.S.A* 108, 16539-44 (2011).
19. Chen, H. & Konofagou, E. E. The size of blood-brain barrier opening induced by focused ultrasound is dictated by the acoustic pressure. *J. Cereb. Blood Flow Metab.* 34, 1197-204 (2014).
20. O'Reilly, M. A. & Hynynen, K. Feedback-controlled focused ultrasound disruption by using an acoustic emissions-based controller. *Radiology* 263, 96-106 (2012).

21. McDannold, N., Arvanitis, C. D., Vykhodtseva, N. & Livingstone, M. S. Temporary disruption of the blood-brain barrier by use of ultrasound and microbubbles: safety and efficacy evaluation in rhesus macaques. *Cancer Res.* 72, 3652-63 (2012).
22. Baseri, B., Choi, J. J., Tung, Y.-S. & Konofagou, E. E. Multi-modality safety assessment of blood-brain barrier opening using focused ultrasound and definity microbubbles: a short-term study. *Ultrasound Med. Biol.* 36, 1445-59 (2010).
23. Downs, M. E. et al. Long-term safety of repeated blood-brain barrier opening via focused ultrasound with microbubbles in non-human primates performing a cognitive task. *PLoS One* 10, e0125911 (2015).
24. Olumolade, O. O., Wang, S., Samiotaki, G. & Konofagou, E. E. Longitudinal motor and behavioral assessment of blood-brain barrier opening with transcranial focused ultrasound. *Ultrasound Med. Biol.* 42, 1-13 (2016).
25. Radovini, N. N. World first: blood-brain barrier opened non-invasively to deliver chemotherapy—Sunnybrook Hospital. (2015) Available at https://sunnybrook.ca/media/item.asp?i=1351. (Accessed: 4 Mar. 2018)
26. Nadia Norcia Radovin. First Alzheimer's patient treated with focused ultrasound to open the blood-brain barrier. (2017). Available at: https://sunnybrook.ca/media/item.asp?c=1 &i=1562&f=alzheimers-focused-ultrasound-blood-brain-barrier. (Accessed: 4 Mar. 2018)
27. Omuro, A. & DeAngelis, L. Glioblastoma and other malignant gliomas: a clinical review. *Jama* 310, 1842 (2013).
28. Aum, D. J. et al. Molecular and cellular heterogeneity: the hallmark of glioblastoma. *Neurosurg. Focus* 37, E11 (2014).
29. Cyll, K. et al. Tumour heterogeneity poses a significant challenge to cancer biomarker research. 1-9 (2017). doi: 10.1038/bjc.2017.171
30. Jadhav, V., Solaroglu, I., Obenaus, A. & Zhang, J. H. Neuroprotection against Surgically-Induced Brain Injury. *Surg Neurol.* 67, 15-20 (2007).
31. Lun, M., Lok, E., Gautam, S., Wu, E. & Wong, E. T. The natural history of extracranial metastasis from glioblastoma multiforme. *J. Neurooncol.* 105, 261-273 (2011).
32. Chen, H. et al. A new brain drug delivery strategy: focused ultrasound-enhanced intranasal drug delivery. *PLoS One* 9, e108880 (2014).
33. Choi, J. J. et al. Microbubble-size dependence of focused ultrasound-induced blood-brain barrier opening in mice in vivo. *IEEE Trans. Biomed. Eng.* 57, 145-154 (2010).
34. Ellens, N. & Partanen, A. Pre-clinical MRI-guided focused ultrasound: A review of systems and current practices. *IEEE Trans. Ultrason. Ferroelectr. Freq. Control* 64, 1-1 (2016).
35. Kothapalli, S. V. V. N. et al. Acoustic field characterization of a clinical magnetic resonance-guided high-intensity focused ultrasound system inside the magnet bore: *Med. Phys.* 44, 4890-4899 (2017).
36. Schmittgen, T. D. & Livak, K. J. Analyzing real-time PCR data by the comparative CT method. *Nat. Protoc.* 3, 1101-1108 (2008).

Example 2: Optimization of Focused Ultrasound-Enabled Brain Tumor Liquid Biopsy (FUS-Lbx)

The following example describes the optimization of the FUS-LBx technique by investigating the effects of FUS acoustic pressure on the tumor biomarker release level and potentially associated hemorrhage burden.

The development of noninvasive approaches for brain tumor diagnosis and monitoring continues to be a major medical challenge. Although blood-based liquid biopsy has received considerable attention in various cancers, limited progress has been made for brain tumors, at least partly due to the hindrance of tumor biomarker release into the peripheral circulation by the blood-brain barrier. As shown in Example 1, the use of focused ultrasound-enabled brain tumor liquid biopsy (FUS-LBx) was demonstrated. The objective of this example was to optimize the FUS-LBx technique by investigating the effects of FUS acoustic pressure on the tumor biomarker release level and potentially associated hemorrhage burden. Mice with orthotopic implantation of enhanced green fluorescent protein (eGFP)-transfected murine glioma cells were treated using magnetic resonance (MR)-guided FUS system in the presence of systemically-injected microbubbles at three peak negative pressure levels (0.59, 1.29, and 1.58 MPa). Plasma eGFP mRNA levels were quantified with the quantitative polymerase chain reaction (qPCR). Contrast-enhanced MR images were acquired before and after the FUS treatment. FUS at 0.59 MPa resulted in increased plasma eGFP mRNA levels, comparable to those of higher acoustic pressures (1.29 MPa and 1.58 MPa). Hemorrhage associated with FUS at 0.59 MPa was significantly lower than that with higher acoustic pressures and not significantly different from the control group. MRI analysis revealed that post-sonication intratumoral and peritumoral hyperenhancement were associated with the level of FUS-induced biomarker release and the extent of hemorrhage. Taken together, this study suggests that FUS-LBx technique can be optimized to be a safe and effective image-guided biomarker release technique.

Introduction

Central nervous system (CNS) tumors are significant causes of cancer morbidity and mortality, especially in children and young adults where they account for ~20-30% of cancer deaths[1]. Noninvasive neuroimaging modalities (e.g., magnetic resonance imaging (MRI), and computerized tomography (CT)) are used to evaluate tumor lesions, but observed changes, especially after treatment, can be difficult to interpret[2]. Surgical resection or stereotactic biopsy is typically performed for histologic confirmation and increasingly for genetic profiling. However, tissue biopsy requires brain surgery and can be associated with adverse effects such as hemorrhage and infection[3]. Repeated tumor biopsies that may be needed for tracking tumor evolution, treatment response, and tumor recurrence are often not feasible. Furthermore, tissue biopsies may be challenging when tumors are located at difficult locations in the brain or CNS or patients that are too ill to tolerate invasive procedures[4].

Noninvasive blood-based liquid biopsies are a rapidly emerging strategy to provide genetic tumor profiling that can be used for treatment selection, treatment monitoring, residual disease detection, and asymptomatic individual screening[5]. Some success has been achieved in integrating blood-based liquid biopsy into the routine clinical diagnostics[6,7]. However, limited progress has been made for brain tumors. Although several groups have reported biomarker detection in the cerebrospinal fluid (CSF) of patients with brain tumors[8,9], obtaining CSF via lumbar puncture remains an invasive procedure and is often unsafe in these settings. Blood-based liquid biopsies are noninvasive, but there remain multiple hurdles for their application in brain tumors. First, the blood-brain barrier (BBB) restricts the release of large molecules such as DNA and RNA from the tumor to the peripheral circulation[10]. Even though partial BBB disruption is a core feature of glioblastoma (the most common type of high-grade glioma) at the late stage of the tumors, the BBB remains intact in the early stage and the low-grade diffuse gliomas[11]. Second, brain tumors, especially glioblastomas, are heterogeneous with spatially distinct molecular profiling[12]. Localization of tumor areas that harbor specific mutations is not possible using conventional methods of liquid biopsy, as these methods are inherently spatially agnostic. Third, many tumor markers, such as some cell-free RNAs[13] and DNAs[14], have short half-lives in blood. Detection of these biomarkers can be enhanced by stimulating their release from the tumor to the circulation and precisely controlling the blood-collection time to be shorter than their lifetimes in the blood. Therefore, a noninvasive, spatially resolved, and temporally controlled liquid biopsy technique is in great need to improve the clinical care of patients with CNS tumors.

Focused ultrasound-enabled brain tumor liquid biopsy (FUS-LBx) (see e.g., Example 1) offers a technique that can provide noninvasive, spatially resolved, and temporally controlled brain tumor liquid biopsies. FUS has emerged as a technology with the potential to noninvasively exert mechanical and thermal effects on the brain tissue. When coupled with intravenously injected microbubbles, low-intensity pulsed FUS-induced mechanical effects can transiently and non-invasively open the BBB without causing any vascular or tissue damage[16-18]. In Example 1, it was demonstrated that FUS in combination with microbubbles could also be exploited to release biomarkers from brain tumors in murine glioblastoma models[15]. This approach is different from previously reported FUS-facilitated liquid biopsy techniques developed for in vivo biomarker release from cancers outside the brain[19-21]. In one of those reports, pulsed high-intensity focused ultrasound (HIFU) with high acoustic pressures (ultrasound frequency=1.5 MHz, peak compressional focal pressure=90 MPa, and peak rarefactional focal pressure=17 MPa) was used to induce histotripsy (i.e., a technique for mechanical tissue fractionation) in a rat model of prostate cancer, and this enhanced the release of cell-free tumor microRNA into the blood circulation[19]. In another study, a chicken embryo tumor model was used to show the feasibility of amplifying the release of extracellular vesicles using HIFU (ultrasound frequency=1.15 MHz and peak to peak pressure was within the range of 10-30 MPa) in combination with phase-change nanodroplets which changed to microbubbles upon HIFU sonication[20]. In a recent study, two protein biomarkers were found to be significantly increased in the plasma of patients undergoing HIFU thermal ablation (ultrasound frequency=1.1 MHz and power of 100-200 W) of uterine fibroids[21]. All these previous studies used HIFU to induce permanent mechanical or thermal disruption of the tumor to enhance the release of tumor biomarkers. The tissue damaging effect limits the application of these techniques as diagnostic tools in a sensitive organ such as the brain. In contrast, the FUS-LBx technique described here uses low-intensity pulsed FUS, which has the potential advantage of enabling the biomarker release without causing tissue damage. However, in Example 1, the acoustic pressures used were intentionally selected to be relatively high (1.52-3.53 MPa) to increase the chance of success in releasing biomarkers. As expected, hemorrhage was found in the FUS-targeted brain area.

The objective of this example was to investigate the effects of FUS acoustic pressure on the level of tumor biomarker release and the extent of associated hemorrhage in order to optimize the FUS-LBx technique. It was sought to determine the optimal ultrasonic pressure for FUS-LBx that can sufficiently increase plasma levels of the tumor biomarkers while at the same time minimize the risk of hemorrhage in the brain. It was further explored whether post-sonication changes in tumor MR contrast enhancement can predict successful biomarker release for the future development of image-guided FUS-LBx technique.

Results

Effect of the Peak Negative Pressure on FUS-LBx Yield

Figure 5A:
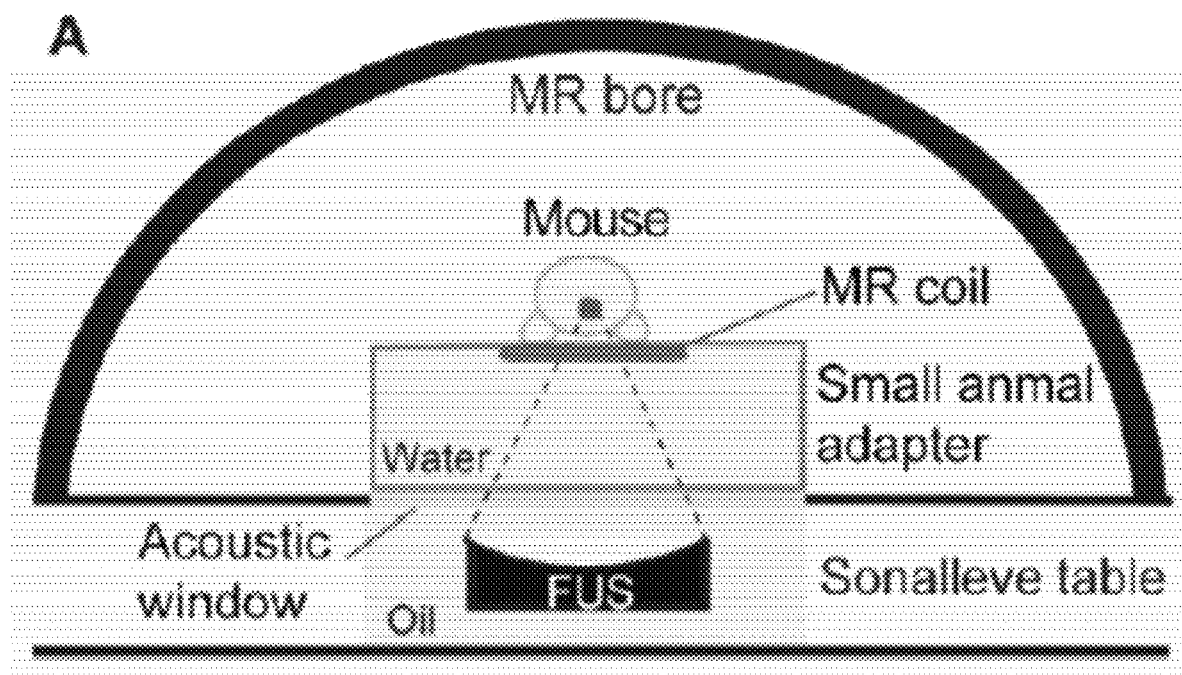
FIG. 5A-FIG. 5C. Experimental setup. (A) Illustration and (B) picture of the MR-guided FUS system used for the FUS-LBx treatment. A clinical MR-guided FUS system that integrated a clinical MRI scanner with a FUS phased array was configured for small animal study by coupling with a small animal adaptor (see Methods for more details). (C) MR image of a fiber-optic hydrophone used for measuring the acoustic pressures. The hydrophone was placed vertically in a water container that was on top of the small animal adapter. The FUS transducer's focus (red dot) was aligned at the tip of the optical fiber for pressure measurements.
Figure 5B:
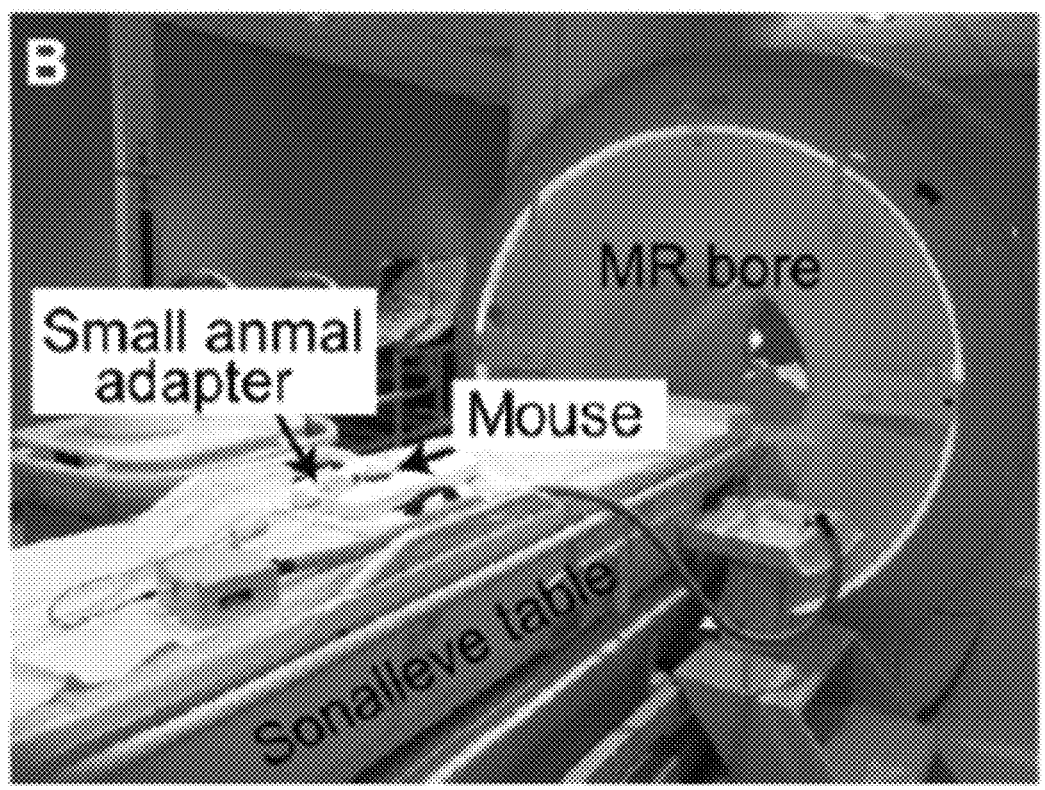
Figure 5C:
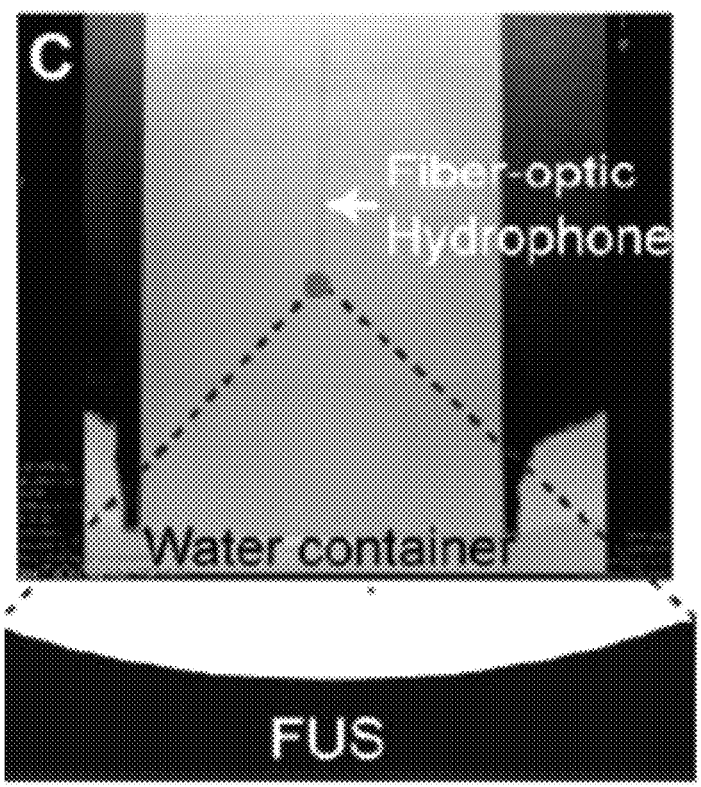

Mice with orthotopic implantation of enhanced green fluorescent protein (eGFP)-transfected murine glioblastoma cells were recruited into this study when the maximum diameter of the tumor reached 2 mm. The mice were treated by an MR-guided FUS system (see e.g., FIG. 5A, FIG. 5B) at three different peak negative acoustic pressure (PNP) levels: (i) 0.59 MPa; (ii) 1.29 MPa; (iii) 1.58 MPa (n=5 in each group). The acoustic pressure output of the FUS transducer was calibrated using a fiber-optic hydrophone following a previously published method (see e.g., FIG. 5C)[22].

Two primer sets were used to improve the robustness of the quantitative polymerase chain reaction (qPCR) results. When compared to the control group (no FUS or microbubble), all three FUS-treated groups demonstrated significant increases in plasma eGFP mRNA levels (all FUS-treated mice vs. control group: one-tailed $p=6.5\times10^{-5}$ for both primer sets: primers A and B; TABLE 4, FIG. 6). When compared with the control group, there were 55-fold (Primer A: one-tailed p=0.004) and 221-fold (Primer B: one-tailed p=0.004) increase in plasma eGFP mRNA levels in mice that received FUS with the lowest PNP (0.59 MPa). Plasma eGFP mRNA levels in mice treated with 1.29 MPa and 1.58 MPa achieved respectively about 2,000-fold and 8,000-fold average enhancement relative to the control group, respectively (TABLE 4). For primer A, plasma eGFP mRNA levels were significantly greater with high acoustic pressures when compared to 0.59 MPa-FUS treated mice (1.29 MPa vs. 0.59 MPa: 35-fold higher, one-tailed p=0.004; 1.58 MPa vs. 0.59 MPa: 151-folder higher, one-tailed p=0.004). These effects were less pronounced when eGFP mRNA levels were measured using primer B (1.29 MPa vs. 0.59 MPa: 5-fold higher, one-tailed p=0.048; 1.58 MPa vs. 0.59 MPa: 22-fold higher, one-tailed p=0.11).

TABLE 4

Group average ± standard deviation of eGFP RNA levels, hemorrhage densities, and tumor MRI enhancement.

| Group | Control | 0.59 MPa | 1.29 MPa | 1.58 MPa |
|---|---|---|---|---|
| eGFP mRNA level (Primer A), $2^{-\Delta CT}$ | $2.2 \times 10^{-8} \pm 3.1 \times 10^{-8}$ | $1.2 \times 10^{-6} \pm 9.1 \times 10^{-7}$ | $4.2 \times 10^{-5} \pm 4.7 \times 10^{-5}$ | $1.8 \times 10^{-4} \pm 9.1 \times 10^{-7}$ |
| eGFP mRNA level (Primer B), $2^{-\Delta CT}$ | $2.2 \times 10^{-8} \pm 1.5 \times 10^{-8}$ | $4.8 \times 10^{-6} \pm 5.5 \times 10^{-6}$ | $2.5 \times 10^{-5} \pm 2.7 \times 10^{-5}$ | $1.0 \times 10^{-4} \pm 1.7 \times 10^{-4}$ |
| Hemorrhage density (%) | 0.12 ± 0.06 | 0.17 ± 0.08 | 0.95 ± 0.6 | 1.7 ± 1.0 |
| Tumor MR enhancement | 12.5 ± 4.1 | 13.7 ± 3.9 | 13.5 ± 3.6 | 13.7 ± 2.2 |

Effect of the Peak Negative Pressure on Brain Hemorrhage

Hematoxylin and eosin (H&E) stained sections of the brain were examined for the presence of microhemorrhages. Representative images of the H&E-stained sections are shown in FIG. 7A-FIG. 7D. After color deconvolution, areas of microhemorrhage were identified using the positive-pixel count algorithm (see e.g., FIG. 7E). Microhemorrhage density was calculated as the proportion of surface area of microhemorrhage to the total surface area of the evaluated brain tissue in a given slice. There was no significant difference in microhemorrhage density between mice treated with 0.59 MPa FUS and the control mice (TABLE 4, FIG. 7F). The microhemorrhage density was significantly higher in 1.29 MPa and 1.58 MPa groups than the 0.59 MPa and control groups. Microhemorrhages seen in the control mice were predominantly scattered in the tumor. In addition to scattered intratumoral microhemorrhage, peritumoral hemorrhage near the interface of the tumor and normal brain parenchyma was seen in 1 out of 5 mice treated with 0.59 MPa FUS as well as in 4 out of 5 mice in the 1.29 MPa and 1.58 MPa FUS-treated groups. Large variations in the hemorrhage density were observed within each group, especially at higher pressures (1.29 MPa and 1.58 MPa).

Predicting FUS-LBx Yield Using MRI

Figures 8A, 8B, 8C, 8D, 8E:
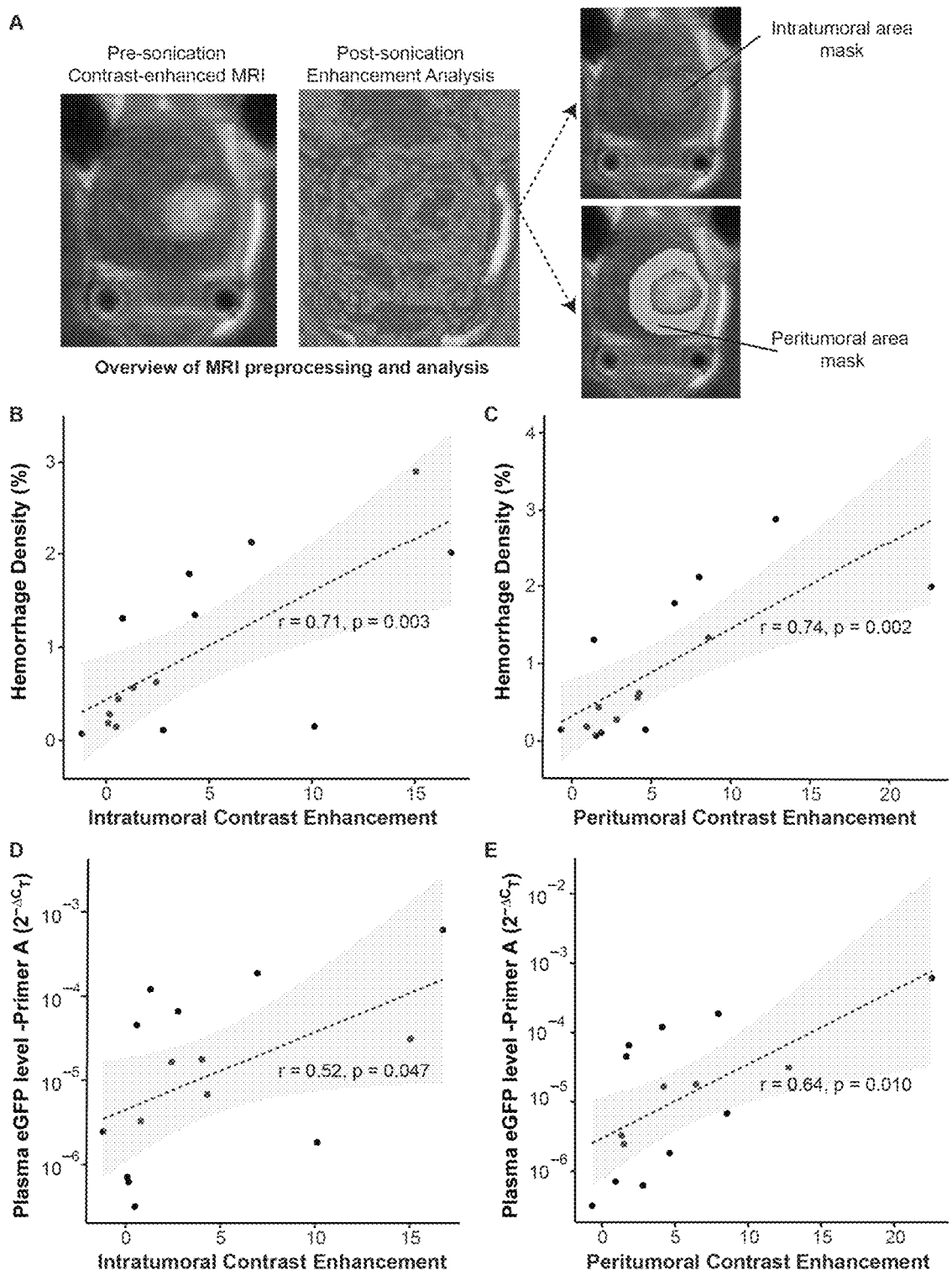
FIG. 8A-FIG. 8E. Relationships between intratumoral and peritumoral MR image contrast enhancements and microhemorrhage density and eGFP mRNA level. (A) Overview of MRI analysis workflow. Tumor MR contrast enhancement was calculated for intratumoral area and peritumoral area (defined as the brain region within 2 mm vicinity of the tumor). (B) Correlation analyses between intratumoral and peritumoral enhancements with microhemorrhage density and plasma eGFP mRNA level in FUS-treated mice (n=15) using primer A.

Increased MRI image intensity on contrast-enhanced MR images was seen both within the tumor and in the peritumoral area of the tumor after sonication (see e.g., FIG. 8A). Because there is a significant difference between intratumoral and peritumoral enhancement before sonication, it was opted to evaluate post-sonication intratumoral and peritumoral enhancement separately. Possible associations between post-sonication enhancements and microhemorrhage density and FUS-LBx yield were interrogated. Greater sonication-induced intratumoral and peritumoral contrast enhancement were associated with higher hemorrhage burden (see e.g., FIG. 8B, FIG. 8C) and greater post-sonication plasma eGFP mRNA levels detected using primer A (see e.g., FIG. 8D, FIG. 8E). The correlation coefficients were lower for the eGFP levels (r=0.52 for intratumoral contrast enhancement and r=0.64 for peritumoral enhancement) than the hemorrhage burden (r=0.71 for intratumoral contrast enhancement and r=0.74 for peritumoral enhancement). Similar associations were seen between intratumoral/peritumoral enhancements and eGFP mRNA levels measured with primer B (r=0.51 for intratumoral contrast enhancement and r=0.56 for peritumoral enhancement). The correlation coefficients for all the above analysis were slightly higher with peritumoral contrast enhancement than intratumoral contrast enhancement.

Discussion

In a murine orthotopic glioblastoma model, it was demonstrated that FUS-LBx technique could be applied with low acoustic pressure without significant sonication-induced hemorrhage. The findings from the prior study[15] (Example 1) were replicated and expanded and used PNPs (0.59-1.58 MPa) that were lower than those in the previous study (1.52-3.53 MPa). Within 0.59-1.58 MPa, higher pressures were associated with a trend of higher biomarker release level but also increased risk of brain hemorrhage.

Figures 6A, 6B:
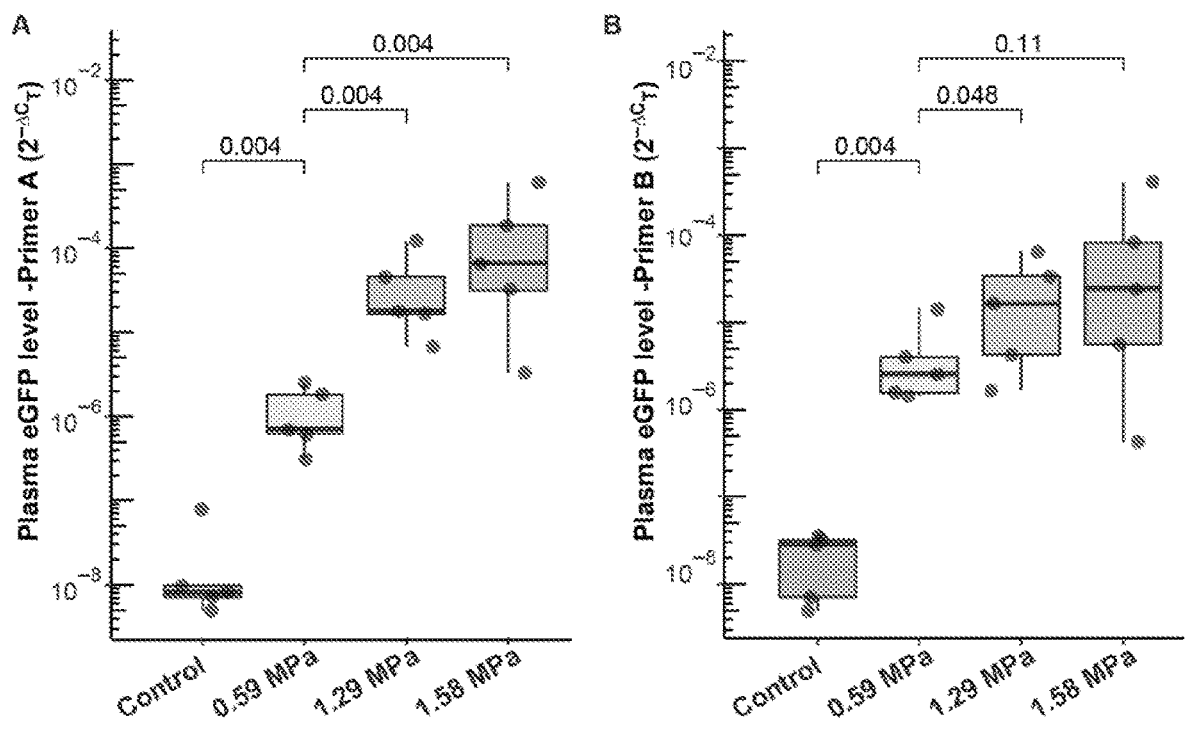
FIG. 6A-FIG. 6B. Effect of peak negative pressure on FUS-LBx yield. Comparison of the circulating eGFP mRNA level in the control mice receiving no treatment and FUS-treated mice at 0.59, 1.29, and 1.58 MPa. eGFP mRNA levels were quantified using quantitative polymerase chain reaction (qPCR) with (A) primer A and (B) primer B.

The results of this study demonstrated that the FUS-induced release of eGFP mRNA from the tumor into the blood circulation is higher when FUS with high PNPs (1.29 and 1.58 MPa) is applied compared with relatively low pressure (0.59 MPa) (see e.g., FIG. 6). The reason for this difference might be that higher PNPs may lead to an increased likelihood of microbubbles undergoing violent inertial cavitation that can, in turn, induce greater disruption of the BBB[23-26]. In this way, there is a higher possibility that a higher amount of eGFP mRNA can be released to the bloodstream. In Example 1, the eGFP mRNA level was found to not be pressure dependent within the range of 1.52-3.53 MPa. Taken together, these findings suggest that as FUS pressure increases the biomarker release level increases and then reaches a plateau. This may be in part due to potential paradoxical effects of increasing PNP on FUS-LBx yield. On the one hand, higher FUS PNP can result in greater BBB disruption, while on the other hand, it can result in vascular damage and decreased tumor perfusion, and hinder tumor biomarker release into peripheral circulation. Moreover, the relative expression levels of eGFP (normalized to 5.8S rRNA) were used in the plasma to index FUS-LBx diagnostic yield. It is possible that at higher PNPs, potentially increased levels of eGFP are offset by possible increases in 5.8S rRNA released from damaged brain tissue.

Figures 7A, 7B, 7C, 7D, 7E, 7F:
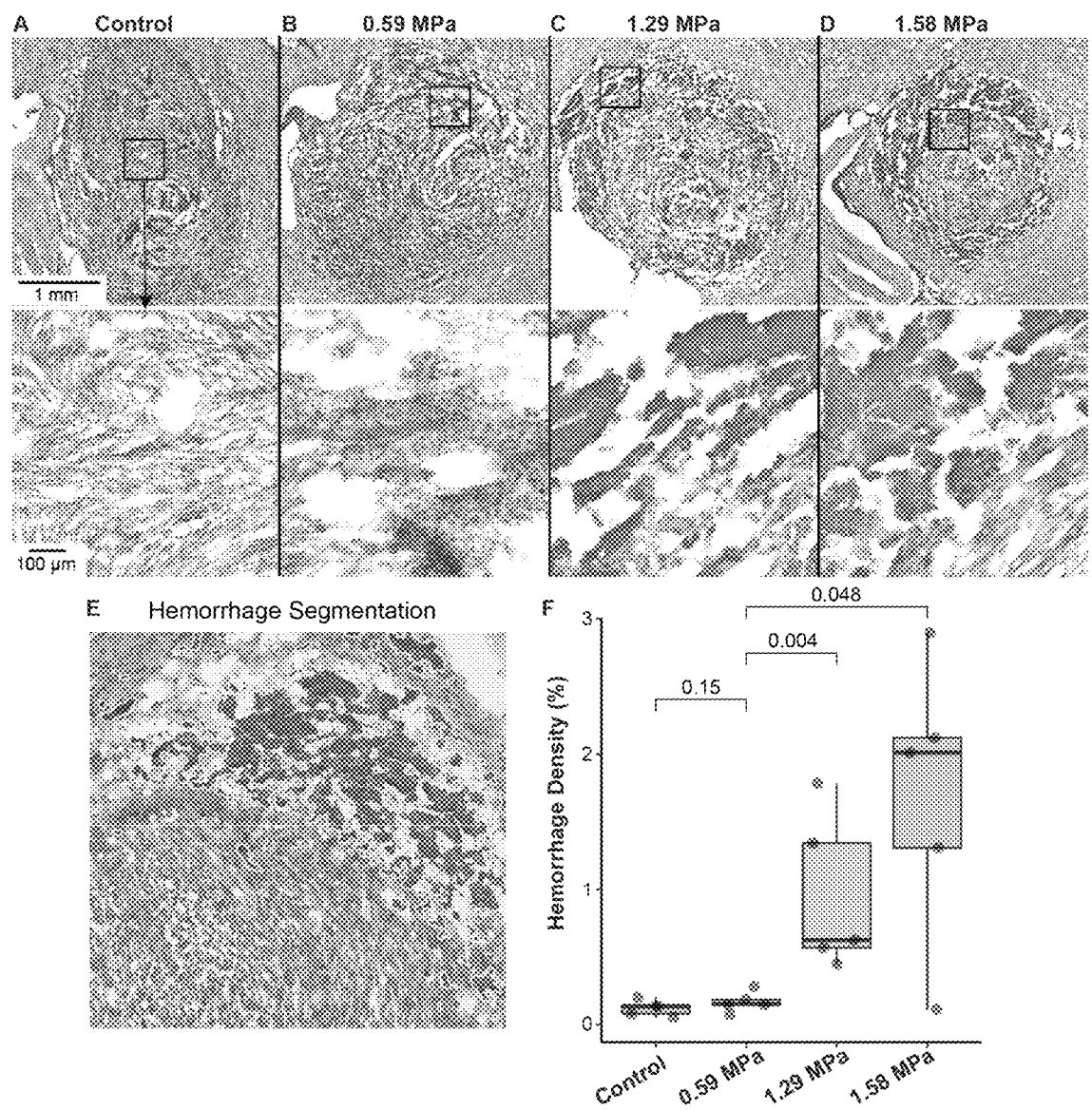
FIG. 7A-FIG. 7F. Effect of peak negative pressure on brain hemorrhage. (A-D) Representative images of H&E-stained sections from mice in the control group, 0.59 MPa, 1.29 MPa, and 1.58 MPa groups, respectively. Boxes in the images on the top indicate the location where the higher magnification images (bottom) were acquired. (E) Illustration of microhemorrhage quantification using the positive pixel detection algorithm (see Methods). Yellow lines highlight the detected microhemorrhage. (C) Microhemorrhage density is significantly higher in mice treated with higher pressures (1.29 MPa and 1.58 MPa) compared to the low pressure (0.59 MPa) and control mice.

For the evaluation of the brain hemorrhage, the results showed a significantly higher microhemorrhage when comparing the 1.29 MPa and 1.58 MPa group with the 0.59 MPa group or the control group (see e.g., FIG. 7). Although there was no statistically significant difference in the extent of microhemorrhage between the control group and the FUS-treated group receiving 0.59 MPa PNP, microhemorrhage beyond the bounds of the tumor was observed along the interface between the tumor and normal brain tissue in one out of five cases. This pattern of hemorrhage was more pronounced with higher FUS PNPs (see e.g., FIG. 7C and FIG. 7D). This pattern of hemorrhage in the tumor periphery may result from the immaturity and instability of peritumoral vasculature rendering them more susceptible to mechanical injury induced by FUS.

Relatively large variations within each group were observed in the analysis of both FUS-LBx yield and FUS-induced hemorrhage. Such variations among repeated FUS treatments have been reported before in FUS-induced BBB disruption experiments. It can be caused by variations in parameters that are hard to control, such as the size distribution of microbubbles that reach the targeted brain location[27], circulating microbubble concentration in blood[28], blood vessel density within the treated region of the tumor[29], and heterogeneous acoustic property of skull[30]. Therefore treatment monitoring techniques, such as passive cavitation imaging[31-33], can be used to detect and characterize potential variations among repeated FUS treatment. Feedback control algorithms can also be implemented based on cavitation monitoring to control the FUS output during the treatment to minimize variations associated with the FUS treatment[34,35].

This study also demonstrated that greater contrast enhancement was associated with both a greater level of eGFP plasma level and a higher hemorrhage density (see e.g., FIG. 8). Post-sonication intratumoral and peritumoral enhancements were both associated with higher released tumor markers in plasma. At the same time, post-sonication enhancement within the tumor and in its periphery were associated with microhemorrhage density. MR imaging markers that can predict safe and successful liquid biopsy are essential for translation of FUS-LBx to the clinic, as they can inform the clinician for sufficiency of FUS application for liquid biopsy or need for a higher magnitude of PNP. Future studies will be performed to explore the potential of MRI in the assessment of FUS-LBx outcome and safety. MRI can be combined with passive cavitation imaging to develop image-guided FUS-LBx which employs real-time passive cavitation imaging for FUS-LBx treatment monitoring and feedback control and utilizes MRI for treatment outcome and safety assessment.

There are limitations to be considered. First, plasma mRNA levels of eGFP were used that were uniquely expressed in the tumor cells to evaluate FUS-mediated liquid biopsy. While this approach is adequate to determine the effectiveness of FUS-LBx, it may not fully recapitulate the clinical settings for liquid biopsy. However, the efficacy of FUS-LBx can be interrogated to discern disease-causing variations of naturally occurring tumor-specific biomarkers[36]. Of note, biomarkers can be evaluated within a short interval from their release to the circulation after FUS application. This permits the detection of short-lived molecules such as mRNAs and some proteins. Second, similar to Example 1, blood was collected using terminal cardiac puncture as mice have a small total blood volume (~1.5 mL). This approach precludes repeated blood sampling to monitor plasma mRNA levels over time following sonication or to determine the effects of serial FUS-mediated BBB opening on plasma tumor biomarkers. Therefore, in order to determine the temporal pattern of released tumor biomarkers and feasibility of serial liquid biopsy, FUS-LBx needs to be evaluated in larger animal models such as rats, pigs, and non-human primates. Third, a few inconsistencies were observed in plasma eGFP mRNA findings with different primer sets. Although eGFP mRNA measured with both primer sets was overall highly correlated (r=0.93, root mean square difference=1.85 cycle threshold), the difference between plasma eGFP mRNA levels of mice treated 0.59 MPa and higher PNPs were less prominent with primer set B. More robust and reproducible measurements of RNA levels with droplet digital PCR[37] could mitigate these issues and enable reliable detection of small differences in FUS-LBx.

Conclusions

This study showed that an acoustic pressure as low as 0.59 MPa was sufficient for FUS-LBx. Although higher peak negative acoustic pressures tended to be associated with a better yield of liquid biopsy, it was also associated with a higher burden of microhemorrhage. MRI can be used in not only guiding the FUS targeting of a specific brain region but also providing predictions of the biomarker release level and potential hemorrhage extent. Future studies are warranted to develop MRI-guided FUS-LBx to improve its safety and efficacy.

Methods

FUS-LBx Treatment Procedure

All animal studies were reviewed and approved by the Institutional Animal Care and Use Committee of Washington University in St. Louis in accordance with the National Institutes of Health Guidelines for animal research.

Mice (Strain 550, 6-8 weeks, n=20, Charles River Laboratory, Wilmington, Mass., USA) were implanted with GL261 murine glioblastoma cells on day 0 using an established protocol[15]. The growth of the tumor was monitored using a clinical MRI scanner (Ingenia 1.5T, Philips Healthcare, Best, the Netherlands) coupled with a small animal coil (FUS Instruments Inc., Toronto, Ontario, Canada) as shown in FIG. 5 twice per week. Once the maximum diameter of the tumor reached 2 mm as measured based on the contrast-enhanced MRI, the mice were randomly assigned into four groups: control group that received no treatment (n=5) and three groups that received FUS treatment with three different PNP: 0.59 MPa (n=5), 1.29 MPa (n=5), and 1.58 MPa (n=5). All other parameters were the same across the treatment groups: 1.44 MHz, sonication duration: 240 s; treatment target: 1 (at the center of the tumor); pulse repetition frequency: 1 Hz; duty cycle: 1%; pulse length: 10 ms. All FUS sonications were performed on post-implantation days 15 or 16.

The details of the sonication procedure and the dose and concentration of the microbubbles have been described previously[15]. Briefly, the mice were treated by FUS using a clinical MR-guided FUS system (Sonalleve V2, Profound Medical Inc., Mississauga, Canada) that integrated a clinical MRI scanner (Ingenia 1.5T, Philips Healthcare, Best, the Netherlands) with a 256-element phased array FUS transducer. The system was configured for small animal study by coupling with a small animal adaptor (FUS Instruments Inc., Toronto, Ontario, Canada) placed above the acoustic window of the FUS transducer (see e.g., FIG. 5A and FIG. 5B). The adaptor consisted of a small animal coil, a standoff, and a mouse bed. The software of the MR-guided FUS system was modified to achieve tumor targeting under the guidance of MR images of mouse brains acquired using the small animal coil. It was also modified to perform pulsed FUS sonication at low-pressure levels used in this study by only using 128 elements. The acoustic fields generated by the phased array transducer was calibrated by a fiber optic hydrophone using previously published methods (see e.g., FIG. 5C)[22,38]. The full width at half maximum of the axial beam and lateral beam was 12.10 mm and 1.37 mm, respectively.

Contrast-enhanced T1-weighted turbo spin-echo MR images (TR, 500 ms; TE, 13 ms; acquisition matrix, 96×96; resolution, 0.2 mm×0.2 mm×0.5 mm) were acquired before and after the FUS treatment to quantify changes in intratumoral and peritumoral enhancement.

Plasma eGFP mRNA Level Quantification

Blood samples of 500-800 μL were collected from the heart about 20 min after FUS sonication and prepared for qPCR analysis of eGFP mRNA. The methods of qPCR analysis of eGFP mRNA have been described in Example 1. Briefly, RNA was extracted from the plasma samples using miRNeasy serum/plasma kit (Catalog no. 217184, Qiagen, USA) followed by Agencourt RNAClean XP beads (Catalog no. A63987, Beckman Coulter Inc., USA). Extracted RNA was then converted to cDNA using the Applied Biosystems high-capacity cDNA reverse transcription kit (Catalog no. 4368814, Termo Fisher Scientifc, USA). Two primer sets were used to quantify eGFP levels. 5.8S rRNA was used as the internal control to normalize the PCR data by calculating cycle threshold change ($\Delta C_T$) by subtracting $C_T$ of the eGFP ($C_{T,eGFP}$) by the $C_T$ of the housekeeping gene, 5.8s rRNA ($C_{T,5.8S}$). The relative gene expression level was determined using the $2^{-\Delta CT}$ method: $2^{-\Delta C_T} = 2^{-(C_{T,eGFP} - C_{T,5.8s})}$.

MRI Image Analysis

MR image processing and analysis were performed using tools available in FSL v5.0.10[36]. First, tumor regions were segmented semi-automatically on the pre-sonication contrast-enhanced T1-weighted images using ITK-SNAP v3.6.0[35]. Second, on each pre-sonication contrast-enhanced T1-weighted MRI image of the brain tumor, a spherical control mask with 1 mm radius was drawn in the normal appearing brain and its mean and standard deviation were calculated. Third, all contrast-enhanced T1-weighted images (both pre-sonication and post-sonication images) were intensity normalized by subtracting the mean and then dividing by the standard deviation of the signal intensity within the control mask. Fourth, the peritumoral area was defined as the brain regions within 2 mm vicinity of the tumor. A preliminary mask was created using the distancemap command in FSL. This mask was then edited manually to exclude voxels outside the brain parenchyma. Finally, to quantify post-sonication changes in MRI contrast enhancement, the difference between normalized post-sonication and pre-sonication T1-weighted images was calculated within the intratumoral and peritumoral area masks.

Histologic Analysis

After blood collection, all mice were transcardially perfused with 0.01 M phosphate-buffered saline (PBS) followed by 4% paraformaldehyde. Brains were harvested and prepared for paraffin sectioning. The mouse brains were horizontally sectioned to 15 μm slices and used for H&E staining. Whole slide images of H&E tissue sections were digitally acquired using Nanozoomer 2.0-HT slide scanner (Hamamatsu Photonics, Hamamatsu City, Japan). For each mouse, the H&E stained slice with the largest tumor surface area and least artifact was selected for quantitative analysis. QuPath v0.1.3[39] was used to detect areas of microhemorrhage. After color deconvolution (hematoxylin vs. eosin), areas of microhemorrhage was detected using the positive-pixel count algorithm. Microhemorrhage density was calculated as the percentage of microhemorrhage surface area over the entire evaluated surface area (%).

Statistical Analysis

All statistical analyses were performed using R statistical software v3.5.0 (https://www.R-project.org/)[40] and graphically displayed using ggplot2 package v2.2.1[41]. For group comparisons, the non-parametric Mann-Whitney U test was used. Associations between two continuous variables were assessed using Pearson correlation analysis. eGFP plasma levels were log transformed for correlation analysis. Statistical significance was set at $p<0.05$.

References

1. Fisher, J. L., Schwartzbaum, J. A., Wrensch, M. & Wiemels, J. L. Epidemiology of brain tumors. Neurol. Neurol Clin 25, 867-890 (2007).
2. Omuro, A. M. P., Leite, C. C., Mokhtari, K. & Delattre, J.-Y. Pitfalls in the diagnosis of brain tumours. 5, 937-948 (2006).
3. Malone, H. et al. Complications following stereotactic needle biopsy of intracranial tumors. World Neurosurg. 84, 1084-1089 (2015).
4. Ragel, B. T. et al. The role of biopsy in the management of patients with presumed diffuse low grade glioma: A systematic review and evidence-based clinical practice guideline. J. Neurooncol. 125, 481-501 (2015).
5. Merker, J. D. et al. Circulating tumor DNA analysis in patients with cancer: American society of clinical oncology and college of American pathologists joint review. Arch. Pathol. Lab. Med. 142, 1242-1253 (2018).
6. Cohen, J. D. et al. Detection and localization of surgically resectable cancers with a multi-analyte blood test. Science. 359, 926-930 (2018).
7. Bardelli, A. & Pantel, K. Liquid biopsies, what we do not know (yet). Cancer Cell 31, 172-179 (2017).
8. Miller, A. M. et al. Tracking tumour evolution in glioma through liquid biopsies of cerebrospinal fluid. Nature 565, 654-658 (2019).
9. Figueroa, J. M. et al. Detection of wild-Type EGFR amplification and EGFRvIII mutation in CSF-derived extracellular vesicles of glioblastoma patients. Neuro. Oncol. 19, 1494-1502 (2017).
10. Bettegowda C, Sausen M, Leary R J, Kinde I, Wang Y, Agrawal N, Bartlett B R, Wang H, Luber B, Alani R M, Antonarakis E S, Azad N S, Bardelli A, Brem H, Cameron J L, Lee C C, Fecher L A, Gallia G L, Gibbs P, Le D, Giuntoli R L, Goggins M, Hogarty M D, Holdhoff M, Hon, D. L. J. Detection of circulating tumor DNA in early- and late-stage human malignancies. Sci Transl Med 6, 224ra24 (2014).
11. Van Tellingen, O. et al. Overcoming the blood-brain tumor barrier for effective glioblastoma treatment. Drug Resist. Updat. 19, 1-12 (2015).
12. Aum, D. J. et al. Molecular and cellular heterogeneity: the hallmark of glioblastoma. Neurosurg. Focus 37, E11 (2014).
13. Vogel, C. & Marcotte, E. M. Insights into the regulation of protein abundance from proteomic and transcriptomic analyses. Nat. Rev. Genet. 13, 227-232 (2012).
14. Yong, E. Cancer biomarkers: Written in blood. Nature 511, 524-526 (2014).
15. Zhu, L. et al. Focused ultrasound-enabled brain tumor liquid biopsy. Sci. Rep. 8, 6553 (2018).
16. Kinoshita, M., McDannold, N., Jolesz, F. A. & Hynynen, K. Noninvasive localized delivery of Herceptin to the mouse brain by MRI-guided focused ultrasound-induced blood-brain barrier disruption. Proc Natl Acad Sci 103, (2006).
17. Choi, J. J., Selert, K., Vlachos, F., Wong, A. & Konofagou, E. E. Noninvasive and localized neuronal delivery using short ultrasonic pulses and microbubbles. Proc. Natl. Acad. Sci. U.S.A 108, 16539-44 (2011).
18. Chen, H. & Konofagou, E. E. The size of blood-brain barrier opening induced by focused ultrasound is dictated by the acoustic pressure. J. Cereb. Blood Flow Metab. 34, 1197-204 (2014).
19. Chevillet, J. R. et al. Release of cell-free microRNA tumor biomarkers into the blood circulation with pulsed focused ultrasound: A noninvasive, anatomically localized, molecular liquid biopsy. Radiology 283, 258-167 (2016).
20. Paproski, R. J., Jovel, J., Wong, G. K., Lewis, J. D. & Zemp, R. J. Enhanced detection of cancer biomarkers in blood-borne extracellular vesicles using nanodroplets and focused ultrasound. Cancer Res. 77, 3-13 (2016).
21. Souza, A. L. D. et al. Tumor characterization by ultrasound-release of multiple protein and microRNA biomarkers, preclinical and clinical evidence. PLoS One 13, e0194268 (2018).
22. Kothapalli, S. V. V. N. et al. Acoustic field characterization of a clinical magnetic resonance-guided high-intensity focused ultrasound system inside the magnet bore: Med. Phys. 44, 4890-4899 (2017).
23. El Kaffas, A. & Czarnota, G. J. Biomechanical effects of microbubbles: from radiosensitization to cell death. Future Oncol. 11, 1093-108 (2015).
24. Mornstein, V. Cavitation-induced risks associated with contrast agents used in ultrasonography. European Journal of Ultrasound 5, 101-111 (1997).
25. Stride, E. Physical principles of microbubbles for ultrasound imaging and therapy. Cerebrovasc. Dis. 27, 1-13 (2009).
26. Wood, A. K. W. & Sehgal, C. M. A Review of low-intensity ultrasound for cancer therapy. Ultrasound Med. Biol. 41, 905-928 (2015).
27. Choi, J. J. et al. Microbubble-size dependence of focused ultrasound-induced blood-brain barrier opening in mice in vivo. IEEE Trans. Biomed. Eng. 57, 145-154 (2010).
28. Morel, D. R. et al. Human pharmacokinetics and safety evaluation of SonoVue™, a new contrast agent for ultrasound imaging. Invest. Radiol. 35, 80 (2000).
29. Wu, S.-Y. et al. Characterizing focused-ultrasound mediated drug delivery to the heterogeneous primate brain in vivo with acoustic monitoring. Sci. Rep. 6, 37094 (2016).
30. Aldiabat, H., O'Brien, P. D., Liu, D. & Ebbini, E. S. Wideband transskull refocusing of ultrasound beams using dual-mode ultrasound arrays: Ex vivo results. J. Acoust. Soc. Am. 143, 1731 (2018).

31. Jones, R. M. et al. Three-dimensional transcranial microbubble imaging for guiding volumetric ultrasound-mediated blood-brain barrier opening. *Theranostics* 8, 2909 (2018).
32. Wu, S.-Y. et al. Efficient blood-brain barrier opening in primates with neuronavigation-guided ultrasound and real-time acoustic mapping. *Sci. Rep.* 8, 7978 (2018).
33. Arvanitis, C. D., Crake, C., McDannold, N. & Clement, G. T. Passive acoustic mapping with the angular spectrum method. *IEEE Trans. Med. Imaging* 36, 983-993 (2016).
34. Sun, T. et al. Closed-loop control of targeted ultrasound drug delivery across the blood-brain/tumor barriers in a rat glioma model. *Proc. Natl. Acad. Sci.* 114, E10281-E10290 (2017).
35. O'Reilly, M. A. & Hynynen, K. Feedback-controlled focused ultrasound disruption by using an acoustic emissions-based controller. *Radiology* 263, 96-106 (2012).
36. Zachariah, M. A., Oliveira-Costa, J. P., Carter, B. S., Stott, S. L. & Nahed, B. V. Blood-based biomarkers for the diagnosis and monitoring of gliomas. *Neuro. Oncol.* 20, 1155-1161 (2018).
37. Taylor, S. C., Laperriere, G. & Germain, H. Droplet Digital PCR versus qPCR for gene expression analysis with low abundant targets: from variable nonsense to publication quality data. *Sci. Rep.* 7, 2409 (2017).
38. Kothapalli, S. V. V. N. et al. A convenient, reliable, and fast acoustic pressure field measurement method for magnetic resonance-guided high-intensity focused ultrasound systems with phased array transducers. *J. Ther. Ultrasound* 6, 5 (2018).
39. Bankhead, P. et al. QuPath: Open source software for digital pathology image analysis. *Sci. Rep.* 7, (2017).
40. R Core Team. R: A language and environment for statistical computing. (2018).
41. Wickham, H. ggplot2: *Elegant Graphics for Data Analysis*. (Springer-Verlag New York, 2016).

Example 3: Noninvasive and Localized Blood-Brain Barrier Opening and Detection of Brain-Specific Biomarkers This example shows the pressure field measurements of the designed transducer and the evaluation of its performance and the detection of brain-specific biomarkers.

Blood-brain barrier (BBB) opening with focused ultrasound and microbubbles (MB) have been demonstrated to be a noninvasive, targeted, safe, and effective technique mostly in anesthetized animal models. However, the requirement of anesthesia can limit the future clinical application of this noninvasive technology for the treatment of brain diseases as patient real-time feedback is critical to ensure the safety of the treatment. So far, only one study demonstrated the feasibility of BBB opening using FUS in awake non-human primates after training the non-human primates to cooperate during the treatment. No study has evaluated the feasibility of FUS-induced BBB opening in the most commonly used animal model—mice, because of the technical challenges associated with designing a device for FUS sonication in awake mice.

The blood-brain barrier (BBB) blocks large molecules (>400 Da) from entering the central nervous system (CNS). Focused Ultrasound (FUS) combined with microbubble is the only available technique to non-invasively, locally, and transiently open the BBB. Previous preclinical research using small animal models has demonstrated this technique as a promising way to treat various brain disorders. This technique has also been tested on non-human primates with success. Clinical Studies with FUS are actively investigated for treatment of brain tumor and Alzheimer's disease. Besides its clinical translation potential, this technique has a broad application in preclinical research. It can be used to delivery various agents to the brain, such as chemo drugs, proteins, peptides, nanoparticles, gene vectors, and stem cells. However, currently there is a lack of devices that are affordable, high throughput, and dedicated for small animal research. Here is disclosed a new FUS-induced BBB opening device that meets these needs. The transducer was made using an inexpensive flat ultrasound transducer coupled to a 3D printed acoustic lens. The cost of the transducer was about $80, while the FUS transducer commonly used in preclinical research can cost over $2,000. Multiple transducers can be used simultaneously to achieve high throughput treatment of multiple mice at the same time.

A wearable helmet was designed for non-invasive, targeted FUS sonication of the mouse brain while the animals were awake. The helmet had a modular design featuring easy removal and installing of the unit for targeting different brain regions. The performance of the helmet in inducing BBB opening at the caudate putamen was assessed in four awake mice and four anesthetized mice in the presence of intravenously injected microbubbles. Evan's blue was co-injected with the microbubbles for the evaluation of the BBB permeability using fluorescence imaging of ex vivo brain slices.

The whole helmet with ultrasound transducer and wirings weighed 6.6 g. The constraint design of the helmet minimized the effect of mouse movement on targeting. The helmet achieved localized BBB opening at the targeted brain location. The fluorescence intensity of the Evan's blue in the brains of awake mice was higher than that in anesthetized mice, suggesting that FUS-induced BBB opening was affected by anesthesia.

The helmet design of the FUS device provides an innovative tool to study FUS-induced BBB opening in awake mice.

Figure 9:
FIG. 9 is a photo of the transducer.
Figure 10:
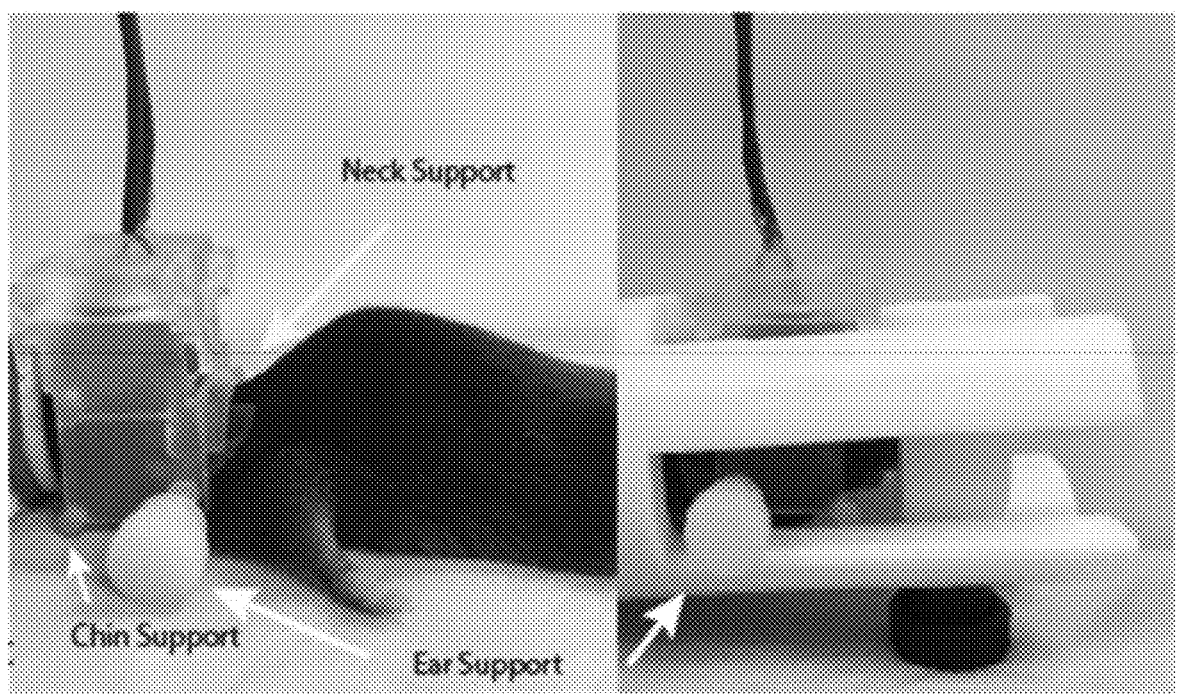
FIG. 10 is a photo of a mouse treated using the device.
Figure 11:
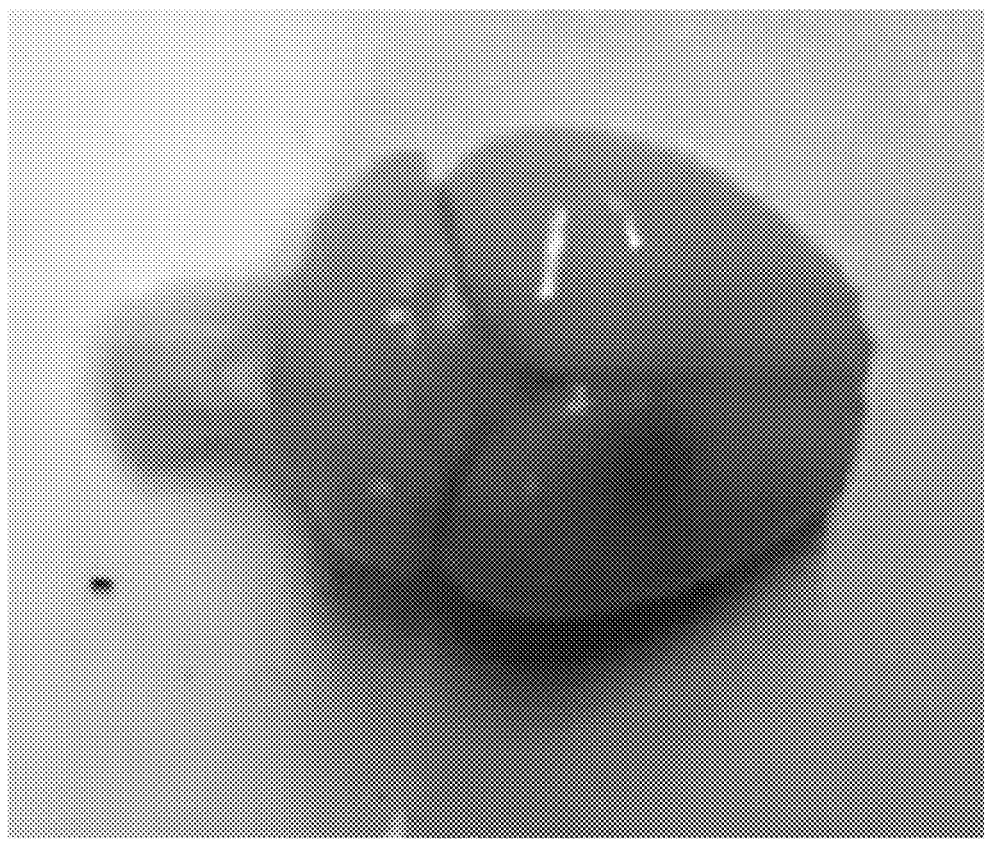
FIG. 11 is a photo showing the successful drug delivery to the mouse brain, indicated by the leakage of the blue color.
Figure 12:
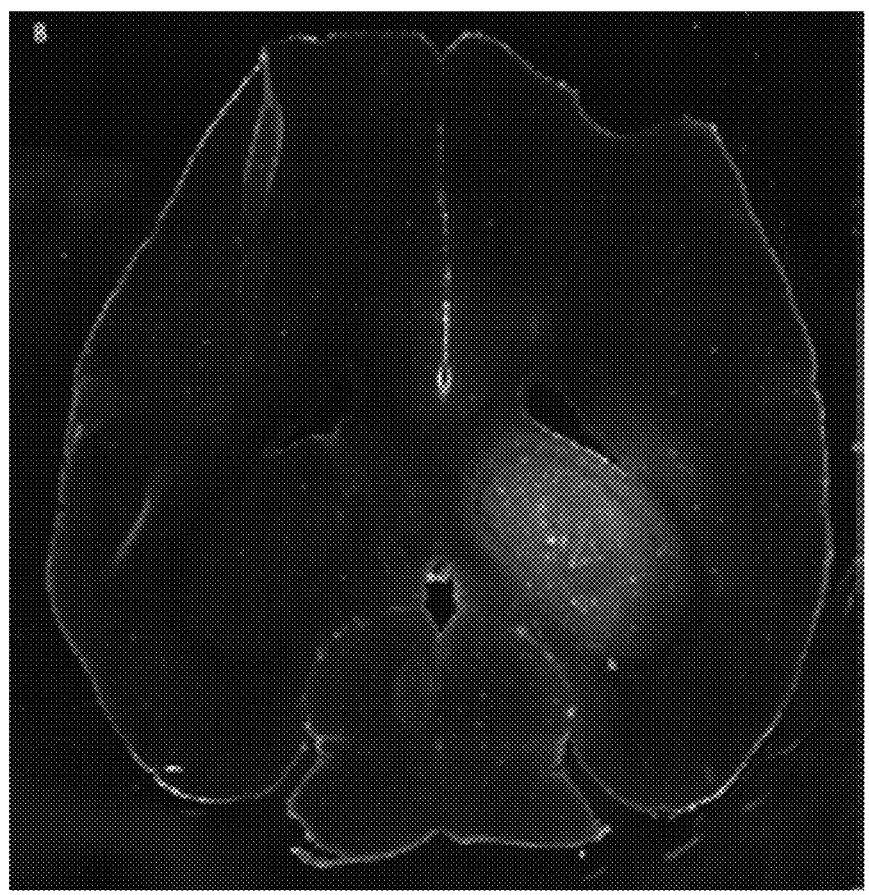
FIG. 12 is an image of spatially precise drug delivery to the hippocampus, indicated by the enhanced fluorescence observed on the right side of the of the mouse hippocampus.

FIG. 9 is a photo of the transducer. FIG. 10 is a photo of a mouse treated using the device. FIG. 11 is a photo showing the successful drug delivery to the mouse brain, indicated by the leakage of the blue color. FIG. 12 is an image of spatially precise drug delivery to the hippocampus, indicated by the enhanced fluorescence observed on the right side of the of the mouse hippocampus.

Figure 13A:
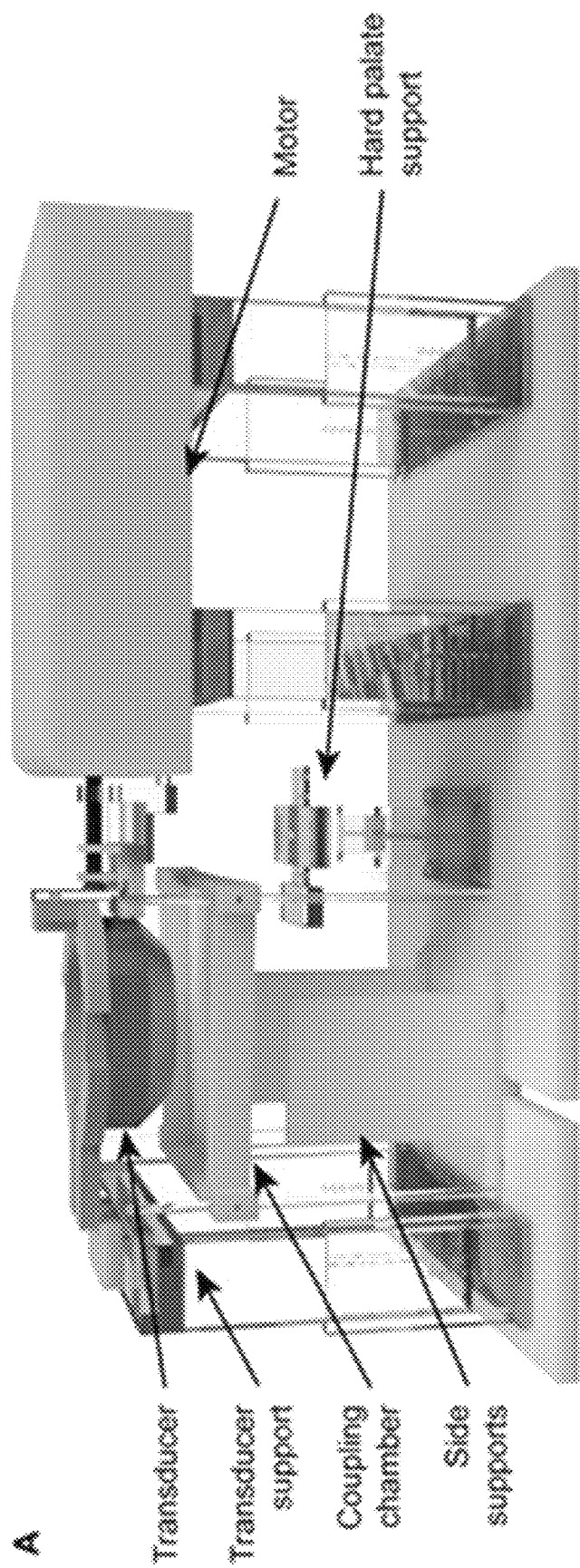
FIG. 13 is a series of images of an MRgFUS system design for a pig.
Figure 13B:
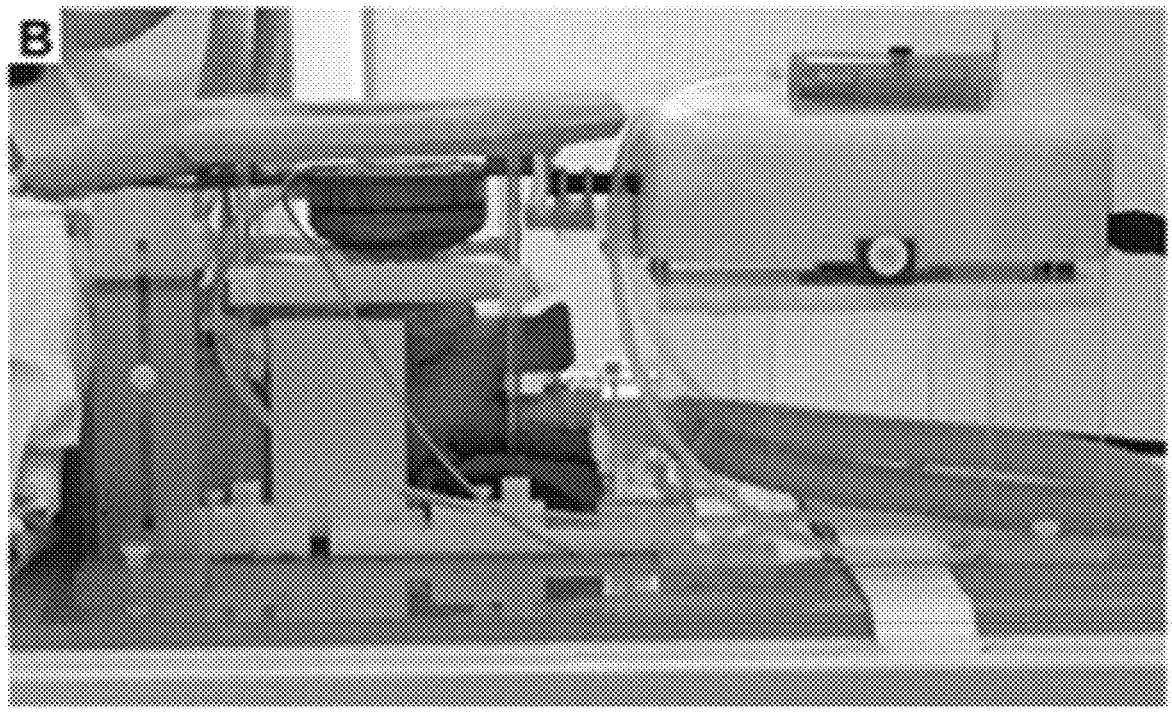
Figure 13C:
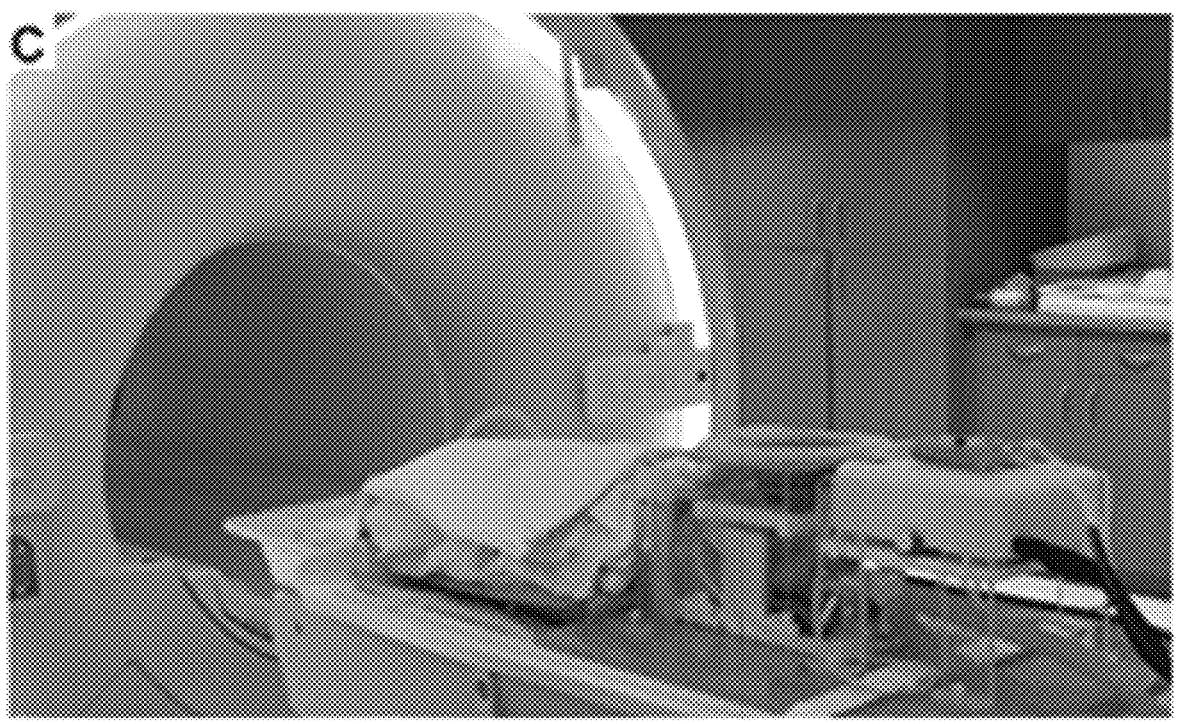

An MRgFUS system was also designed for a pig (see e.g., FIG. 13). This design can be easily configured for clinical use by humans. The MRgFUS system is designed to integrate into the bore of an MRI scanner (see e.g., FIG. 13C).

Figure 14:
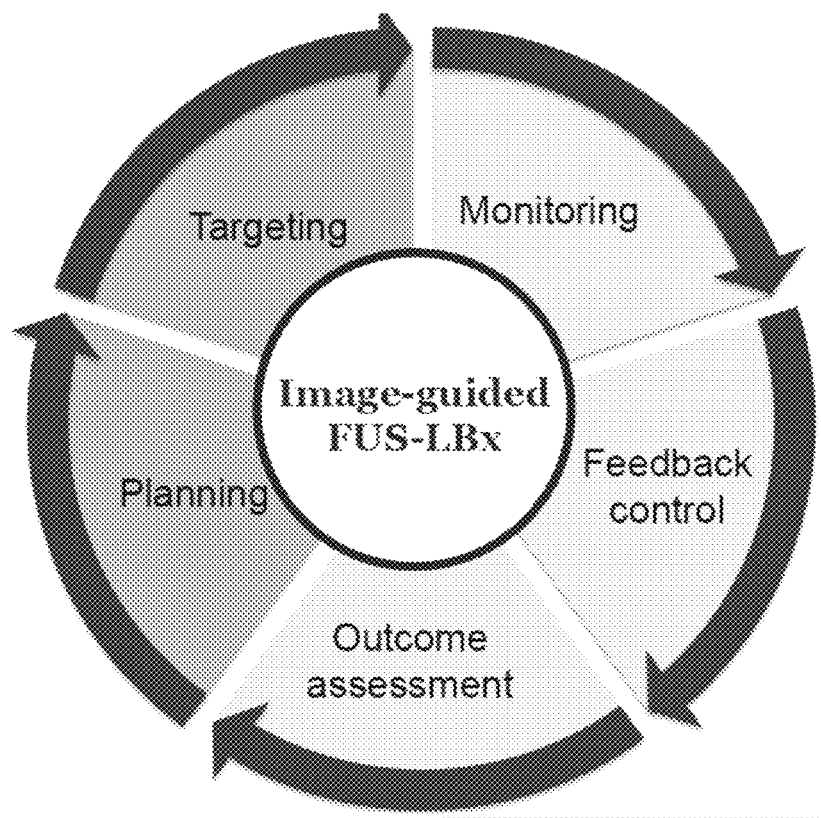
FIG. 14. Planning and targeting of image-guided focused ultrasound liquid biopsy (FUS-LBx).
Figure 14:
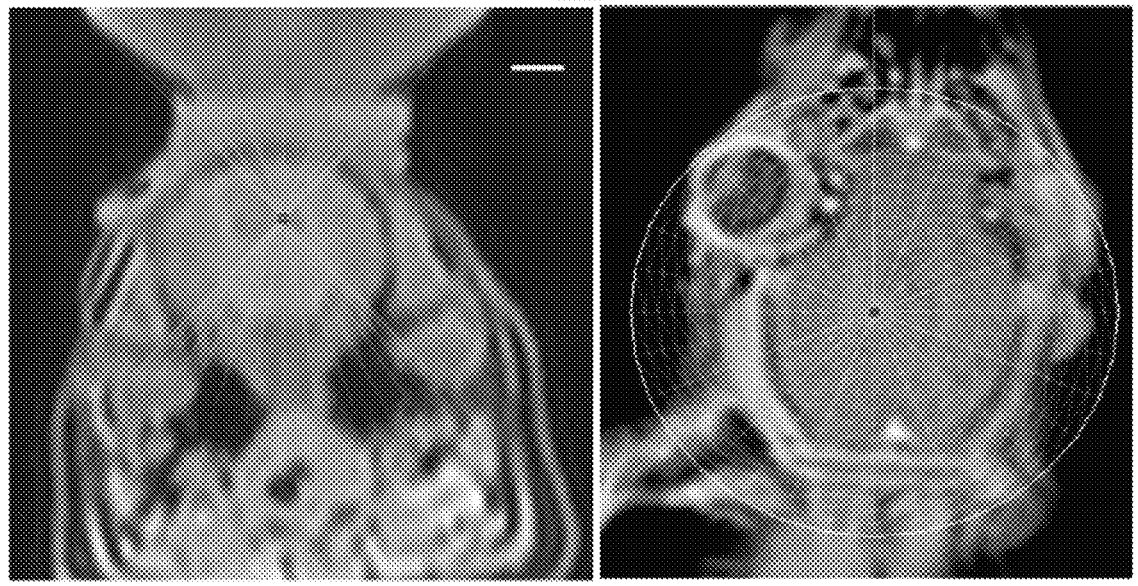
Figure 15:
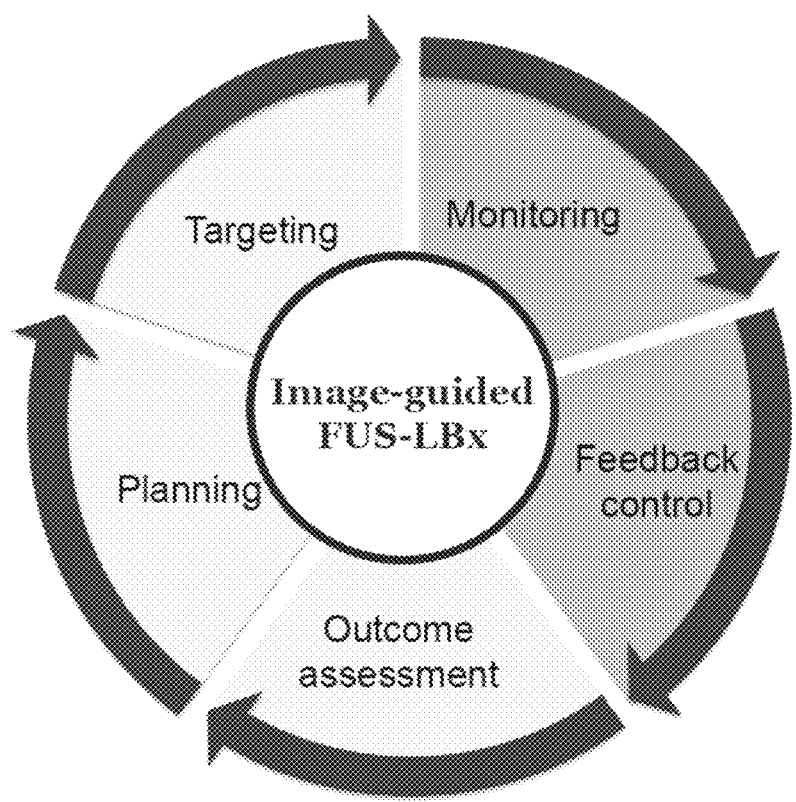
FIG. 15. Monitoring and feedback control using an US sensor to monitor microbubble response to US.
Figure 15:
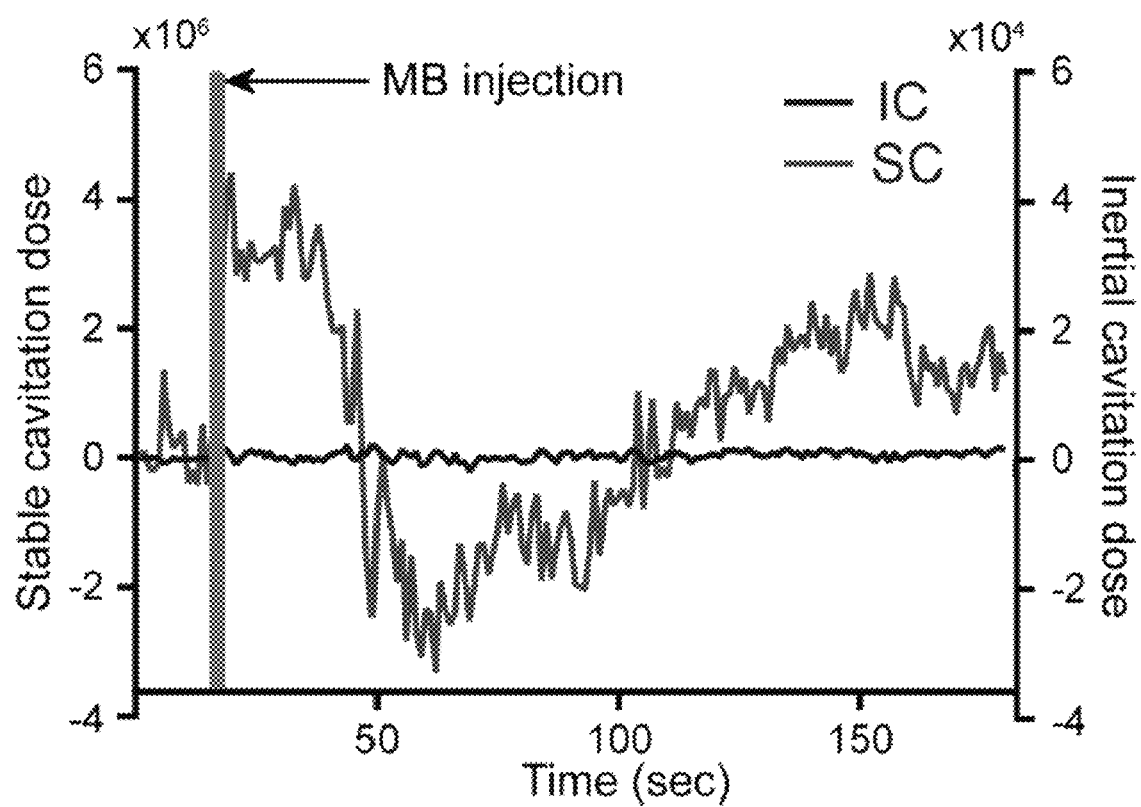
Figure 16:
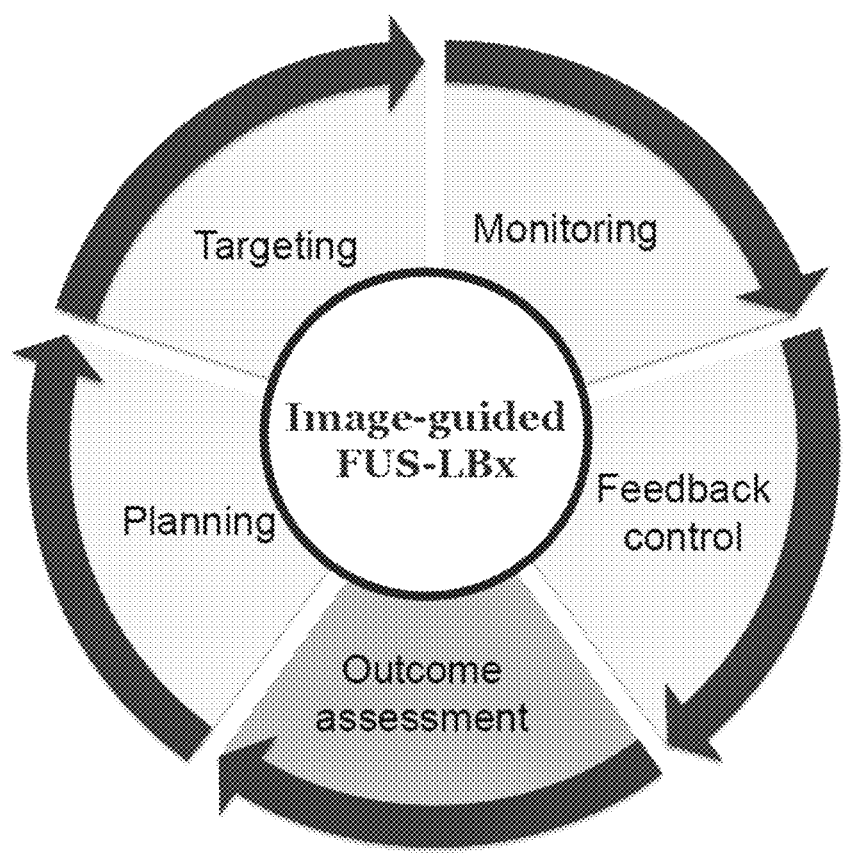
FIG. 16. Outcome assessment with MRI.
Figure 16:
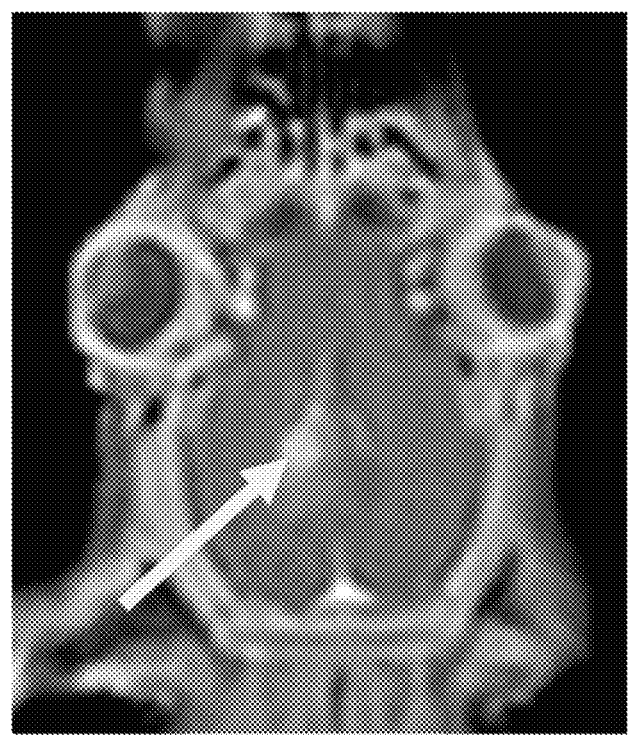

The system allows for planning and targeting of image-guided focused ultrasound liquid biopsy (FUS-LBx) (see e.g., FIG. 14); monitoring and feedback control using an US sensor to monitor microbubble response to US (see e.g., FIG. 15); and outcome assessment (see e.g., FIG. 16).

Described herein is also a method of monitoring cavitation (e.g., microbubble behavior) (see e.g., FIG. 15). The FUS system comprised a sensor that measures acoustic signal. This monitoring informs if the pressure should be increased or decreased by measuring the acoustic signal. Here, the IC line (blue) monitors the bubbles and the SC shows the active calibration to achieve the amount of pressure delivery. This can be used to monitor for safety.

Another routine MRI is performed to detect the leakiness of the area that was administered US.

Figure 17:
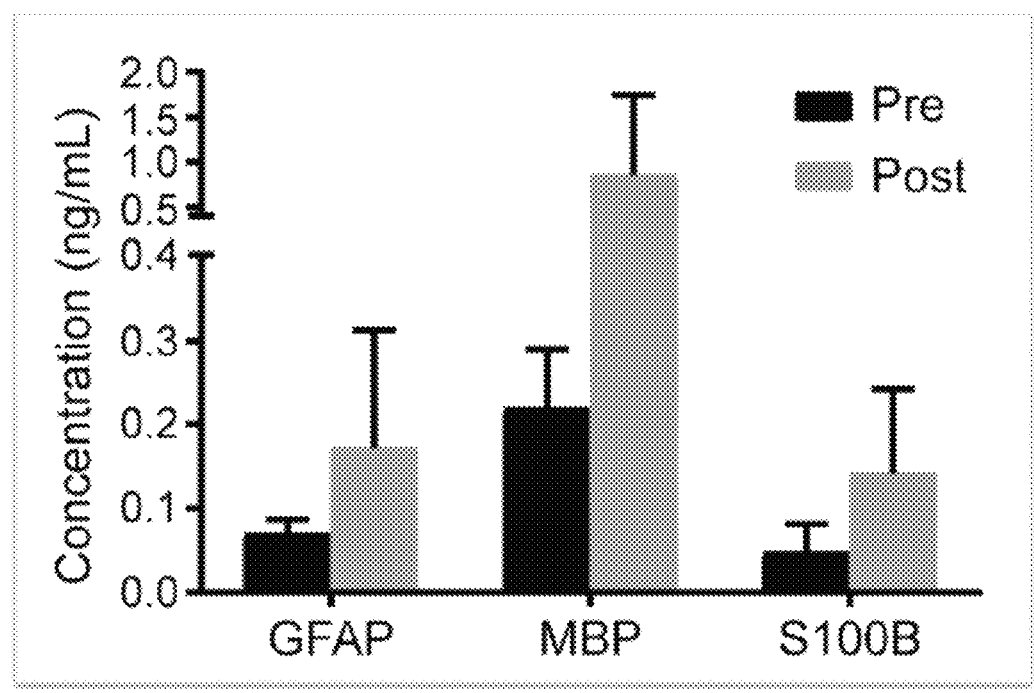
FIG. 17. FUS-LBx in a large animal model (pig). GFAP: Glial fibrillary acidic protein; MBP: Myelin basic protein; S100B: S100 calcium-binding protein B.

FUS-LBx was performed in a large animal model (pig). FIG. 13 shows an image of the pig MRgFUS system. Brain-specific biomarkers, glial fibrillary acidic protein (GFAP), myelin basic protein (MBP), and S100 calcium-binding protein B (S100B) were measured before and after FUS. Increased levels of the brain specific biomarkers were shown in increased levels post-FUS (see e.g., FIG. 17).

What is claimed is:

1. A method of non-invasively releasing biomarkers from a brain or a brain region across a blood brain barrier of a subject comprising:
   (i) applying a focused ultrasound to the brain or the brain region, wherein the focused ultrasound is applied for a period of time and at an acoustic pressure sufficient to disrupt the blood brain barrier and release a detectable quantity of a biomarker across the blood brain barrier;
   (ii) obtaining a biological sample from the subject after applying the focused ultrasound to a subject brain or a subject brain region; and
   (iii) detecting a biomarker in the biological sample,
   wherein the biological sample is a biological fluid selected from the group consisting of: blood, interstitial fluid (ISF), serum, and plasma.

2. The method of claim 1, wherein
   the period of time sufficient to disrupt the blood brain barrier and release a detectable quantity of a biomarker across the blood brain barrier is between about 1 minute and about 4 minutes; or
   the acoustic pressure sufficient to disrupt the blood brain barrier and release a detectable quantity of a biomarker across the blood brain barrier is between about 0.1 MPa and about 10 MPa.

3. The method of claim 1, wherein the biomarker comprises genetic material.

4. The method of claim 3, wherein the genetic material is selected from cell-free RNA, cell-free DNA, mRNA, circulating tumor DNA (ctDNA), or plasma DNA concentration.

5. The method of claim 1, wherein the biomarker is selected from D-2-hydroxyglutarate (D2HG) or IDH1 (R132H) mutation.

6. The method of claim 1, wherein the method comprises: scanning a subject head using a magnetic resonance imaging (MRI) scanner and stereotactically coregistering the subject head and identifying a region to be targeted with the focused ultrasound.

7. The method of claim 1, comprising assessing an effectiveness of the blood brain barrier disruption or release of biomarkers comprising measuring MRI contrast before and after the focused ultrasound, wherein an increase in MRI contrast after the focused ultrasound compared to the MRI contrast before the focused ultrasound indicates successful release of biomarker from the brain or brain region.

8. The method of claim 1, wherein detecting the biomarker in a biological sample comprises genetic testing or sequencing.

9. The method of claim 1, comprising:
   extracting cell-free or exosomic DNA or RNA from the biological sample; and
   detecting somatic mutations or somatic variants in the DNA or RNA using a targeted ultra-deep sequencing technology selected from the group consisting of: ddPCR, AmpliSeq, and HaloPlex sequencing.

10. The method of claim 1, comprising comparing a level of a biomarker in the biological sample after administering the focused ultrasound to a biological sample obtained from the subject before focused ultrasound or of a matched control sample or standard sample.

11. The method of claim 1, wherein
    the brain or brain region comprises a tumor, lesion, or suspected tumor; or
    the subject has or is suspected of having a central nervous system cancer or tumor, a brain lesion, a neurological disease, disorder, or condition, or a neurodegenerative disease disorder, or condition.

12. The method of claim 1, wherein the focused ultrasound is applied for a period of time and at a pressure sufficient to rupture cells to release biomarkers.

13. The method of claim 1, comprising administering microbubbles to a subject in an amount sufficient to disrupt the blood brain barrier upon application of focused ultrasound.

14. The method of claim 1, comprising providing an acoustic sensor; and detecting an acoustic signal, wherein the acoustic sensor is capable of measuring or monitoring cavitational acoustic emissions.

15. The method of claim 1, further comprising monitoring disease progression.

16. The method of claim 1, further comprising monitoring a course of treatment.

17. The method of claim 1, further comprising monitoring treatment response.

18. The method of claim 1, further comprising monitoring treatment efficacy.

19. The method of claim 1, further comprising monitoring drug delivery.

20. The method of claim 1, further comprising personalizing a treatment strategy or treatment selection based on treatment response, treatment efficacy, or disease progression.

21. The method of claim 1, wherein the subject is not administered a contrast agent to the brain.

22. The method of claim 1, wherein the subject is administered a contrast agent consisting essentially of microbubbles.

23. The method of claim 1, wherein the biomarker is not detected by an imaging system.

24. The method of claim 1, wherein administration of a contrast agent is not required to detect the biomarker.

25. The method of claim 1, wherein the biomarker is associated with and the subject has or is suspected of having a central nervous system cancer or tumor, a brain tumor, a brain lesion, a neurological disease, disorder, or condition, or a neurodegenerative disease disorder, or condition.

26. A system suitable for use in delivering focused ultrasound to a brain or a region of a brain of a subject, comprising:
    a device comprising a plurality of modular pieces configured to deliver ultrasound to the brain or a brain region;
    an ultrasound transducer configured to emit a focused ultrasound beam; and
    an acoustic lens configured to control the focused ultrasound beam direction,
    wherein the ultrasound transducer is configured to emit an acoustic pressure between 0.1 MPa and about 10 MPa.

27. The system of claim 26, wherein the system is configured for incorporation into a magnetic resonance imaging (MRI) scanner, wherein the MRI scanner is configured to provide an MRI image for guiding or monitoring of the focused ultrasound.

28. The system of claim 26, wherein the system comprises a helmet configured to fit over a head of a subject; and
    the helmet is demountably coupled to the ultrasound transducer;
    the ultrasound transducer is demountably coupled to the acoustic lens;
    the ultrasound transducer is a flat ultrasound transducer;
    the acoustic lens is a 3D printed acoustic lens; or
    the acoustic lens is a convex lens.

29. The system of claim 28, wherein the helmet is a wearable helmet.

30. The system of claim 26, wherein the system is suitable for use in parallel with a plurality of the systems.

31. The system of claim 26, comprising a sensor capable of measuring or monitoring cavitational acoustic emissions.

32. The system of claim 26, wherein the system comprises one to eight transducers.

33. The method of claim 1, wherein the subject has or is suspected of having Alzheimer's Disease (AD).

34. The method of claim 33, wherein the biomarker is optionally Aβ, tau, or phosphorylated tau.

35. The method of claim 1, wherein the focused ultrasound disrupts brain cells to release genetic information.

36. The system of claim 26, wherein the subject has or is suspected of having Alzheimer's Disease (AD).

37. The system of claim 26, wherein the system comprises a plurality of transducers operably connected to a head mounted interface wearable on the head of a subject.

38. The system of claim 26, wherein the focused ultrasound is configured to disrupt cells to release genetic information.

39. The system of claim 26, wherein the focused ultrasound is configured to disrupt cells to release protein biomarkers.

40. The system of claim 26, wherein the system is configured to release a biomarker associated with a central nervous system cancer or tumor, a brain tumor, a brain lesion, a neurological disease, disorder, or condition, or a neurodegenerative disease disorder, or condition.

41. The system of claim 26, wherein the system is configured to release a biomarker in a biological sample, wherein the biological sample is a biological fluid selected from the group consisting of: blood, interstitial fluid, serum, and plasma.

42. They system of claim 26, further comprising a software configured for magnetic resonance guidance of the focused ultrasound beam.

43. They system of claim 26, further comprising a software configured for stereotactic guidance of the focused ultrasound beam.

44. They system of claim 26, further comprising a software configured for ultrasonic imaging guidance of the focused ultrasound beam.

45. A system suitable for use in delivering focused ultrasound to a brain or a region of a brain of a subject to release biomarkers, comprising:
- a device comprising a plurality of modular pieces configured to deliver ultrasound to the brain or a brain region;
- an ultrasound transducer configured to emit a focused ultrasound beam;
- an acoustic lens configured to control the focused ultrasound beam direction; and
- a wearable interface, wherein the wearable interface is optionally a wearable head mounted interface,
- wherein the ultrasound transducer is configured to emit an acoustic pressure between 0.1 MPa and about 10 MPa.

46. A system suitable for use in delivering focused ultrasound (FUS) to a brain or a region of a brain of a subject to release biomarkers, comprising:
- a device comprising a plurality of modular pieces configured to deliver ultrasound to the brain or a brain region;
- a plurality of ultrasound transducers configured to emit focused ultrasound FUS towards a target; and
- a wearable interface that connects to the plurality of ultrasound transducers, wherein the wearable interface is optionally a wearable head mounted interface,
- wherein the plurality of ultrasound transducers are configured to emit an acoustic pressure between 0.1 MPa and about 10 MPa.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
agaacggcat caaggtgaac                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
tatatcatgg ccgacaagca                                               20

<210> SEQ ID NO 3
<211> LENGTH: 21
<212> TYPE: DNA
<213> ORGANISM: Artificial sequence
<220> FEATURE:
<223> OTHER INFORMATION: Synthetic primer

<400> SEQUENCE: 3
gactcttagc ggtggatcac t                                             21

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
tgctcaggta gtggttgtcg                                               20

<210> SEQ ID NO 5
<211> LENGTH: 20
<212> TYPE: DNA
<213> ORGANISM: Artificial sequence
<220> FEATURE:
<223> OTHER INFORMATION: Synthetic primer

<400> SEQUENCE: 5
actgggtgct caggtagtgg                                               20

<210> SEQ ID NO 6
<211> LENGTH: 20
<212> TYPE: DNA
<213> ORGANISM: Artificial sequence
<220> FEATURE:
<223> OTHER INFORMATION: Synthetic primer

<400> SEQUENCE: 6
cgttcttcat cgacgcacga                                               20
```